United States Patent [19]

Berger et al.

[11] Patent Number: 5,369,125
[45] Date of Patent: Nov. 29, 1994

[54] CHOLESTEROL-LOWERING AGENTS

[75] Inventors: Gregory D. Berger, Belle Mead;
James D. Bergstrom, Neshanic;
Tesfaye Biftu, Westfield; Robert L.
Bugianesi, Colonia, all of N.J.;
Robert M. Burk, Laguna Beach,
Calif.; Narindar N. Girotra, Old
Bridge; C. H. Kuo, South Plainfield;
William H. Parsons, Edison; Mitree
M. Ponpipom, Branchburg, all of
N.J.; Lori L. Whiting, West
Carrollton, Ohio

[73] Assignee: Merck & Co., Inc., Rahway, N.J.

[21] Appl. No.: 33,913

[22] Filed: Mar. 19, 1993

Related U.S. Application Data

[63] Continuation-in-part of Ser. No. 916,774, Jul. 17, 1992, abandoned.

[51] Int. Cl.⁵ .................. A61K 31/335; C07D 319/04
[52] U.S. Cl. ....................................... 514/452; 549/363; 549/305; 549/229; 548/311.7; 544/148; 514/397; 514/231.5
[58] Field of Search ................ 549/363, 310, 60, 58, 549/28, 23, 305, 229; 548/518, 517, 455, 197, 187, 336; 514/452, 397, 231.5; 544/148

[56] References Cited

U.S. PATENT DOCUMENTS

| | | | |
|---|---|---|---|
| 5,025,003 | 6/1991 | Biller | 514/120 |
| 5,026,554 | 6/1991 | Bartizal et al. | 424/404 |
| 5,053,425 | 10/1991 | Bartizal et al. | 514/452 |
| 5,055,487 | 10/1991 | Bartizal et al. | 514/452 |
| 5,096,923 | 3/1992 | Bergstrom et al. | 514/452 |
| 5,102,907 | 4/1992 | Bergstrom et al. | 514/456 |
| 5,132,320 | 7/1992 | Bergstrom et al. | 514/452 |

FOREIGN PATENT DOCUMENTS

| | | |
|---|---|---|
| 0494622 | 7/1992 | European Pat. Off. |
| 0503520 | 9/1992 | European Pat. Off. |
| WO92/12156 | 7/1992 | WIPO |
| WO92/12157 | 7/1992 | WIPO |
| WO92/12158 | 7/1992 | WIPO |
| WO92/12159 | 7/1992 | WIPO |
| WO92/12160 | 7/1992 | WIPO |
| WO92/16530 | 10/1992 | |

OTHER PUBLICATIONS

Baxter et al., J. Biol. Chem 267, 11705–11708, (1992).

*Primary Examiner*—Nicky Chan
*Attorney, Agent, or Firm*—Catherine A. Dolan; Melvin Winokur; Paul D. Matukaitis

[57] ABSTRACT

This invention relates to compounds of structural formula (I):

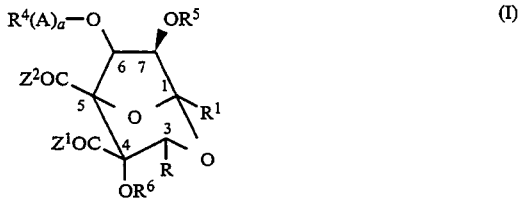

which are squalene synthase inhibitors and thus useful as cholesterol lowering agents and antifungal agents. These compounds are also inhibitors of farnesyl protein transferase and farnesylation of the oncogene protein Ras and thus useful in treating cancer.

15 Claims, No Drawings

CHOLESTEROL-LOWERING AGENTS

CROSS REFERENCE TO RELATED APPLICATIONS

This application is a continuation in part of U.S. patent application Ser. No. 07/916,774, filed Jul. 17, 1992, presently abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin) and ZOCOR ®, now commercially available, are members of a group of very active antihypercholesterolemic agents that function by limiting cholesterol biosynthesis by inhibiting the enzyme HMG-CoA reductase.

Squalene synthase (also called squalene synthetase) is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analog containing compounds such as those described in P. Ortiz de Montellano et al., J. Med. Chem. 20, 243 (1977), E. J. Corey and R. Volante, J. Am. Chem. Soc., 98, 1291 (1976), and U.S. Pat. No. 5,025,003 to S. Billet. U.S. Pat. No. 4,871,721 to S. Billet describes isoprenoid(phosphinylmethyl) phosphonates as inhibitors of squalene synthase.

U.S. Pat. Nos. 5,096,923; 5,026,554; and 5,102,907 disclose non-phosphorus-containing substituted 2,8-dioxabicyclo-[3.2.1]octane derivatives useful as squalene synthase inhibitors.

Recently it has been shown that certain natural product nonphosphorous containing inhibitors of squalene synthase and their esters are useful in inhibiting fungal growth. This utility is described in U.S. Pat No. 5,026,554.

The present invention is directed to compounds of structural formula (I) which are squalene synthase inhibitors for the inhibition of fungal growth.

The present invention is also directed to compounds of structural formula (I) which are inhibitors of farnesyl-protein transferase for inhibition of farnesylation of the oncogene protein Ras and the treatment of cancer.

These compounds are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid: Reiss et. al., ibid; Reies et al., *PNAS,* 88:732-736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras are described herein.

The present invention provides nonphosphorus containing inhibitors of squalene synthase.

DETAILED DESCRIPTION OF THE INVENTION

The present invention is directed to novel compounds of structural formula (I) which are squalene synthase inhibitors:

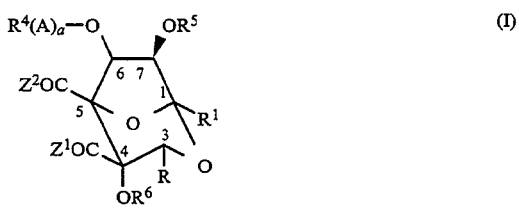

wherein
R is:
(1) $C_{1-10}$ alkyl,
(2) $C_{1-10}$ alkylcarbonyl,
(3) substituted $C_{1-10}$ alkyl wherein one or more of the carbons is substituted with $X^2$,
(4) substituted $C_{1-10}$ alkylcarbonyl wherein one or more of the carbons is substituted with $X^2$,
(5) $C_{1-10}$ alkyl wherein one or more of the carbon atoms is replaced by $-NR^3-$, $-O-$, or $-S(O)_n-$,
(6) substituted $C_{1-10}$ alkyl wherein one or more of the carbon atoms is replaced by $-NR^3-$, $-O-$, or $-S(O)_n-$ and wherein one or more of the carbons is substituted with $X^2$,
(7) $C_{2-10}$ alkenyl wherein alkenyl contains one, two or three double bonds,
(8) substituted $C_{2-10}$ alkenyl wherein alkenyl contains one, two or three double bonds and wherein one or more of the carbons is substituted with $X^2$,
(9) $C_{2-10}$ alkenyl wherein alkenyl contains one, two or three double bonds and one or more of the nonolefinic carbons is replaced with $-NR^3-$, or $-O-$ or $-S(O)_n-$,
(10) substituted $C_{2-10}$ alkenyl wherein alkenyl contains one, two or three double bonds and one or more of the nonolefinic carbons is replaced with $-NR^3-$, $-O-$, or $-S(O)_n-$ and wherein one or more of the carbons is substituted with $X^2$,
(11) $C_{1-10}$ alkylcarbonyl wherein one or more of the carbon atoms is replaced by $-NR^3-$, $-O-$, or $-S(O)_n-$,
(12) substituted $C_{1-10}$ alkylcarbonyl wherein one or more of the carbon atoms is replaced by $-NR^3-$, $-O-$, or $-S(O)_n-$ and wherein one or more of the carbons is substituted with $X^2$,
(13) $C_{2-10}$ alkenylcarbonyl wherein alkenyl contains one, two or three double bonds,
(14) substituted $C_{2-10}$ alkenylcarbonyl wherein alkenyl contains one, two or three double bonds and wherein one or more of the carbons is substituted with $X^2$,

(15) $C_{2-10}$ alkenylcarbonyl wherein alkenyl contains one, two or three double bonds and one or more of the nonolefinic carbons is replaced with —$NR^3$—, —O— or —$S(O)_n$—, or

(16) substituted $C_{2-10}$ alkenylcarbonyl wherein alkenyl contains one, two or three double bonds and one or more of the nonolefinic carbons is replaced with —$NR^3$—, —O—, or —$S(O)_n$— and wherein one or more of the carbons is substituted with $X^2$;

a is 0 or 1;

A is —C(O)—, —$NR^3$—C(O)—, or —OC(O)—;

$R^1$ is:
(1) $C_{1-20}$alkyl,
(2) substituted $C_{1-20}$alkyl wherein one or more of the carbons is substituted with $X^3$,
(3) $C_{1-20}$alkyl wherein one or more of the carbons is replaced by —$NR^3$, —O— or —$S(O)_n$—,
(4) substituted $C_{1-20}$alkyl wherein one or more of the carbons is replaced by —$NR^3$—, —O— or —$S(O)_n$— and wherein one or more of the carbon atoms is substituted with $X^3$,
(5) aryl substituted with X and Y,
(6) heteroaryl substituted with X and Y,
(7) $C_{2-20}$alkenyl wherein alkenyl contains one or more double bonds,
(8) substituted $C_{2-20}$alkenyl wherein alkenyl contains one or more double bonds and wherein one or more of the carbons is substituted with $X^3$,
(9) $C_{2-20}$alkenyl wherein alkenyl contains one or more double bonds and one or more of the nonolefinic carbons is replaced by —$NR^3$—, —O— or —$S(O)_n$—,
(10) substituted $C_{2-20}$alkenyl wherein alkenyl contains one or more double bonds and one or more of the nonolefinic carbons is replaced by —$NR^3$—, —O— or —$S(O)_n$— and wherein one or more of the carbons is substituted with $X^3$,
(11) $C_{3-10}$cycloalkyl, or
(12) substituted $C_{3-10}$cycloalkyl in which one or more of the carbon atoms is substituted with:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) $arylS(O)_n$, wherein aryl is substituted with X and Y,
 (m) $R_3$—C(O)—$NR^3$—,
 (n) $R^3R^3N$—C(O)—,
 (o) $C_{1-10}alkylS(O)_n$—,
 (p) $C_{1-10}$alkyl,
 (q) —$CO_2H$,
 (r) -vinylidene,
 (s) $R^3$—C(O)—,
 (t) $R^2O$—C(O)—O—,
 (u) $R^3R^3N$—C(O)—O—, or
 (v) $R^2O$—C(O)—$NR^3$—;

each $R^2$ is independently:
(1) $C_{1-10}$alkyl,
(2) aryl substituted with X and Y,
(3) $arylC_{1-4}$alkyl wherein aryl is substituted with X and Y,
(4) heteroaryl wherein heteroaryl is substituted with X and Y,
(5) $heteroarylC_{1-4}$alkyl- wherein heteroaryl is substituted with X and Y,
(6) $heterocycloalkylC_{1-4}$alkyl-,
(7) $C_{2-10}$alkenyl,
(8) $arylC_{2-10}$alkenyl wherein aryl is substituted with X and Y, or
(9) $C_{3-10}$alkynyl;

each $R^3$ is independently:
(1) $C_{1-10}$alkyl,
(2) aryl substituted with X and Y,
(3) $arylC_{1-4}$alkyl wherein aryl is substituted with X and Y,
(4) heteroaryl wherein heteroaryl is substituted with X and Y,
(5) $heteroarylC_{1-4}$alkyl- wherein heteroaryl is substituted with X and Y,
(6) $heterocycloalkylC_{1-4}$alkyl-,
(7) $C_{2-10}$alkenyl,
(8) $arylC_{2-10}$alkenyl wherein aryl is substituted with X and Y,
(9) $C_{3-10}$alkynyl,
(10) hydrogen, or
(11) $C_{1-5}$alkyl substituted with $X^1$;

$R^4$ is:
(1) $C_{1-20}$alkyl,
(2) substituted $C_{1-20}$alkyl in which one or more carbon atoms is substituted with $X^3$,
(3) $C_{1-20}$alkyl wherein one or more of the carbons is replaced by —$NR_3$—, —O—, or —$S(O)_n$—,
(4) substituted $C_{1-20}$alkyl wherein one or more of the carbons is replaced by —$NR^3$—, —O— or —$S(O)_n$— and wherein one or more carbon atoms is substituted with $X^3$,
(5) aryl substituted with X and Y,
(6) heteroaryl substituted with X and Y,
(7) $C_{2-20}$alkenyl wherein alkenyl contains one or more double bonds,
(8) substituted $C_{2-20}$alkenyl wherein alkenyl contains one or more double bonds and wherein one or more of the carbons is substituted with $X^3$,
(9) $C_{2-20}$alkenyl wherein alkenyl contains one or more double bonds and one or more of the nonolefinic carbons is replaced by —$NR^3$—, —O— or —$S(O)_n$—,
(10) substituted $C_{2-20}$alkenyl wherein alkenyl contains one or more double bonds and one or more of the nonolefinic carbons is replaced by —$NR^3$—, —O— or —$S(O)_n$— and wherein one or more of the carbon atoms is substituted with $X^3$,
(11) $C_{3-10}$cycloalkyl,
(12) substituted $C_{3-10}$cycloalkyl in which one or more of the carbon atoms is substituted with $X^3$, or
(13) hydrogen;

$R^5$ is:
(1) hydrogen,
(2) $C_{1-10}$alkyl,
(3) aryl substituted with X and Y,
(4) $arylC_{1-4}$alkyl, wherein aryl is substituted with X and Y,
(5) $R^2O$—C(O)—,
(6) $C_{3-10}$cycloalkyl,
(7) $R^3$—C(O)—, or
(8) $R^3R^3N$—C(O)—;

each $R^6$ is independently:

(1) $C_{1-20}$alkyl,
(2) substituted $C_{1-20}$alkyl in which one or more of the carbon atoms is substituted with $X^3$,
(3) $C_{1-20}$alkyl wherein one or more of the carbons is replaced by —$NR^3$—, —O—, or —$S(O)_n$—,
(4) substituted $C_{1-20}$alkyl wherein one or more of the carbons is replaced by —$NR^3$—, —O— or —$S(O)_n$— and wherein one or more of the carbon atoms is substituted with $X^3$,
(5) $C_{2-20}$alkenyl wherein alkenyl contains one or more double bonds,
(6) substituted $C_{2-20}$alkenyl wherein alkenyl contains one or more double bonds and wherein one or more of the carbons is substituted with:
   (a) halogen,
   (b) hydroxy,
   (c) $R^3R^3N$—,
   (d) $R^2O$—,
   (e) $R^2O$—C(O)—,
   (f) $R^3$—C(O)—O—,
   (g) oxo,
   (h) $C_{3-10}$cycloalkyl,
   (i) aryl substituted with X and Y,
   (j) heteroaryl substituted with X and Y,
   (k) heterocycloalkyl,
   (l) aryl $S(O)_n$—, wherein aryl is substituted with X and Y,
   (m) $R^3$—C(O)—$NR^3$—,
   (n) $R^3R^3N$—C(O)—,
   (o) —$CO_2H$,
   (p) -vinylidene,
   (q) $R^3$—C(O)—,
   (r) $R^2O$—C(O)—O—,
   (s) $R^3R^3N$—C(O)—O—,
   (t) $R^2O$—C(O)—$NR^3$—, or
   (u) —OC(O)O—, which forms a five-membered ring:

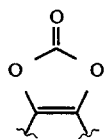

with adjacent olefinic carbons,
(7) $C_{2-20}$alkenyl wherein alkenyl contains one or more double bonds and one or more of the nonolefinic carbons is replaced by —$NR^3$—, —O— or —$S(O)_n$—,
(8) substituted $C_{2-20}$alkenyl wherein alkenyl contains one or more double bonds and one or more of the nonolefinic carbons is replaced by —$NR^3$—, —O— or —$S(O)_n$— and wherein one or more of the carbon atoms is substituted with:
   (a) halogen
   (b) hydroxy,
   (c) $R^3R^3N$—,
   (d) $R^2O$—,
   (e) $R^2O$—C(O)—,
   (f) $R^3$—C(O)—O—,
   (g) oxo,
   (h) $C_{3-10}$cycloalkyl,
   (i) aryl substituted with X and Y,
   (j) heteroaryl substituted with X and Y,
   (k) heterocycloalkyl,
   (l) aryl $S(O)_n$—, wherein aryl is substituted with X and Y,
   (m) $R^3$—C(O)—$NR^3$—,
   (n) $R^3R^3N$—C(O)—,
   (o) —$CO_2H$,
   (p) -vinylidene,
   (q) $R^3$—C(O)—,
   (r) $R^2O$—C(O)—O—,
   (s) $R^3R^3N$—C(O)—O—,
   (t) $R^2O$—C(O)—$NR^3$— or
   (u) —OC(O)O—, which forms a five-membered ring:

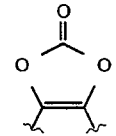

with adjacent olefinic carbons,
(9) $C_{2-20}$alkynyl wherein alkynyl contains one or more triple bonds,
(10) substituted $C_{2-20}$alkynyl wherein alkynyl contains one or more triple bonds and wherein one or more of the carbons is substituted with $X^3$,
(11) $C_{2-20}$alkynyl wherein alkynyl contains one or more triple bonds and one or more of the saturated carbons is replaced by —$NR^3$—, —O— or —$S(O)_n$—,
(12) substituted $C_{2-20}$alkynyl wherein alkynyl contains one or more double bonds and one or more of the saturated carbons is replaced by —$NR^3$—, —O— or —$S(O)_n$— and wherein one or more of the carbon atoms substituted with $X^3$,
(13) aryl substituted with X and Y,
(14) Heteroaryl substituted with X and Y,
(15) $C_{3-5}$ cycloalkyl,
(16) substituted $C_{3-5}$ cycloalkyl in which one or more of the carbon atoms is substituted with:
   (a) $R^3O$—, or
   (b) $R^3R^3N$—, or
(17) hydrogen;
aryl including X, Y substitution is:

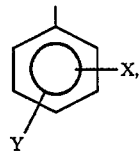

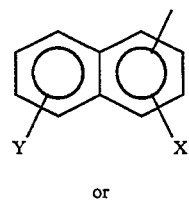

or

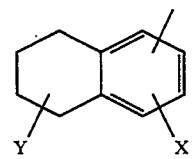

heteroaryl including X, Y substitution is

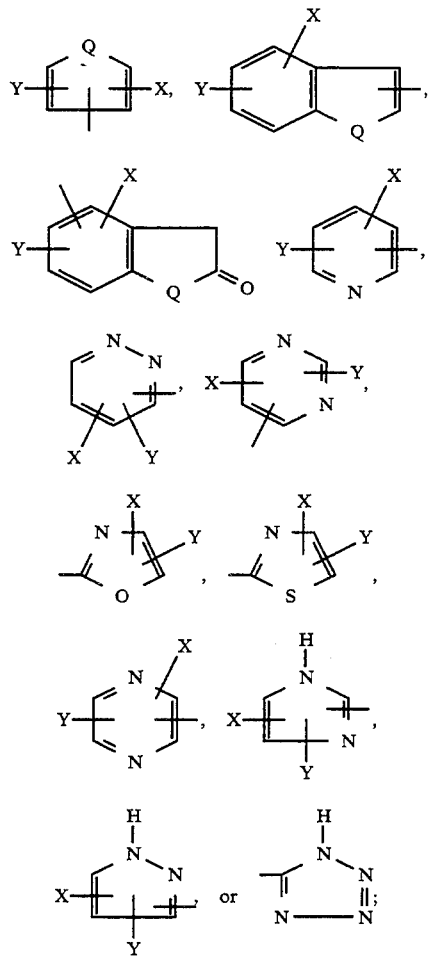

wherein:
Q is —NR³, —O— or —S—;
heterocycloalkyl is:

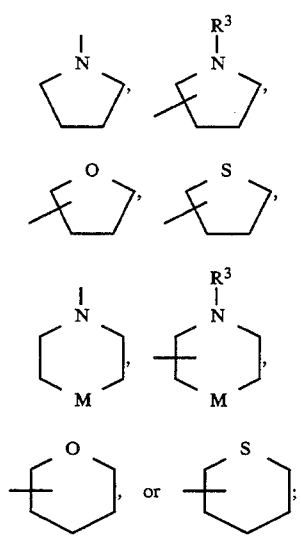

wherein:
M is —NR³, —O—, —S— or —CH₂—
X and Y are each independently:
(1) hydrogen,
(2) hydroxy,
(3) halogen,
(4) trifluoromethyl,
(5) $C_{1-10}$alkyl,
(6) aryl substituted with $X^1$ and $Y^1$,
(7) R²O—,
(8) arylcarbonyloxy-, wherein aryl is substituted with $X^1$ and $Y^1$,
(9) R³—C(O)—O—,
(10) —CO₂R²,
(11) —CO₂H, or
(12) nitro;
$X^1$ and $Y^1$ are each independently:
(1) hydrogen,
(2) hydroxy,
(3) halogen,
(4) trifluoromethyl,
(5) $C_{1-4}$alkyl,
(6) R²O—,
(7) R³—C(O)—O—,
(8) —CO₂R²,
(9) —CO₂H, or
(10) nitro;
each $X^2$ is independently:
(1) halogen,
(2) hydroxy,
(3) R³R³N—,
(4) R²O—,
(5) R²O—C(O)—,
(6) R³—C(O)—O—,
(7) oxo,
(8) $C_{3-10}$cycloalkyl,
(9) aryl substituted with X and Y,
(10) heteroaryl substituted with X and Y,
(11) heterocycloalkyl,
(12) aryl S(O)ₙ, wherein aryl is substituted with X and Y,
(13) R³—C(O)—NR³—,
(14) R³R³N—C(O)—,
(15) —CO₂H,
(16) -vinylidene,
(17) R³—C(O)—,
(18) R²O—C(O)—O—,
(19) R³R³NC(O)—O—, or
(20) R²O—C(O)—NR³—;
each $X^3$ is independently:
(1) halogen
(2) hydroxy,
(3) R³R³N—,
(4) R²O—,
(5) R²O—C(O)—,
(6) R³—C(O)—O—,
(7) oxo,
(8) $C_{3-10}$cycloalkyl,
(9) aryl substituted with X and Y,
(10) heteroaryl substituted with X and Y,
(11) heterocycloalkyl,
(12) aryl S(O)ₙ, wherein aryl is substituted with X and Y,
(13) R³—C(O)—NR³—,
(14) R³R³N—C(O)—,
(15) —CO₂H,
(16) -vinylidene,
(17) R³—C(O)—,
(18) R²O—C(O)—O—,
(19) R³R³NC(O)—O—, or
(20) R²O—C(O)—NR³—;
n is 0, 1 or 2;

$Z^1$ and $Z^2$ are each independently:
(1) —$OR^6$,
(2) —$SR^6$, or
(3) —$NR^6R^6$;

or a pharmaceutically acceptable salt.

One embodiment of this invention is the compounds of formula (I) wherein:

R is:
(1) $C_{1-10}$ alkyl,
(2) substituted $C_{1-10}$ alkyl wherein one or more of the carbons is substituted with $X^2$,
(3) $C_{1-10}$ alkyl wherein one or more of the carbon atoms is replaced by —$NR^3$—, —O—, or —S(O)$_n$—,
(4) substituted $C_{1-10}$ alkyl wherein one or more of the carbon atoms is replaced by —$NR^3$—, —O—, or —S(O)$_n$— and wherein one or more of the carbons is substituted with $X^2$,
(5) $C_{2-10}$ alkenyl wherein alkenyl contains one, two or three double bonds,
(6) substituted $C_{2-10}$ alkenyl wherein alkenyl contains one, two or three double bonds and wherein one or more of the carbons is substituted with $X^2$,
(7) $C_{2-10}$ alkenyl wherein alkenyl contains one, two or three double bonds and one or more of the nonolefinic carbons is replaced with —$NR^3$—, or —O— or —S(O)$_n$—,
(8) substituted $C_{2-10}$ alkenyl wherein alkenyl contains one, two or three double bonds and one or more of the nonolefinic carbons is replaced with —$NR^3$—, —O—, or —S(O)$_n$— and wherein one or more of the carbons is substituted with $X^2$, and a, n, A, $R^1$, $R^2$, $R^3$, $R^4$, $R^5$, $R^6$, X, Y, $X^1$, $Y^1$, $X^2$, $Y^2$, $X^3$, $Y^3$, $Z^1$ and $Z^2$ are as above.

Another embodiment of this invention is the compounds of formula (I) wherein:

R is:
(1) $C_{1-10}$ alkylcarbonyl,
(2) substituted $C_{1-10}$ alkylcarbonyl wherein one or more of the carbons is substituted with $X^2$,
(3) $C_{1-10}$ alkylcarbonyl wherein one or more of the carbon atoms is replaced by —$NR^3$—, —O—, or —S(O)$_n$—,
(4) substituted $C_{1-10}$ alkylcarbonyl wherein one or more of the carbon atoms is replaced by —$NR^3$—, —O—, or —S(O)$_n$— and wherein one or more of the carbons is substituted with $X^2$,
(5) $C_{2-10}$ alkenylcarbonyl wherein alkenyl contains one, two or three double bonds,
(6) substituted $C_{2-10}$ alkenylcarbonyl wherein alkenyl contains one, two or three double bonds and wherein one or more of the carbons is substituted with $X^2$,
(7) $C_{2-10}$ alkenylcarbonyl wherein alkenyl contains one, two or three double bonds and one or more of the nonolefinic carbons is replaced with —$NR^3$—, —O— or —S(O)$_n$—, or
(8) substituted $C_{2-10}$ alkenylcarbonyl wherein alkenyl contains one, two or three double bonds and one or more of the nonolefinic carbons is replaced with —$NR^3$—, —O—, or —S(O)$_n$— and wherein one or more of the carbons is substituted with $X^2$;

and $R^1$, $R^2$, a, A, $R^3$, $R^4$, $R^5$, $R^6$, X, Y, $X^1$, $Y^1$, $X^2$, $Y^2$, $X^3$, $Y^3$, n, $Z^1$ and $Z^2$ are as above.

Another embodiment is the compounds wherein:

R is:
(1) $C_{1-10}$ alkyl,
(2) $C_{1-10}$ alkylcarbonyl,
(3) substituted $C_{1-10}$ alkyl wherein one or more of the carbons is substituted with $X^2$,
(4) substituted $C_{1-10}$ alkylcarbonyl wherein one or more of the carbons is substituted with $X^2$,
(5) $C_{1-10}$ alkyl wherein one or more of the carbon atom is replaced by —$NR^3$—, —O—, or —S(O)$_n$—,
(6) substituted $C_{1-10}$ alkyl wherein one or more of the carbon atoms is replaced by —$NR^3$—, —O—, or —S(O)$_n$— and wherein one or more of the carbons is substituted with $X^2$,
(7) $C_{2-10}$ alkenyl wherein alkenyl contains one, two or three double bonds,
(8) $C_{1-10}$ alkylcarbonyl wherein one or more of the carbon atoms is replaced by —$NR^3$—, —O—, or —S(O)$_n$—, or
(9) substituted $C_{1-10}$ alkylcarbonyl wherein one or more of the carbon atoms is replaced by —$NR^3$,— —O—, or —S(O)$_n$— and wherein one or more of the carbons is substituted with $X^2$;

$R^1$ is:
(1) $C_{1-20}$ alkyl,
(2) substituted $C_{1-20}$ alkyl in which one or more of the carbons is substituted with $X^3$,
(3) $C_{1-20}$ alkyl wherein one or more of the carbons is replaced by —$NR^3$—, —O—, or —S(O)$_n$—,
(4) substituted $C_{1-20}$ alkyl wherein one or more of the carbons is replaced by —$NR^3$—, —O— or —S(O)$_n$— and wherein one or more of the carbons is substituted with $X^3$,
(5) aryl substituted with X and Y,
(6) heteroaryl substituted with X and Y,
(7) $C_{2-20}$ alkenyl wherein alkenyl contains one, two or three double bonds,
(8) substituted $C_{2-20}$ alkenyl wherein alkenyl contains one, two or three double bonds and wherein one or more of the carbons is substituted with $X^3$,
(9) $C_{2-20}$ alkenyl wherein alkenyl contains one, two or three double bonds and one or more of the nonolefinic carbons is replaced by —$NR^3$—, —O— or —S(O)$_n$—, or
(10) substituted $C_{2-20}$ alkenyl wherein alkenyl contains one, two or three double bonds and one or more of the nonolefinic carbons is replaced by —$NR^3$, —O— or —S(O)$_n$— and wherein one or more of the carbons is substituted with $X^3$;

each $R^2$ is independently:
(1) $C_{1-10}$ alkyl,
(2) aryl substituted with X and Y,
(3) aryl$C_{1-4}$alkyl wherein aryl is substituted with X and Y,
(4) heteroaryl wherein heteroaryl is substituted with X and Y,
(5) heteroaryl$C_{1-4}$alkyl- wherein heteroaryl is substituted with X and Y,
(6) heterocycloalkyl$C_{1-4}$alkyl-,
(7) $C_{2-10}$ alkenyl,
(8) aryl$C_{2-10}$alkenyl wherein aryl is substituted with X and Y, or
(9) $C_{3-10}$ alkynyl;

each $R^3$ is independently:
(1) $C_{1-10}$ alkyl,
(2) aryl substituted with X and Y,
(3) aryl$C_{1-4}$alkyl wherein aryl is substituted with X and Y,
(4) heteroaryl wherein heteroaryl is substituted with X and Y, (5) heteroaryl$C_{1-4}$alkyl- wherein heteroaryl is substituted with X and Y,
(6) heterocycloalkyl$C_{1-4}$alkyl-,
(7) $C_{2-10}$alkenyl,
(8) aryl$C_{2-10}$alkenyl wherein aryl is substituted with X and Y,
(9) $C_{3-10}$alkynyl,
(10) hydrogen, or
(11) $C_{1-5}$alkyl substituted with $X^1$;

$R^4$ is:
(1) $C_{1-20}$alkyl,
(2) substituted $C_{1-20}$alkyl in which one or more of the carbons is substituted with $X^3$,
(3) $C_{1-20}$alkyl wherein one or more of the carbons is replaced by —$NR^3$—, —O—, or —$S(O)_n$—,
(4) substituted $C_{1-20}$alkyl wherein one or more of the carbons is replaced by —$NR^3$—, —O— or —$S(O)_n$— and wherein one or more of the carbon is substituted with $X^3$,
(5) aryl substituted with X and Y,
(6) heteroaryl substituted with X and Y,
(7) $C_{2-20}$ alkenyl wherein alkenyl contains one, two or three double bonds,
(8) substituted $C_{2-20}$ alkenyl wherein alkenyl contains one, two or three double bonds and wherein one or more of the carbons is substituted with $X^3$,
(9) $C_{2-20}$alkenyl wherein alkenyl contains one, two or three double bonds and one or more of the nonolefinic carbons is replaced by —$NR^3$—, —O— or —$S(O)_n$—,
(10) substituted $C_{2-20}$alkenyl wherein alkenyl contains one, two or three double bonds and one or more of the nonolefinic carbons is replaced by —$NR^3$—, —O— or —$S(O)_n$— and wherein one or more of the carbons is substituted with $X^3$, or
(11) hydrogen;

$R^5$ is:
(1) hydrogen,
(2) $C_{1-10}$alkyl,
(3) aryl substituted with X and Y,
(4) aryl$C_{1-4}$alkyl, wherein aryl is substituted with X and Y,
(5) $R^2O$—C(O)—,
(6) $C_{3-10}$cycloalkyl,
(7) $R^2$—C(O)—, or
(8) $R^3R^3N$—C(O)—;

each $R^6$ is independently:
(1) $C_{1-20}$alkyl,
(2) substituted $C_{1-20}$alkyl in which one or more of the carbon atoms is substituted with $X^3$,
(3) $C_{1-20}$alkyl wherein one or more of the carbons is replaced by —$NR^3$—, —O—, or —$S(O)_n$—,
(4) substituted $C_{1-20}$alkyl wherein one or more of the carbons is replaced by —$NR^3$—, —O— or —$S(O)_n$— and wherein one or more of the carbons is substituted with $X^3$,
(5) $C_{2-20}$alkenyl wherein alkenyl contains one, two or three double bonds,
(6) substituted $C_{2-20}$alkenyl wherein alkenyl contains one, two or three double bonds and wherein one or more of the carbons is substituted with:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl $S(O)_n$—, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—, or
  (u) —OC(O)O—, which forms a five-membered ring

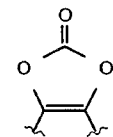

with adjacent olefinic carbon atoms,
(7) $C_{2-20}$alkenyl wherein alkenyl contains one, two or three double bonds and one or more of the nonolefinic carbons is replaced by —$NR^3$—, —O— or —$S(O)_n$—,
(8) substituted $C_{2-20}$alkenyl wherein alkenyl contains one, two or three double bonds and one or more of the nonolefinic carbons is replaced by —$NR^3$—, —O— or —$S(O)_n$— and wherein one or more of the carbons is substituted with:
  (a) halogen,
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl $S(O)_n$—, wherein aryl is substituted with X and Y,
  (m) $R^3$—C(O)—$NR^3$—,
  (n) $R^3R^3N$—C(O)—,
  (o) —$CO_2H$,
  (p) -vinylidene,
  (q) $R^3$—C(O)—,
  (r) $R^2O$—C(O)—O—,
  (s) $R^3R^3N$—C(O)—O—, and
  (t) $R^2O$—C(O)—$NR^3$—, or
  (u) —OC(O)O—, which forms a five-membered ring:

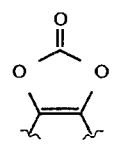

with adjacent olefinic carbons,
(9) $C_{2-20}$alkynyl wherein alkynyl contains one or more triple bonds,

(10) substituted $C_{2-20}$alkynyl wherein alkynyl contains one or more triple bonds and wherein one or more of the carbons is substituted with $X^3$,

(11) $C_{2-20}$alkynyl wherein alkynyl contains one or more triple bonds and one or more of the saturated carbons is replaced by —$NR^3$—, —O— or —S(O)$_n$—,

(12) substituted $C_{2-20}$alkynyl wherein alkynyl contains one or more triple bonds and one or more of the saturated carbons is replaced by —$NR^3$—, —O— or —S(O)$_n$— and wherein one or more of the carbons is substituted with $X^3$,

(13) aryl substituted with X and Y;

(14) heteroaryl substituted with X and Y,

(15) $C_{3-5}$ cycloalkyl,

(16) substituted $C_{3-5}$ cycloalkyl in which one or more of the carbons is substituted with:
 (a) $R^3O$—, or
 (b) $R^3R^3N$—, or

(17) hydrogen;

aryl including X, Y substitution is

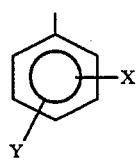

heteroaryl including X, Y substitution is:

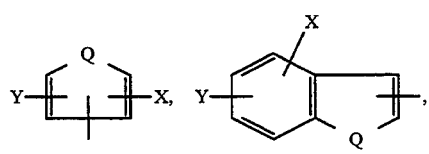

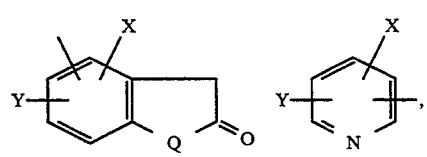

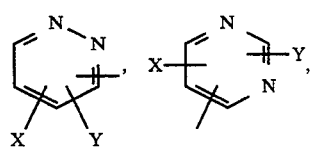

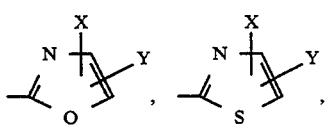

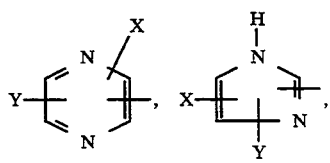

-continued

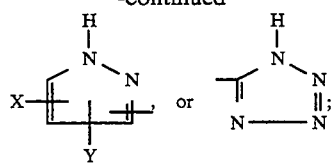

wherein:
Q is —$NR^3$, —O— or —S—;
heterocycloalkyl is selected from:

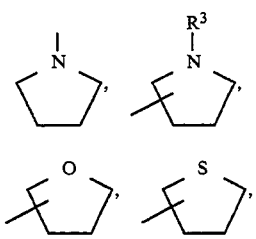

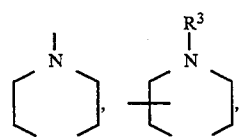

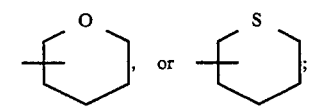

wherein:
M is —$NR^3$, —O—, —S— or —$CH_2$—
X and Y are each independently:
 (1) hydrogen,
 (2) hydroxy,
 (3) halogen,
 (4) trifluoromethyl,
 (5) $C_{1-10}$alkyl,
 (6) aryl substituted with $X^1$ and $Y^1$,
 (7) $R^2O$—,
 (8) arylcarbonyloxy-, wherein aryl is substituted with $X^1$ and $Y^1$,
 (9) $R^3$—C(O)—O—,
 (10) —$CO_2R^2$,
 (11) —$CO_2H$, or
 (12) nitro;
$X^1$ and $Y^1$ are each independently:
 (1) hydrogen,
 (2) hydroxy,
 (3) halogen,
 (4) trifluoromethyl,
 (5) $C_{1-4}$alkyl,
 (6) $R^2O$—,
 (7) $R^3$—C(O)—O—,
 (8) —$CO_2R^2$,
 (10) —$CO_2H$, or
 (11) nitro;
each $X^2$ is independently:
 (1) halogen,
 (2) hydroxy,
 (3) $R^3R^3N$—,
 (4) $R^2O$—,
 (5) $R^2O$—C(O)—,
 (6) $R^3$—C(O)—O—, (7) oxo,
(8) $C_{3-10}$cycloalkyl-,
(9) aryl substituted with X and Y,
(10) —$CO_2H$,
(11) vinylidene,
(12) $R^3$—C(O)—,
(13) $R^2O$—C(O)—O—, or
(14) $R^2O$—C(O)—$NR^3$—;

each $X^3$ is independently:
(1) halogen,
(2) hydroxy,
(3) $R^3R^3N$—,
(4) $R^2O$—,
(5) $R^2O$—C(O)—,
(6) $R^3$—C(O)—O—,
(7) oxo,
(8) $C_{3-10}$cycloalkyl,
(9) aryl substituted with X and Y,
(10) heteroaryl substituted with X and Y,
(11) heterocycloalkyl,
(12) aryl $S(O)_n$, wherein aryl is substituted with X and Y,
(13) $R^3$—C(O)—$NR^3$—,
(14) $R^3R^3N$—C(O)—,
(15) —$CO_2H$,
(16) -vinylidene,
(17) $R^3$—C(O)—,
(18) $R^2O$—C(O)—O—,
(19) $R^3R^3NC(O)$—O—, or
(20) $R^2O$—C(O)—$NR^3$—;

n is 0, 1 or 2;

$Z^1$ and $Z^2$ are each independently:
(1) —$OR^6$,
(2) —$SR^6$, or
(3) —$NR^6R^6$;

or a pharmaceutically acceptable salt of formula (I).

In a first subclass of this embodiment are the compounds of formula (I), with subgeneric formula (III) and wherein $R^5$, $R^6$ and R are selected from the group described in Table 1 below:

TABLE 1

(III)

| Compound No. | $R^5$ | $R^6$ | R |
|---|---|---|---|
| 100 | H | H | —$CH_2OH$ |
| 101 | —$CH_2(C_6H_5)$ | H | —$CH_2OH$ |
| 102 | —$CH_2(C_6H_5)$ | —$CH_2(C_6H_5)$ | —$CH_2OH$ |
| 103 | —$CH_3$ | H | —$CH_2OH$ |
| 104 | —$CH_3$ | —$CH_3$ | —$CH_2OH$ |
| 105 | H | —$CH_3$ | —$CH_2OH$ |
| 106 | —$CH_3$ | —$CH_3$ | —$CH_2OCH_3$ |
| 107 | H | —$CH_3$ | —$CH_2OCH_3$ |
| 108 | H | H | —$CH_2OCH_2C_6H_5$ |
| 109 | H | H | —$CH_2OCH_3$ |

In a second subclass of this invention are the compounds of formula (I), with subgeneric formula (IV) and wherein $R^5$, $R^6$ and R are selected from the group described in Table 2 below:

TABLE 2

(IV)

| Compound No. | $R^5$ | $R^6$ | R |
|---|---|---|---|
| 110 | H | H | —$C(CH_3)_2(OH)$ |
| 111 | H | H | —$CH(OH)(CH_2)_3CH_3$ |
| 112 | H | H | —$C(OH)(CH_2CH_2CH_2CH_3)_2$ |
| 113 | H | H | —$CH(OAc)(CH_2)_3CH_3$ |
| 114 | H | H | —$CH(OH)(CH_3)$ |
| 115 | H | H | —$C(OH)(CH_2CH_3)_2$ |
| 116 | H | H | —$C(OH)(C_6H_5)_2$ |
| 117 | H | H | —$C(OH)(CH_2CH_2CH_3)_2$ |
| 118 | H | H | —$C(OH)(CH_2CH_2C_6H_5)_2$ |
| 119 | H | H | —$C(O)CH_3$ |
| 120 | H | H | —$C(O)(CH_2)_3CH_3$ |
| 121 | H | H | —$C(O)CH_2OH$ |
| 122 | H | H | —$C(O)(2\text{-}CH_3\text{—}C_6H_4)$ |
| 123 | H | H | —$C(O)$—$C_6H_5$ |
| 124 | H | H | —$C(O)(CH_2)_2CH_3$ |
| 125 | H | H | —$C(O)(CH_2)_2CH_3$ |
| 126 | H | H | —$C(O)CH_2CH_3$ |
| 127 | H | H | —$C(O)(CH_2)_2C_6H_5$ |

In the third subclass of this embodiment are the compounds of formula (I), with subgeneric formula (V) and wherein $R^5$, $R^6$ and R are selected from the group described in Table 3 below:

TABLE 3

(V)

| Compound No. | $R^5$ | $R^6$ | R |
|---|---|---|---|
| 128 | H | H | —$CH_3$ |
| 129 | H | H | —$CH_2F$ |
| 130 | H | H | —$CHF_2$ |
| 231 | H | H | -vinyl |
| 232 | H | H | -butenyl |

In a fourth subclass of this embodiment is the compounds of formula (I), with subgeneric formula (VI) and wherein $R^4$—$(A)_a$, $R^6$, and R are selected from the group described in Table 4 below:

TABLE 4

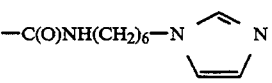

(VI)

| Compound No. | R⁴—(A)ₐ— | R⁶ | R |
|---|---|---|---|
| 131 | $-C(O)NH(CH_2)_{11}CH_3$ | H | $-C(OH)(CH_2CH_2CH_2CH_3)_2$ |
| 132 | $-(CH_2)_{13}CH_3$ | H | $-C(OH)(CH_3)_2$ |
| 133 | $-C(O)-NH-CH(CH_3)_2$ | H | $-CH_2OH$ |
| 134 | $-C(O)-NH-(CH_2)_{11}CH_3$ | H | $-C(O)CH_2CH_2CH_2CH_3$ |
| 135 | $-C(O)-NH(CH_2)_9CH_3$ | H | $-C(O)CH_3$ |
| 136 | $-(CH_2)_{13}CH_3$ | H | $-C(O)CH_3$ |
| 140 | $-C(O)-NH(CH_2)_4CHO$ | H | $-C(O)CH_3$ |
| 137 | $-C(O)-NH(CH_2)_6OH$ | H | $-C(O)CH_3$ |
| 138 | $-C(O)NH(CH_2)_{11}CH_3$ | H | $-C(O)CH_3$ |
| 139 | $-C(O)-NH(CH_2)_{11}O-C_6H_5$ | H | $-C(O)CH_3$ |
| 141 | $-C(O)NH(CH_2)_6-$ imidazolyl | H | $-C(O)CH_3$ |
| 142 | $-C(O)NH(CH_2)_6-$ morpholinyl | H | $-C(O)CH_3$ |
| 143 | $-C(O)NH(CH_2)_3-$ imidazolyl | H | $-C(O)CH_3$ |
| 144 | $-C(O)NH(CH_2)_3-$ morpholinyl | H | $-C(O)CH_3$ |
| 145 | $-C(O)-NH(CH_2)6NH_2$ | H | $-C(O)CH_3$ |
| 146 | $-C(O)-(CH2)_{12}CH_3$ | H | $-C(O)CH_3$ |

In a fifth subclass of this embodiment are the compounds of formula (I) with subgeneric formula (VII) and wherein R, $Z^1$ and $Z^2$ are as described below:

TABLE 5

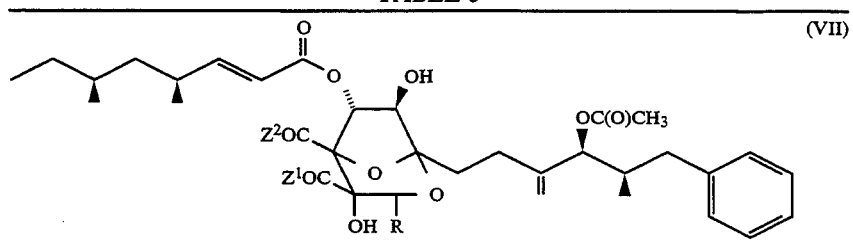

(VII)

| Compound No. | R | $Z^1$ | $Z^2$ |
|---|---|---|---|
| 147 | $-CH_3$ | $-OCH_2CH_2OCH_3$ | $-OH$ |
| 148 | $-CH_3$ | $-OCH_2OC(O)C(CH_3)_3$ | $-OH$ |
| 149 | $-CH_3$ | $-OCH_2OC(O)C(CH_3)_3$ | $-OCH_2OC(O)C(CH_3)_3$ |
| 150 | $-CH_3$ | $-OCH_3$ | $-OH$ |
| 151 | $-CH_3$ | $-OH$ | $-OCH_3$ |
| 152 | $-CH_3$ | $-OCH_2C(O)N(CH_3)_2$ | $-OH$ |
| 153 | $-CH_3$ | $-OH$ | $-OCH_2C(O)N(CH_3)_2$ |
| 154 | $-CH_3$ | $-OCH_2OC(O)CH_3$ | $-OH$ |
| 155 | $-CH_3$ | $-OCH_2OC(O)CH_3$ | $-OCH_2OC(O)CH_3$ |
| 156 | $-CH_2F$ | $-OCH_2OC(O)C(CH_3)_3$ | $-OH$ |
| 157 | $-CH_3$ | $-OCH(CH_3)OC(O)OCH_2CH_3$ | $-OH$ |
| 158 | $-CH_3$ | $-OCH(CH_3)OC(O)C(CH_3)_3$ | $-OH$ |
| 174 | $-C(O)CH_3$ | $-OCH_3$ | $-OH$ |
| 175 | $-C(O)CH_3$ | $-OH$ | $-OCH_3$ |
| 176 | $-C(O)CH_3$ | $-OCH_2OC(O)C(CH_3)_3$ | $-OH$ |

TABLE 5-continued (VII)

| Compound No. | R | $Z^1$ | $Z^2$ |
|---|---|---|---|
| 177 | —C(O)CH$_3$ | —OH | —OCH$_2$OC(O)C(CH$_3$)$_3$ |
| 178 | —C(O)CH$_3$ | —OCH$_2$OC(O)CH$_3$ | —OH |
| 179 | —C(O)CH$_3$ | —OH | —OCH$_2$OC(O)CH$_3$ |
| 180 | —C(O)CH$_3$ | —OCH$_2$OC(O)CH$_3$ | —OCH$_2$OC(O)CH$_3$ |
| 181 | —C(O)CH$_3$ | —OCH$_3$ | —OCH$_3$ |
| 182 | —C(O)CH$_3$ | —OCH$_2$C(O)OC(CH$_3$)$_3$ | —OH |
| 183 | —C(O)CH$_3$ | —O(CH$_2$)$_2$CH(CH$_3$)$_2$ | —OH |
| 159 | —CH$_3$ | (phthalide-O-) | —OH |
| 160 | —CH$_2$F | —OCH$_2$OC(O)C(CH$_3$)$_3$ | —OCH$_2$OC(O)C(CH$_3$)$_3$ |
| 170 | —CH$_3$ | —OCH(CH$_3$)OC(O)C(CH$_3$)$_3$ | —OCH(CH$_3$)OC(O)C(CH$_3$)$_3$ |
| 171 | —CH$_3$ | —OCH$_2$-C(=C(CH$_3$)-O-C(O)-O-) | —OH |
| 172 | —CH$_3$ | —OH | —OCH$_2$-C(=C(CH$_3$)-O-C(O)-O-) |
| 173 | —CH$_3$ | —OCH$_2$-C(=C(CH$_3$)-O-C(O)-O-) | —OCH$_2$-C(=C(CH$_3$)-O-C(O)-O-) |

A related subclass are compounds of structural formula (VIII) wherein R, R$^1$, Z$^1$, and R$^4$(A)$_a$-are described below:

TABLE 6

(VIII)

| R | R$^1$ | R$^4$(A)$_a$—O | Z$^1$ |
|---|---|---|---|
| —CH$_3$ | aa | cc | OH |
| —CH$_3$ | aa | cc | O—CH$_2$OC-t-Bu | aa = (3-phenyl-prop-2-enyl)-CH(CH$_3$)-CH(OH)-CH$_2$-CH(CH$_3$)- bb = -CH$_2$-CH$_2$-CH(OAc)-CH(CH$_3$)-CH$_2$-phenyl cc = -C(O)-(CH$_2$)$_n$-CH=CH-CH$_2$-CH=CH-...

dd = -C(O)-(CH$_2$)$_2$-CH=CH-CH$_2$-CH(CH$_3$)-CH$_2$-CH$_2$-phenyl

TABLE 6-continued

| | | | |
|---|---|---|---|
| —CH3 | aa | cc | |

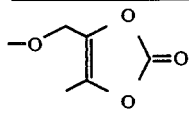

| —CH3 | bb | dd | —OH |
| —CH3 | bb | dd | —OCH2OC-t-Bu |

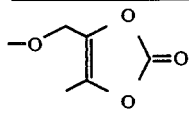

| —C(O)CH3 | aa | cc | —OH |
| —C(O)CH3 | aa | cc | —OCH2OC-t-Bu |

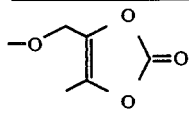

| —C(O)CH3 | aa | cc | |

| —C(O)CH3 | bb | dd | —OH |
| —C(O)CH3 | bb | dd | —OCH2O—C-t-Bu |

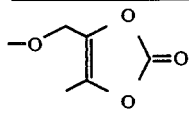

| —C(O)CH3 | bb | dd | |

| —CH2OH | aa | cc | —OH |
| —CH2OH | aa | cc | —OCH2O—C-t-Bu |

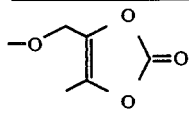

| —CH2OH | aa | cc | |

| —CH2OH | bb | dd | —OH |
| —CH2OH | bb | dd | —OCH2O—C-t-Bu |

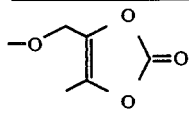

| —CH2OH | bb | dd | |

In a sixth subclass of this embodiment are compounds of formula (I) with subgeneric formula (IX) and wherein $R^1$, R, and $R^4$—$(A)_a$ are as described below.

TABLE 7

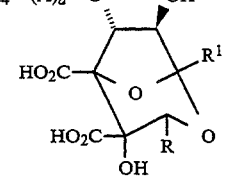
(IX)

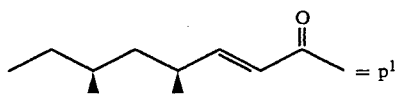 = p¹

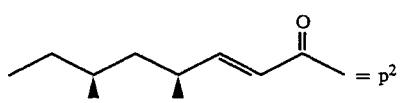 = p²

| Compound No | R1 | R— | $R^4$—$(A)_a$— |
|---|---|---|---|
| 184 | —(CH2)2CH(CH3)CH2CH(CH3)CH2C6H5 | —C(O)(CH2)3CH3 | p² |
| 185 | —(CH2)2CH(CH3)CH(OAc)CH(CH3)CH2C6H5 | —C(O)(CH2)3CH3 | p² |

Except where specifically defined to the contrary, the terms alkyl, alkenyl, alkynyl, alkoxy and acyl include both the straight-chain and branched chain species of the term. The term cycloalkyl includes both monocyclic and polycyclic species. Where two Markush groups are bonded to the same atom, e.g. $R^3R^3N$, these groups may take on the same value e.g. $(CH_3)_2N$ or different values within the Markush group, e.g. $CH_3NH$. Similarly each Markush group, such as $R^3$, within a compound of formula (I) is selected independently, e.g. $R^3R^3N$— may be $NH_2$ while $R^3$—C(O)—O— is $CH_3$—C(O)—O—.

Suitable starting materials for the compounds of the present invention are compounds of structural formula (II).

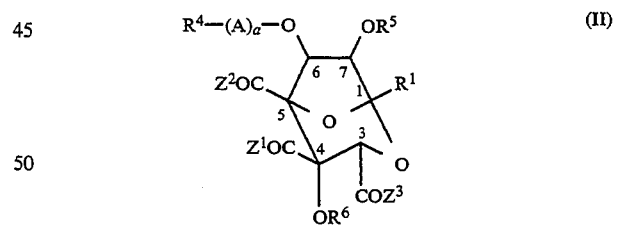
(II)

wherein:
a is 0 or 1;
A is —C(O)—, —$NR^3$—C(O)—, or —OC(O)—;
$R^1$ is:
(1) $C_{1-20}$alkyl,
(2) substituted $C_{1-20}$alkyl wherein one or more of the carbons is substituted with $X^3$,
(3) $C_{1-20}$alkyl wherein one or more of the carbons is replaced by —$NR^3$—, —O—, or —S(O)$_n$—,
(4) substituted $C_{1-20}$alkyl wherein one or more of the carbons is replaced by —$NR^3$—, —O— or —S(O)$_n$— and wherein one or more of the carbon atoms is substituted with $X^3$,
(5) aryl substituted with X and Y,
(6) heteroaryl substituted with X and Y, (7) $C_{2-20}$alkenyl wherein alkenyl contains one or more double bonds,
(8) substituted $C_{2-20}$alkenyl wherein alkenyl contains one or more double bonds and wherein one or more of the carbons is substituted with $X^3$,
(9) $C_{2-20}$alkenyl wherein alkenyl contains one or more double bonds and one or more of the nonolefinic carbons is replaced by —$NR^3$—, —O— or —$S(O)_n$—,
(10) substituted $C_{2-20}$alkenyl wherein alkenyl contains one or more double bonds and one or more of the nonolefinic carbons is replaced by —$NR^3$—, —O— or —$S(O)_n$— and wherein one or more of the carbons is substituted with $X^3$,
(11) $C_{3-10}$cycloalkyl, or
(12) substituted $C_{3-10}$cycloalkyl in which one or more of the carbon atoms is substituted with:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) aryl$S(O)_n$, wherein aryl is substituted with X and Y,
 (m) $R^3$—C(O)—$NR^3$—,
 (n) $R^3R^3N$—C(O)—,
 (o) $C_{1-10}$alkyl$S(O)_n$—,
 (p) $C_{1-10}$alkyl,
 (q) —$CO_2H$,
 (r) -vinylidene,
 (s) $R^3$—C(O)—,
 (t) $R^2O$—C(O)—O—,
 (u) $R^3R^3N$—C(O)—O—, or
 (v) $R^2O$—C(O)—$NR^3$—;
each $R^2$ is independently:
 (1) $C_{1-10}$alkyl,
 (2) aryl substituted with X and Y;
 (3) aryl$C_{1-4}$alkyl wherein aryl is substituted with X and Y,
 (4) heteroaryl wherein heteroaryl is substituted with X and Y,
 (5) heteroaryl$C_{1-4}$alkyl- wherein heteroaryl is substituted with X and Y,
 (6) heterocycloalkyl$C_{1-4}$alkyl-,
 (7) $C_{2-10}$alkenyl,
 (8) aryl$C_{2-10}$alkenyl wherein aryl is substituted with X and Y, or
 (9) $C_{3-10}$alkynyl;
each $R^3$ is independently:
 (1) $C_{1-10}$alkyl,
 (2) aryl substituted with X and Y,
 (3) aryl$C_{1-4}$alkyl wherein aryl is substituted with X and Y,
 (4) heteroaryl wherein heteroaryl is substituted with X and Y,
 (5) heteroaryl$C_{1-4}$alkyl- wherein heteroaryl is substituted with X and Y,
 (6) heterocycloalkyl$C_{1-4}$alkyl-,
 (7) $C_{2-10}$alkenyl,
 (8) aryl$C_{2-10}$alkenyl wherein aryl is substituted with X and Y,
 (9) $C_{3-10}$alkynyl,
 (10) hydrogen, or
 (11) $C_{1-5}$alkyl substituted with $X^1$;
$R^4$ is:
 (1) $C_{1-20}$alkyl,
 (2) substituted $C_{1-20}$alkyl in which one or more carbon atoms is substituted with $X^3$,
 (3) $C_{1-20}$alkyl wherein one or more of the carbons is replaced by —$NR_3$—, —O—, or —$S(O)_n$—,
 (4) substituted $C_{1-20}$alkyl wherein one or more of the carbons is replaced by —$NR^3$—, —O— or —$S(O)_n$— and wherein one or more carbon atoms is substituted with $X^3$,
 (5) aryl substituted with X and Y,
 (6) heteroaryl substituted with X and Y,
 (7) $C_{2-20}$alkenyl wherein alkenyl contains one or more double bonds,
 (8) substituted $C_{2-20}$alkenyl wherein alkenyl contains one or more double bonds and wherein one or more of the carbons is substituted with $X^3$,
 (9) $C_{2-20}$alkenyl wherein alkenyl contains one or more double bonds and one or more of the nonolefinic carbons is replaced by —$NR^3$—, —O— or —$S(O)_n$—,
 (10) substituted $C_{2-20}$alkenyl wherein alkenyl contains one or more double bonds and one or more of the nonolefinic carbons is replaced by —$NR^3$—, —O— or —$S(O)_n$— and wherein one or more of the carbon atoms is substituted with $X^3$,
 (11) $C_{3-10}$cycloalkyl,
 (12) substituted $C_{3-10}$cycloalkyl in which one or more of the carbon atoms is substituted with $X^3$, or
 (13) hydrogen;
$R^5$ is:
 (1) hydrogen,
 (2) $C_{1-10}$alkyl,
 (3) aryl substituted with X and Y,
 (4) aryl$C_{1-4}$alkyl, wherein aryl is substituted with X and Y,
 (5) $R^2O$—C(O)—,
 (6) $C_{3-10}$cycloalkyl,
 (7) $R^3$—C(O)—, or
 (8) $R^3R^3N$—C(O)—;
each $R^6$ is independently:
 (1) $C_{1-20}$alkyl,
 (2) substituted $C_{1-20}$alkyl in which one or more of the carbon atoms is substituted with $X^3$,
 (3) $C_{1-20}$alkyl wherein one or more of the carbons is replaced by —$NR^3$—, —O—, or —$S(O)_n$—,
 (4) substituted $C_{1-20}$alkyl wherein one or more of the carbons is replaced by —$NR^3$—, —O— or —$S(O)_n$— and wherein one or more of the carbon atoms is substituted with $X^3$,
 (5) $C_{2-20}$alkenyl wherein alkenyl contains one or more double bonds,
 (6) substituted $C_{2-20}$alkenyl wherein alkenyl contains one or more double bonds and wherein one or more of the carbons is substituted with:
  (a) halogen
  (b) hydroxy,
  (c) $R^3R^3N$—,
  (d) $R^2O$—,
  (e) $R^2O$—C(O)—,
  (f) $R^3$—C(O)—O—,
  (g) oxo,
  (h) $C_{3-10}$cycloalkyl,
  (i) aryl substituted with X and Y,
  (j) heteroaryl substituted with X and Y,
  (k) heterocycloalkyl, (l) aryl S(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—,
(t) R$^2$O—C(O)—NR$^3$— or
(u) —OC(O)O—, which forms a five-membered ring:

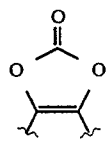

with adjacent olefinic carbons,
(7) C$_{2-20}$alkenyl wherein alkenyl contains one or more double bonds and one or more of the nonolefinic carbons is replaced by —NR$^3$—, —O— or —S(O)$_n$—,
(8) substituted C$_{2-20}$alkenyl wherein alkenyl contains one or more double bonds and one or more of the nonolefinic carbons is replaced by —NR$^3$—, —O— or —S(O)$_n$— and wherein one or more of the carbon atoms is substituted with:
(a) halogen
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—,
(t) R$^2$O—C(O)—NR$^3$—, or
(u) —OC(O)O—, which forms a five-membered ring:

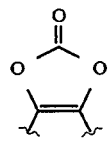

with adjacent olefinic carbons,
(9) C$_{2-20}$alkynyl wherein alkynyl contains one or more triple bonds,
(10) substituted C$_{2-20}$alkynyl wherein alkynyl contains one or more triple bonds and wherein one or more of the carbons is substituted with X$^3$,
(11) C$_{2-20}$alkynyl wherein alkynyl contains one or more triple bonds and one or more of the saturated carbons is replaced by —NR$^3$—, —O— or —S(O)$_n$—,
(12) substituted C$_{2-20}$alkynyl wherein alkynyl contains one or more double bonds and one or more of the saturated carbons is replaced by —NR$^3$—, —O— or —S(O)$_n$— and wherein one or more of the carbon atoms is substituted with X$^3$,
(13) aryl substituted with X and Y,
(14) heteroaryl substituted with X and Y,
(15) C$_{3-5}$ cycloalkyl,
(16) substituted C$_{3-5}$ cycloalkyl in which one or more of the carbon atoms is substituted with:
(a) R$^3$O—, or
(b) R$^3$R$^3$N—, or
(17) hydrogen;
aryl including X, Y substitution is:

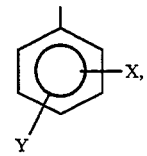

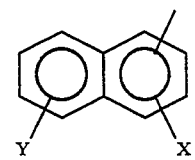

or

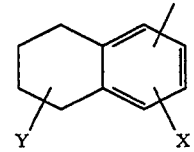

heteroaryl including X, Y substitution is

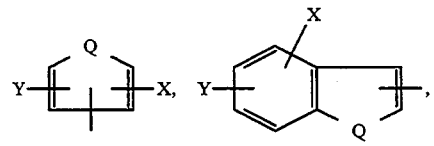

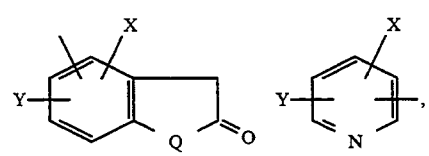

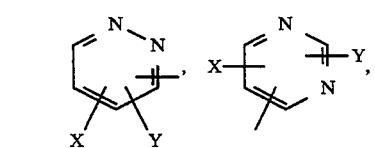

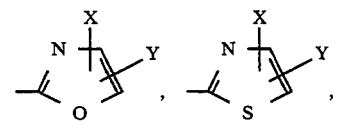

-continued

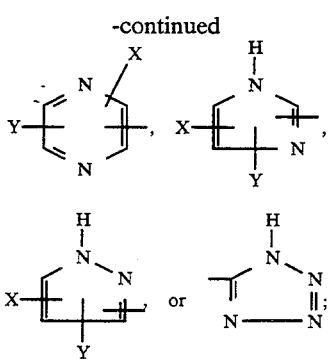

wherein:
Q is —NR³, —O— or —S—;
heterocycloalkyl is:

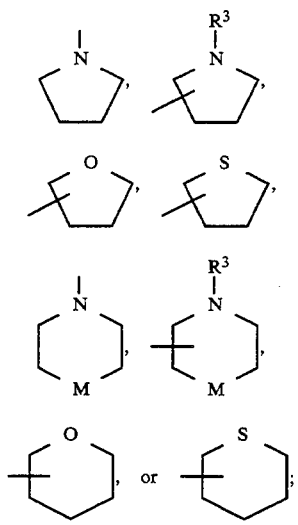

wherein:
M is —NR³, —O—, —S— or —CH₂—
X and Y are each independently:
(1) hydrogen,
(2) hydroxy,
(3) halogen,
(4) trifluoromethyl,
(5) $C_{1-10}$alkyl,
(6) aryl substituted with $X^1$ and $Y^1$,
(7) R²O—,
(8) arylcarbonyloxy-, wherein aryl is substituted with $X^1$ and $Y^1$,
(9) R³—C(O)—O—,
(10) —CO₂R²,
(11) —CO₂H, or
(12) nitro;
$X^1$ and $Y^1$ are each independently:
(1) hydrogen,
(2) hydroxy,
(3) halogen,
(4) trifluoromethyl,
(5) $C_{1-4}$alkyl,
(6) R²O—,
(7) R³—C(O)—O—,
(8) —CO₂R²,
(9) —CO₂H, or
(10) nitro;
each $X^3$ is independently:
(1) halogen,
(2) hydroxy,
(3) R³R³N—,
(4) R²O—,
(5) R²O—C(O)—,
(6) R³—C(O)—O—,
(7) oxo,
(8) $C_{3-10}$cycloalkyl,
(9) aryl substituted with X and Y,
(10) heteroaryl substituted with X and Y,
(11) heterocycloalkyl,
(12) aryl S(O)$_n$, wherein aryl is substituted with X and Y,
(13) R³—C(O)—NR³—,
(14) R³R³N—C(O)—,
(15) —CO₂H,
(16) -vinylidene,
(17) R³—C(O)—,
(18) R²O—C(O)—O—,
(19) R³R³NOC(O)—O—, or
(20) R²O—C(O)—NR³—;
n is 0, 1 or 2;
$Z^1$, $Z^2$ and $Z^3$ are each independently:
(1) —OR⁶,
(2) —SR⁶, or
(3) —NR⁶R⁶;
or a pharmaceutically acceptable salt.

The compounds of formula (II) can be prepared from (1S,3S,4S,5R,6R,7R)-1-[(4S)-acetoxy-3-methylene-5-methyl-6-phenyl]hexyl-4,6,7-trihydroxy-6-O-(4,6-dimethyl-2-octenoyl)-2,8-dioxabicyclo[3.2.1]octane-3,4,5-tricarboxylic acid, hereafter referred to as Compound IIA, (1S,3S,4S,5R,6R,7R)-1-[4-hydroxy-3,5-dimethyl-8-phenyl]oct-7-enyl-4,6,7-trihydroxy-6-O-(tetradeca-6,12-dienoyl)-2,8 -dioxabicyclo[3.2.1]octane 3,4,5-tricarboxylic acid, hereafter referred to as Compound IIB and (1S,3S,4S,5R,6R,7R)-1-[4-acetoxy-5-methyl-6-phenyl]hexyl-4,6,7-trihydroxy-6-O-(6-methyl-9-phenyl-4-nonenoyl)-2,8-dioxabicyclo[3.2.1]octane-3,4,5-tricarboxylic acid, hereafter referred to as Compound IIC, according to sequences and the detailed description described in EP 0 512 865 A2. Intermediates formed in the process of making the compounds of this invention are named as derivatives of Compounds IIA, IIB, and IIC. For example, the 3-t-butyl ester of compound IIA is named IIA-3-t-butyl ester. The preparation of Compounds IIA, IIB, and IIC have been described in U.S. Pat. No. 5,053,425, EP Publication No. 0 448 393 and U.S. Pat. No. 5,026,554, respectively.

The compounds of structural formula (III) are made according to the procedures in Scheme 1, as described in Examples 1 to 8 and the description below:

The compound of formula (II) is converted to its 3-benzyl ester by Fisher esterification with benzyl alcohol and HCl. Treatment of the 3-benzyl ester with t-butyl-O-N,N'-dialkyisourea in solvents such as methylene chloride, benzene or tetrahydrofuran gives the 3-benzyl-4,5-di-t-butyl ester. The C-3 benzyl group is removed selectively by transfer hydrogenolysis with Pd/C and methyl cyclohexadiene in methanol. Alternatively, the C-7 position may be protected with standard alcohol protecting groups such as 1-methyl-1-methoxyethyl ether and followed by removal of the C-3 benzyl group. The liberated free C-3 carboxylic acid group may be reduced to an alcohol by forming its mixed anhydride followed by sodium borohydride reduction. The resulting alcohol may then be modified to various ethers by using a base such as NaH followed by the appropriate halide. The other alcohols at positions C-4 and C-7 may also be converted to ethers in a similar manner. The protecting t-butyl groups are removed by stirring the compounds with trifluoroacetic acid in methylene chloride.

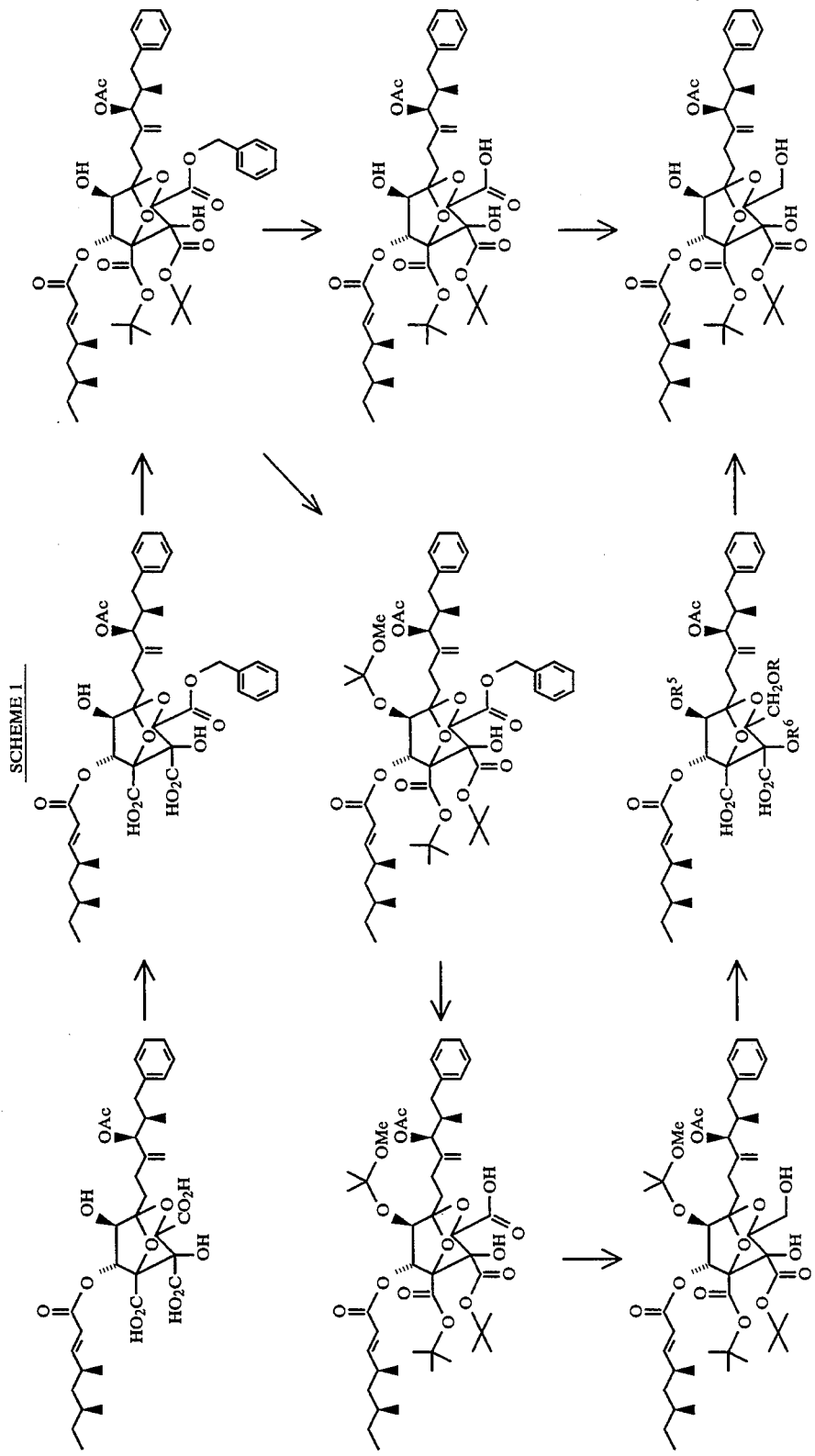

The above described procedure may be analogously applied to any appropriately protected starting material of Formula (II).

The compounds of structural formula (IV) are prepared according to the procedures in Schemes 2 and 3 as described in Examples 4 through 23 and the description below:

In the first method, the C3-carboxylic acid group of the IIA-4,5-di-t-butyl ester starting material described above is converted to a mixed anhydride or acyl halide by using reagents such as n-methyl morpholine/isobutyl chloroformate or thionyl chloride and then treated with Grignard reagents to form ketones and alcohols or diazo reagents to form diazoketones. The ketones obtained as such could be reduced with reducing agents such as sodium borohydride and the diazaketones could be hydrolyzed to hydroxy ketones. In a second method to modify the C-3 carboxylic acid groups, the IIA-3,4,5-tri-butyl ester is treated with alkyl cerium salts to form the corresponding IIA-4'-hydroxy-4,5-di-t-butyl ester-3-alkyl ketones. The C4' position could be modified as desired. For example, C4'-hydroxy group of IIA-4'-hydroxy-4,5-di-t-butyl ester-3-alkyl ketones may be acylated with a base such as triethylmaine and acylating agent such as acetic anhydride. The IIA-4,5-di-t-butyl ester-3-alkyl ketones may be deprotected with trifluoracetic acid in methylene chloride. The ketones obtained as such may also be reduced and then deprotected or reduced, esterified and deprotected with to yield the corresponding C3-ketone, C3-alcohol or C3-ester derivatives of formula (I). C3-carboxylic acid groups of IIB or IIC or their analogs are modified to the corresponding ketones, alcohols and esters in a similar manner.

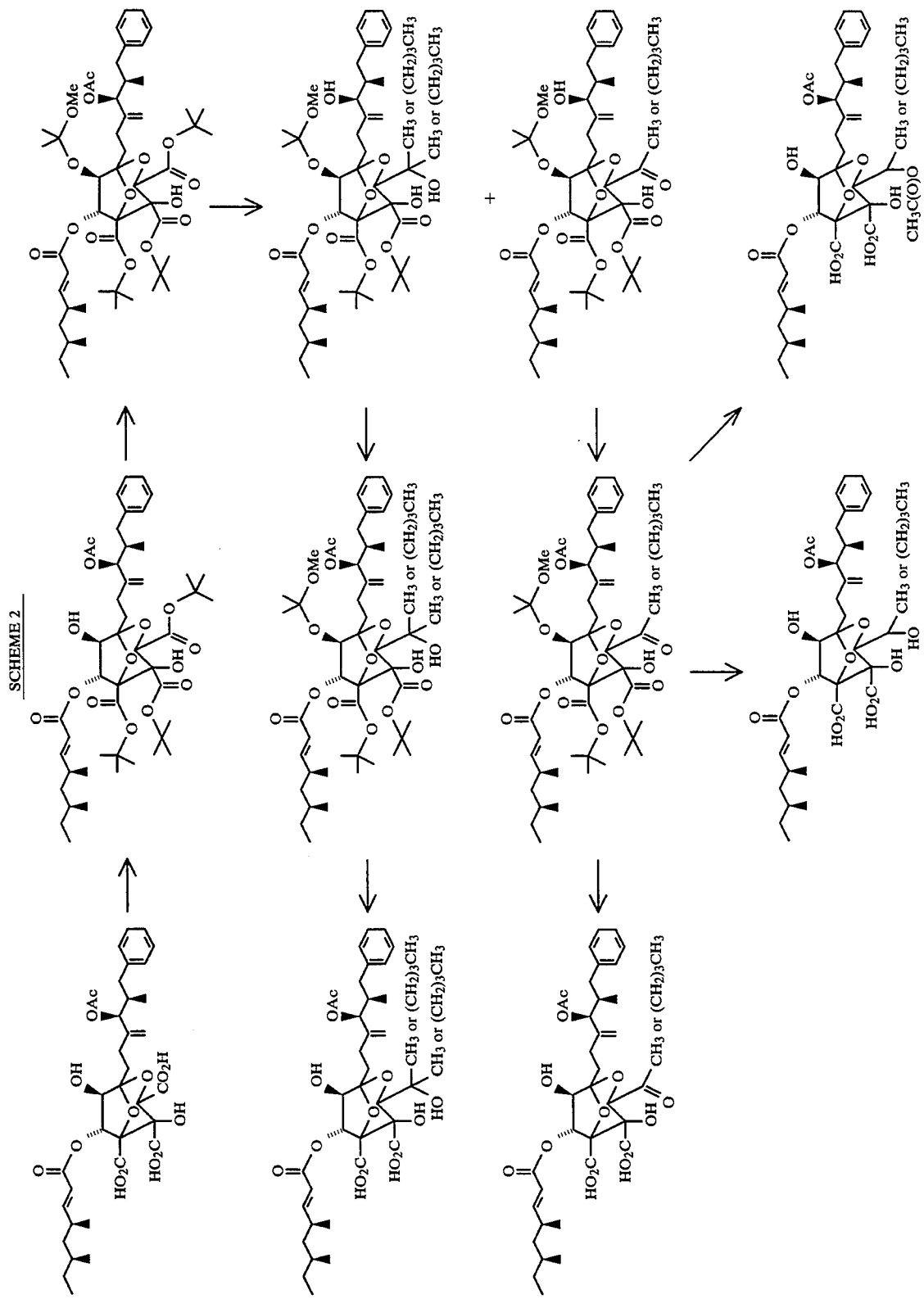
SCHEME 2

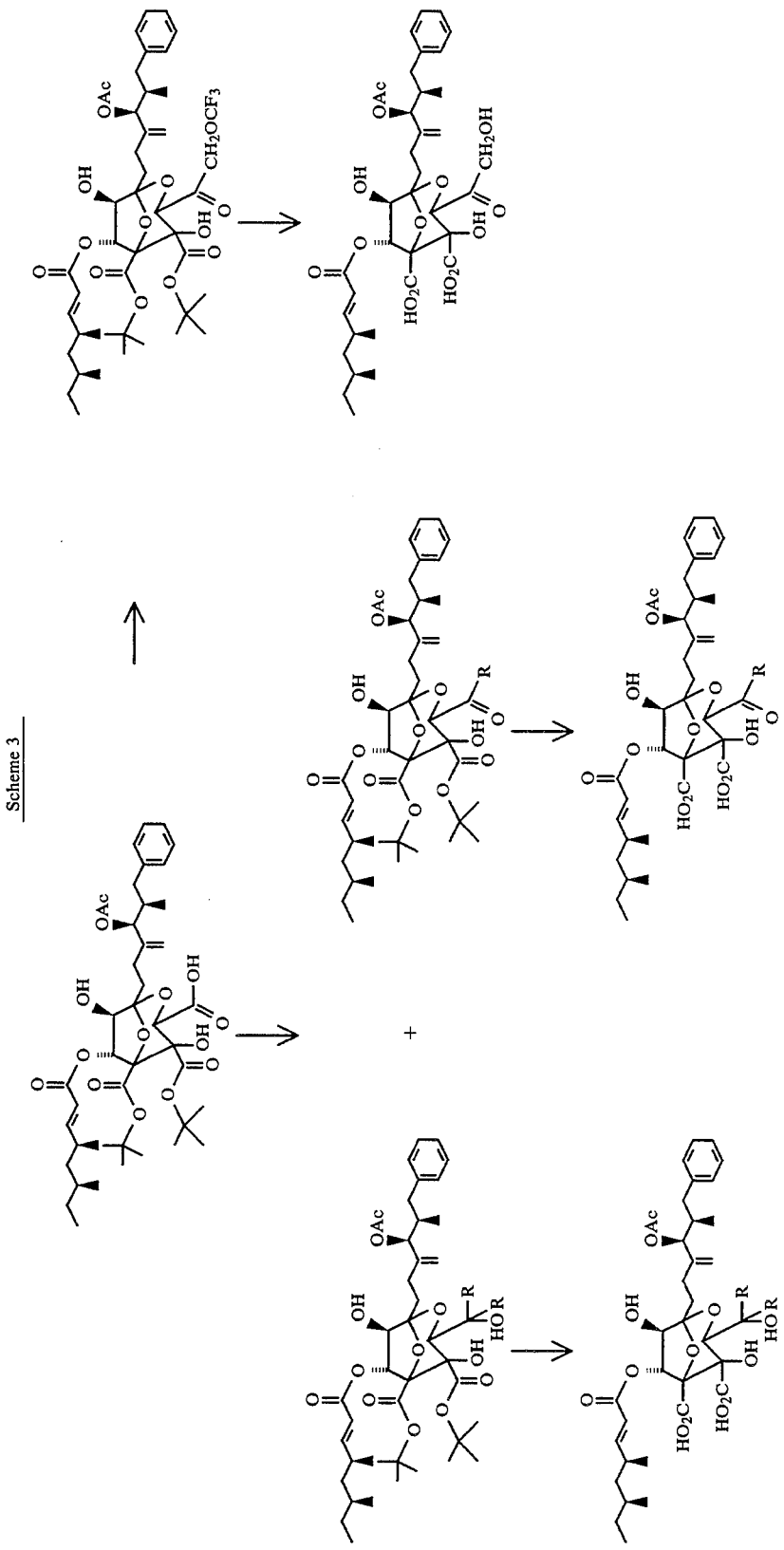

The compounds of Table 3 were prepared according to the procedures of Scheme 4, Examples 24 to 28, and the description below.

C7-protected IIA-3-hydroxymethyl-4,5-di-t-butyl ester is converted to the corresponding IIA-C3-alkyl, alkenyl, fluoromethyl or difluoromethyl derivatives as follows. C7-protected IIA-3-hydroxymethyl-4,5-di-t-butyl ester is converted to IIA-C3-fluoromethyl derivative by treatment with fluorinating agents such as DAST (diethylaminosulfur trifloride). The IIA-C3-difluoromethyl derivative is formed by oxidation of the IIA-hydroxymethyl group to IIA-C3-aldehyde followed by treatment of the resulting aldehyde with DAST. The IIA-C3-aldehyde may also be treated with appropriate Wittig reagent to form the desired IIA-C3-alkenyl derivatives. In order to deoxygenate the C3-hydroxy methyl group, IIA-3-hydroxymethyl is transformed to its C3-xanthate by treatment with carbon disulfide and halides such as methyl iodide and then reductively deoxygenated with tri-butyl tin hydride.

The above method may also be applied to C7-protected IIB-3-hydroxymethyl-4,5-di-t-butyl ester C7-protected IIB-3-hydroxymethyl-4,5-di-t-butyl ester or similar derivatives.

The compounds of structural formula (VI) were prepared according to the procedures in Scheme 5 described in Examples 29–42 and in the following description:

General Deacylation Reactions

To a mixture of C3 modified IIA-3,4-di-t-butyl ester (10 mmol) and NaOAc.3H$_2$O (30 g, 220 mmol) in methanol (100 mL) is added hydroxylamine hydrochloride (6.95 g, 100 mmol). The reaction is stirred at ambient temperature for 20 h, filtered and concentrated to dryness. The residue is

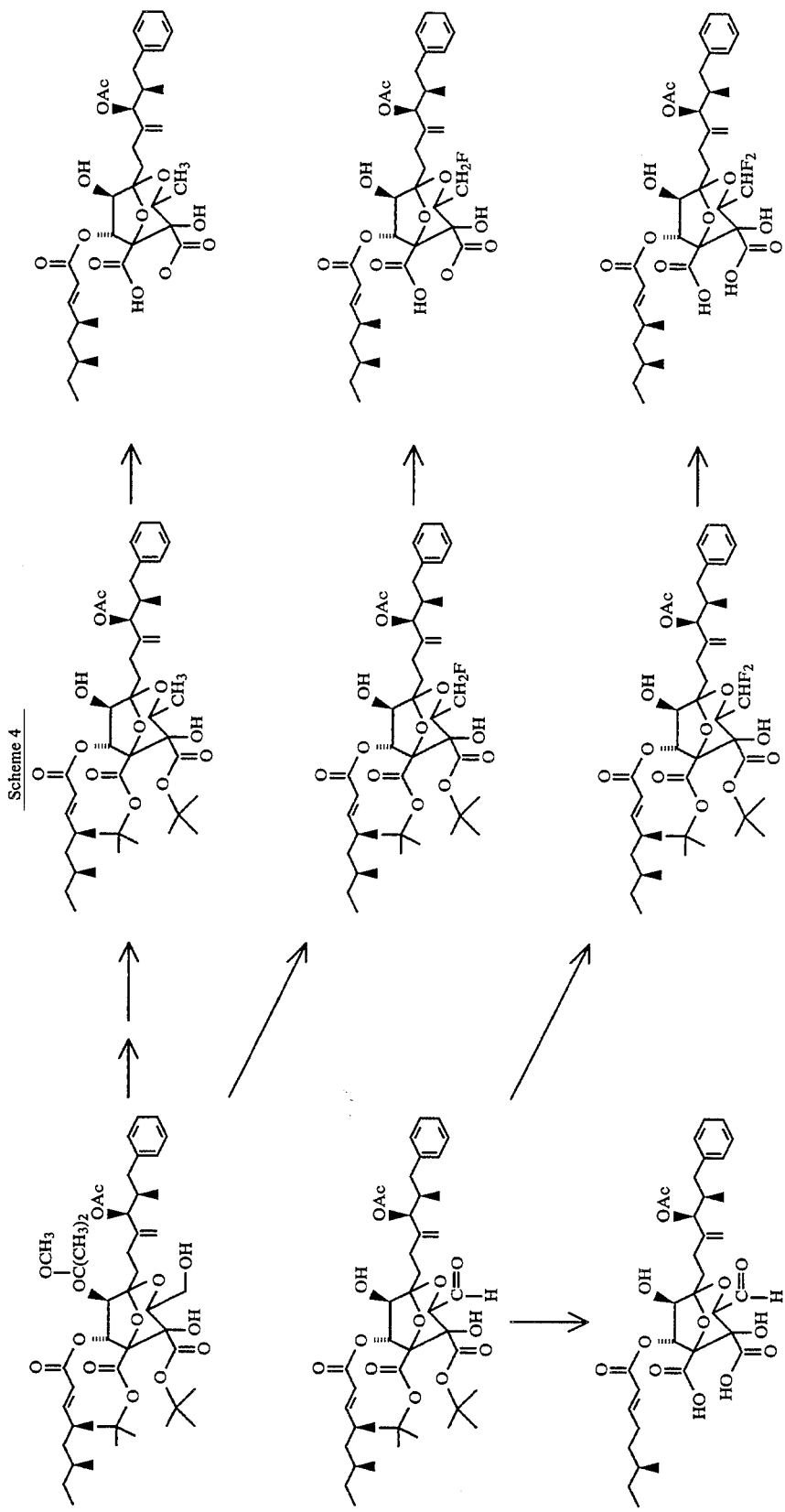

partitioned between Et$_2$O and brine and the organic layer is dried (Na$_2$SO$_4$), filtered and the filtrate is concentrated in vacuo. The residue is purified by column chromatography (silica gel, 2:1 hexane/EtOAc) to afford the C6 deacylated IIA-di-t-butyl ester.

General Procedure for Preparation of C6 Carbamates, Method A

The appropriate isocyanate E0.192 mmol) is added to a solution of C6-deacylated analog of di-t-butyl ester IIA (100 mg, 0.128 mmol) in pyridine (1 mL) or toluene (1 mL) containing triethylamine (90 μL) and the mixture is heated at 90° C. for 2 h. The solution is cooled and more isocyanate (0.192 mmol) is added and heating is continued for another 1 h. If the reaction is not complete as shown by TLC, more isocyanate (0.192 mmol) is added. The reaction mixture is cooled and the solid is filtered off and washed with dichloromethane. The combined flitrates are evaporated to a residue, which is purified by preparative TLC (hexanes-ethyl acetate; 4:1, v/v).

Method B

A solution of C6 deacylated analog of IIA di-t-butyl ester IIAE100 mg, 0.128 mmol) and 1,1'-carbonyldiimidazole (42 mg, 0.256 mmol) in dry toluene (0.5 mL) is stirred at room temperature for 5 h. The appropriate amine (1.28 mmol) is added and the mixture is stirred at room temperature for 3 h. The reaction mixture is diluted with hexanes, filtered, and the filtrate is evaporated to dryness. The residue is purified by preparative TLC (hexanes-ethyl acetate; 4:1 or 3:1, v/v).

General Procedure for Deprotection of Carbamates

A solution of a protected IIA-di-t-butyl ester-C6 carbamate (100 mg) in dry dichloromethane (3 mL) is treated with trifluoracetic acid (1 mL) at room temperature overnight. The solution is evaporated to a SCHEME 5
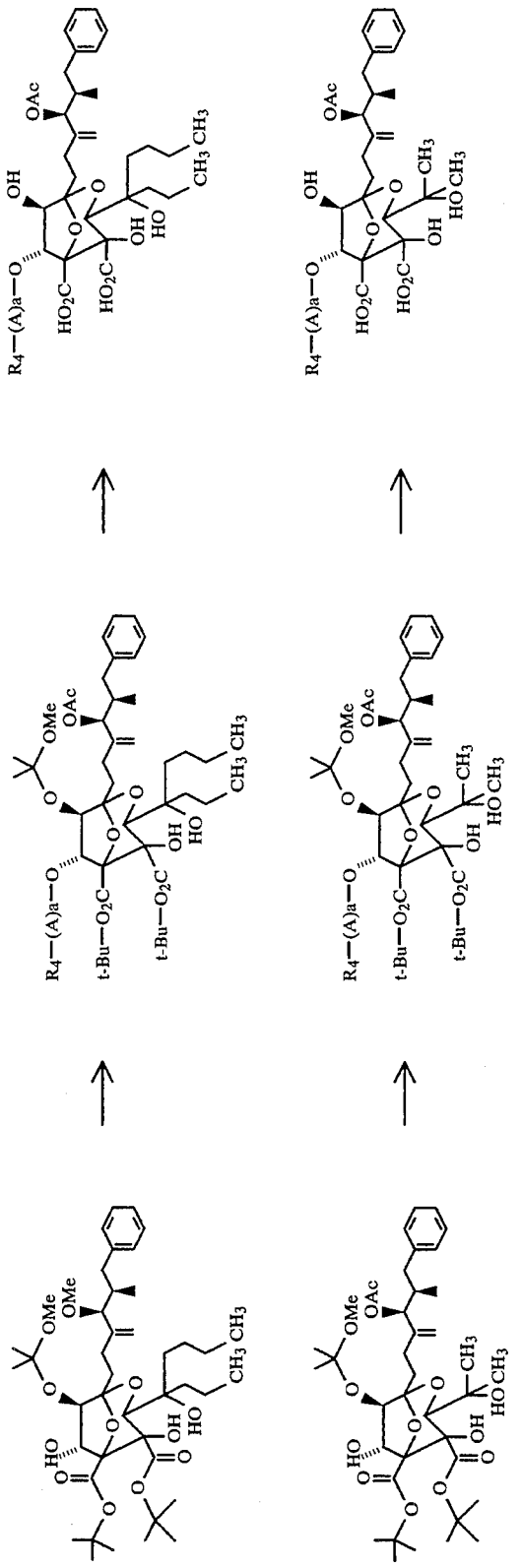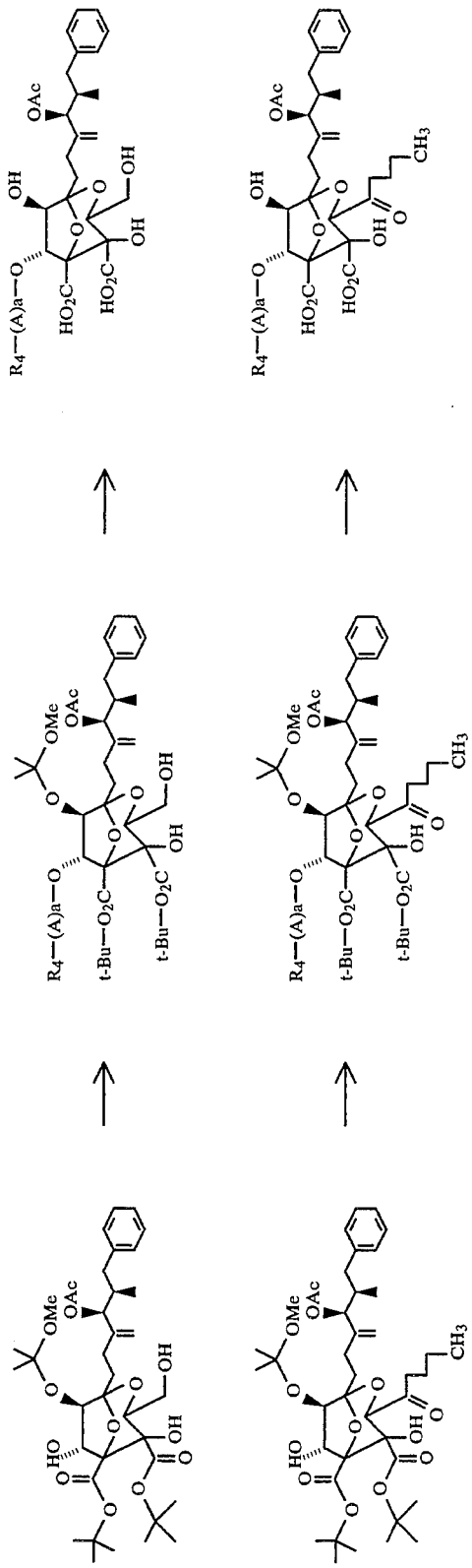

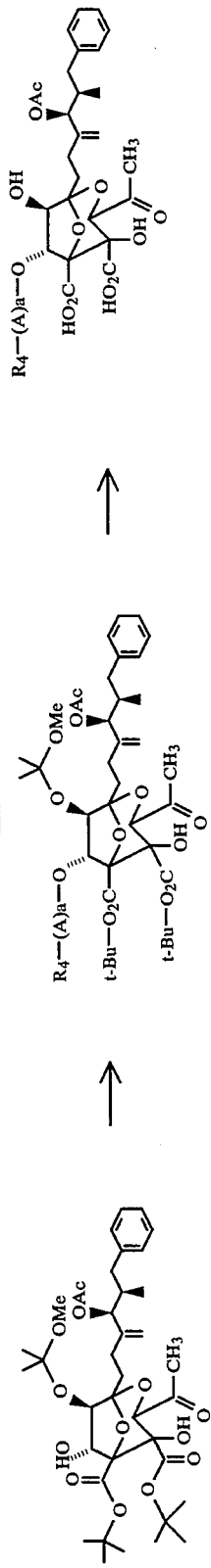

residue, which is redissolved in toluene and concentrated to dryness. This process is repeated twice, and the product is dissolved in benzene and freeze-dried to give a white solid. The purity of the products is monitored by reversed-phase HPLC.

General Procedure for Preparation of C6 Ethers

Sodium hydride (60% dispersion in mineral oil; 19.3 mg, 0.48 mmol) is added to a solution of C6-deacylated IIA-tri-t-butyl ester (300 mg, 0.384 mmol) and the appropriate organic bromide (0.48 mmol) with tetra-n-butylammonium iodide (15 mg, 0.038 mmol) in dry DMF (1.5 mL), and the reaction mixture is stirred at room temperature for 7-16 h. The mixture is partitioned between ethyl ether and water. The aqueous layer is re-extracted twice with ethyl ether, and the combined ethereal extracts are washed with brine, dried, and evaporated to dryness. Two monoalkylated products, C-6 and C-4 ethers, the C-4,6 dialkylated product and the starting material are separated by preparative TLC (hexanes/ethyl acetate, 4:1; v/v). If the appropriate organic iodide was used, tetra-n-butylammonium iodide is omitted in the above reaction.

General Procedure for Deprotection of Ethers

A solution of protected-ether prepared above (100 mg) in dry methylene chloride (3 mL) is treated with trifluoroacetic acid (1 mL) at room temperature overnight. The solution is evaporated to a residue, which is redissolved in toluene and concentrated to dryness. This process is repeated twice, and the product is dissolved in benzene and freeze-dried to give a white solid. The purity of the products is monitored by reversed-phase HPLC.

The compounds of formulae VII and VIII are prepared according to Scheme 6, the procedures in Examples 44 through 62, and the general description below:

Once the C3 position of IIA, IIB or IIC is modified as shown above, the C4 and/or C5 positions of corresponding compounds are esterified by using alkyl-O N,N'-dialkyl isourea or a base such as DBU followed by the appropriate alkyl halide.

Compounds of structural formula IX were made by catalytic reduction (Pd/C, methanol) of Compound 120 or other appropriately substituted compounds of structural formula I.

The present invention is also directed to a method of treating hypercholesterolemia which comprisies the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthetase which

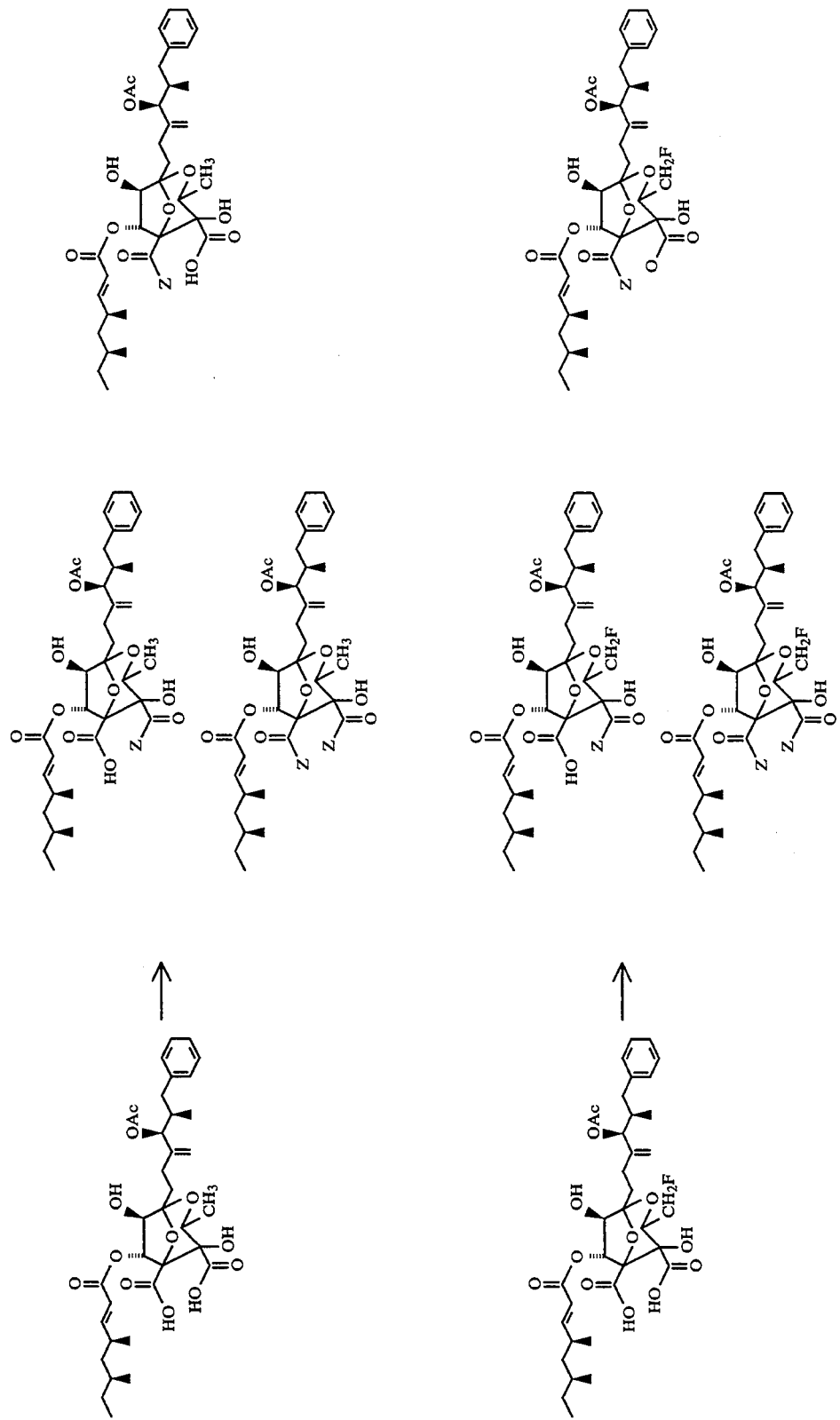

SCHEME 6 -continued
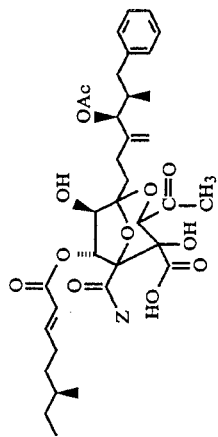
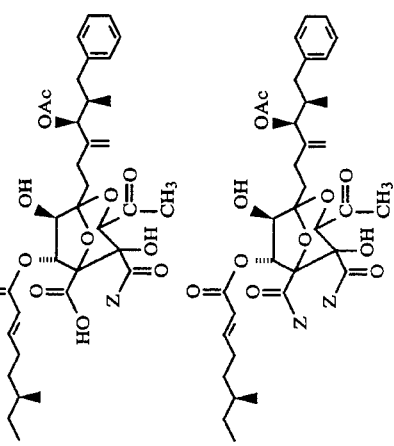
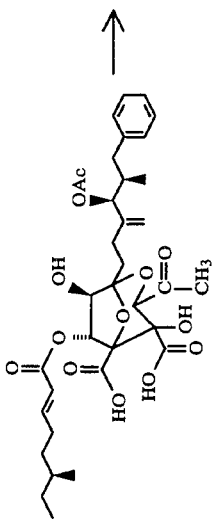

comprises the administration to a subject in need of such treatment a nontoxic therapeutically effective amount of a compound represented by structural formula (I) and pharmaceutically acceptable salts thereof. Specifically, the compounds of this invention are useful in treating disease conditions such as, but not limited to, hypercholesterolemia which result from the action of the enzyme squalene synthetase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form. These salts may be prepared by standard procedures.

The compounds of this invention may also be administered in combination with other cholesterol lowering agents such as those which inhibit an enxymatic pathway in the biosynthesis of cholesterol. Example of such agents would include but are not limited to HMG-CoA reductase inhibitors, HMG-COA synthase inhibitors, and squalene expoxidase inhibitors. Illustrative of such inhibitors are lovastatin, simvastatin, pravastatin and fluvastatin.

Examples of HMG-CoA synthase inhibitors are the beta-lactone derivatives disclosed in U.S. Pat. Nos. 4,806,564; 4,816,477; 4,847,271; and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Illustrative examples of squalene epoxidase inhibitors are disclosed in European Patent Publication EP 0 318 860 and in Japanese Patent Publication J02 169-571A. LDL-receptor gene inducer molecules are disclosed in U.S. patent application Ser. No. 07/670,640 filed Mar. 18, 1991. Other cholesterol lowering agents that may be administered include niacin, probucol, the fibric acids: clofibrate and gemfibrozil, and LDL-receptor Eene inducers. Representative of such combinations are those containing about 10–400 mg of a compound of formula (I) in combination with about 20–100 mg of an HMG-CoA reductase inhibitor, 20 to 200 mg of a HMG-CoA synthase inhibitor, or 2 to 200 mg of a squalene epoxidase inhibitor, or 250 to 1000 mg of probucol, or 600 to 1200 mg of gemfibrozil, or 1 to 2 g of clofibrate, or 3 to 6 g of niacin, or 20 to 300 mg of an LDL-receptor gene inducer.

The compounds of this invention may also be co-administered with pharmaceutically acceptable nontoxic cationic polymers capable of binding bile acids in a non-resorbable form in the gastrointestinal tract. Examples of such polymers include cholestyramine, colestipol and poly[methyl-(3-trimethyl)aminopropyl]iminotrimethylene dihalide. The relative amounts for co-administration of the compounds of this invention and these polymers is between 1:100 and 1:15,000 (w/w).

The intrinsic squalene synthase inhibitory activity of representative compounds of this invention was measured by the standard in vitro protocol described below:

Preparation of Rat Liver Microsomes

Male, CHARLES RIVER CD ® rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at $20,000 \times$ g for 15 min. at 4° C., discarding the pellet each time. The supernatant was then centrifuged at $100,000 \times$ g for 1 hr at 4° C. The resulting microsomal pellet was resuspended in a volume of the above homogenizing buffer equal to one-fifth the volume of the original homogenate. This microsomal preparation has a protein concentration of about 7 mg/mL. The microsomal suspensions were stored in aliquots at $-70°$ C. Squalene synthase activity in these aliquots is stable for a least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 $\mu$mole of farnesyl pyrophosphate per minute at 30° C. in the standard assay.

The livers of 23 forty-day old male rats that had been fed 5% cholestyramine plus 0.1% lovastatin were homogenized in a WARING blender in 1 liter of 10 mM mercaptoethanol, 2 mM EDTA, 25 mM leupeptin, 0.005% phenylmethylsulfonyl fluoride, pH 7.0 containing 0.1 trypsin inhibitor units of aprotinin/mL. The homogenate was centrifuged at $20,000 \times$ g for 20 min. The supernatant was adjusted to pH 5.5. with 6N HOAc and centrifuged at $100,000 \times$ g for 1 hour. This supernatant was adjusted to pH 7.0 with 3N KOH and a 35–60% ammonium sulfate fraction taken. The 60% pellet was redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction was applied to a $12.5 \times 5$ cm column of DEAE-sepharose 4B equilibrated with Buffer A. The column was washed with 700 mL of Buffer A and a 1 liter gradient from Buffer A to 100 mM potassium phosphate, 10 mM mercaptoethanol, 1 mM EDTA, pH 7.0. Fractions having a specific activity greater than 0.20 units/mg were combined, solid ammonium sulfate was added to bring to 60% saturation and pelleted. The pellet was dissolved in 8 mL 10 mM Tris, 10 mM $\beta$-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/mL with specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for a least 6 months.

Enzymatic Synthesis of [4-$^{14}$C]farnesyl-pyrophosphate

The solvent (ethanol: 0.15N NH$_4$OH, 1:1) was removed from 55 mCi of [4-$^{14}$C]isopentenyl pyrophosphate (47.9 mCi/mmole) by rotary evaporation. Six hundred microliters of 100 mM Tris, 10 mM MgCl$_2$, 4 mM dithiothreitol pH 7.5 was added and the solution was transferred to a 1.5 mL Eppendorf centrifuge tube. Geranyl-pyrophosphate, 250 mL of a 20 mM solution, and 50 mL of the ammonium sulfate suspension of prenyl transferase were added to initiate the reaction. This incubation contained 5 mmoles of geranyl pyrophosphate, 1.15 mmoles of isopentenyl pyrophosphate, 6 mmoles of MgCl$_2$ of 0.18 units of prenyl transferase in a volume of 900 mL. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 mL of 50 mM HEPES, 5 mM EDTA, pH 7.5. The yield was 50.7 mCi (92%) of [4-$^{14}$C]farnesyl pyrophosphate. The [4-$^{14}$C]farnesyl pyrophosphate was stored in aliquots at −70° C.

Squalene Synthase Assay

Reactions were performed in 16×125 mm screw cap test tubes. A batch assay mix was prepared from the following solution:

|   |   | mL per assay | volume for 50 assays |
|---|---|---|---|
| 1. | 250 mM HEPES pH 7.5 | 20 | 1000 |
| 2. | NaF 110 mM | 10 | 500 |
| 3. | MgCl$_2$ 55 mM | 10 | 500 |
| 4. | Dithiothreitol 30 mM | 10 | 500 |
| 5. | NADPH 10 mM (made fresh) | 10 | 500 |
| 6. | [4-$^{14}$C]farnesyl-pyrophosphate 47.9 mCi/mmole, and 0.025 mCi/3.0 mL | 3.0 | 150 |
| 7. | H$_2$O | 24 | 1200 |

This assay mix was degassed under vacuum and flushed with N$_2$. Solutions of the squalene synthase inhibitors were prepared either in DMSO or MeOH and a 1:120 dilution of the microsomal protein was made with the original homogenizing buffer. For each reaction, 87 mL of the assay mix was taken with 3 mL of an inhibitor solution (DMSO or MeOH in the controls), warmed to 30° C. in a water bath and then the reaction was initiated by the addition of 10 mL of the 1:120 dilution of microsomal protein (0.6 µg protein total in the assay). The reactions were stopped after 20 minutes by the addition of 100 mL of a 1:1 mix of 40% KOH with 95% EtOH. The stopped mix was heated at 65° C. for 30 min., and cooled. Ten mL of heptane was added and the mix was vortexed. Two g of activated alumina was then added, the mix vortexed again, the alumina allowed to settle and 5 mL of the heptane layer was removed. Ten mL of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

Representative of the squalene synthase inhibitory character of the compounds of this invention are IC$_{50}$ the data below.

| Compound | Squalene Synthase IC$_{50}$ |
|---|---|
| 128 | 3.5 nM |

The present compounds also demonstrate broad spectrum antifungal activity as determined by broth dilution methods. The compounds are particularly active towards filamentous fungi and yeasts including *Candida albicans* and *Cryptococcus neoformans*. The sensitivity of filamentous fungi and yeast was determined using inhibitor dilution assays in microtiter format. The compounds were dissolved in 10% DMSO at 256 µg/mL and serially diluted in (DIFCO) Yeast Nitrogen Base supplemented with 1% glucose (YNBD) by two-fold dilutions yielding final drug concentrations ranging from 128–0.06 µg/mL. The wells were filled with 150 µL of inoculated media. Exponential phase Candida and Cryptococcus cells were diluted in YNBD such that the inoculum was 1.5–7.5×10$^3$ cells/mL. Aspergillus spores were harvested from a well-sporulated Sabouraud Dextrose Agar (SDA) slant in 0.01% Tween 80 and diluted into media to give an inoculum of 1×10$^3$ spores/mL. The microtiter dishes were incubated at 35° C. for 24 to 48 hours. The minimum inhibitory concentration (MIC) is defined as the lowest concentration to prevent visible growth after incubation for 24 to 48 hours at 35° C. for the yeasts and at 29° C. for the filamentous fungi. After recording the MIC of yeasts, plates were shaken on a (SARSTEDT) TPM2 shaker to resuspend the cells and a MIC-2000 inoculator (DYNATECH) was used to transfer a 1.5 µL sample from each well in the microplate to a spot in a single-well tray containing SDA. Inoculated trays were incubated at 35° C. and results were recorded at 24 h or 48 h (for Cryptococcus). The minimum fungicidal concentration (MFC) was defined as the lowest concentration of drug showing no growth or less than 4 colonies per spot. Representative of the antifungal activity are the concentration data shown below.

| Organism | Compound | |
|---|---|---|
| Minimum Inhibitory Concentration (µg/mL) | | |
| | | MIC µg/mL |
| *Aspergillus fumigatus* MF4839 | 128 | 16 |
| Minimum Fungicidal Concentration (µg/mL) | | |
| | | MFC µg/mL |
| *Candida albicans* MY1055 | 128 | 128 |
| *Cryptococcus neoformans* MY1051 | 128 | 0.5 |

Thus the present invention is also directed to a method of inhibiting fungal growth which comprises the application to the area in which growth is to be controlled an antifungally effective amount of a compound of Formula (I). Additionally, the present invention is directed to a method of treating fungal infections which comprises the administration to an organism in need of such treatment a nontoxic therapeutically effective amount of a compound represented by the structural formula (I) and pharmaceutically acceptable salts thereof. Based on the above MIC data it is determined that generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, o may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The present invention is also directed to compounds of structural formula (I) which are inhibitors of farnesyl-protein transferase for inhibition of farnesylation of the oncogene protein Ras and the treatment of cancer.

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci. USA*, 87:7541–7545 (1990)).

Inhibition of farnesyl-protein transferase and, thereby, of farnesylation of the Ras protein, blocks the ability of Ras to transform normal cells to cancer cells. Surprisingly, the compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634 (1989)). Cytosol-localized forms of Ras with normal GTPase activity do not act as inhibitors. Gibbs et al., ibid, showed this effect in Xenopus octyes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

FARNESYL-TRANSFERASE ASSAY

Farnesyl-protein transferase (Ftase) from bovine brain was chromatographed on DEAE—Sephacel (Pharmacia, 0–0.8M NaCl gradient elution), N-octyl agarose (Sigma, 0–0.6M NaCl gradient elution), and a MONO Q HPLC column (Pharmacia, 0–0.3M NaCl gradient). Ras-CVLS at 3.5 μM, 0.25 μM [$^3$H]FPP, and the indicated compounds were incubated with this partially purified enzyme preparation. The Ftase data is a measurement of the ability of the test compound to inhibit Ras farnesylation in vitro.

| Compound | IC$_{50}$ |
|---|---|
| 128 | 3.3 μM |

The pharmaceutical compositions containing the compounds of structural formula (I) inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone, or preferably, in combination with pharmaceutically-acceptable carriers or diluents, optionally with known-adjuvants, such as alum, in a pharmaceutical composition, according to standard pharmaceutical practice. The compounds can be administered orally or parenterally, including intravenous, intramuscular, intraperitioneal, subsutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in a amount between about 0.1 mg/kg of body weight of about 20 mg/kg of body weight of a mammal per day, preferably of between 0.5 mg/kg of body weight to about 10 mg/kg of body weight of a mammal per day.

The following examples illustrate the preparation of the compounds of formula (I) and their incorporation into pharmaceutical compositions and, as such, are not to be considered as limiting the invention set forth in the claims appended hereto.

EXAMPLE 1

IIA-3-hydroxymethyl (100) (Method 1)

Step A: IIA-3-Benzyl ester

Acetyl chloride (0.4 mL) was added to benzyl alcohol (10 mL) and the reaction mixture stirred at room temperature for 30 min. Solid IIA (1 g) was added and the reaction mixture stirred for additional six hours. The mixture was degassed, poured into acetonitrile-water mixture (200 mL, 38%), filtered through a bed of C-8 reverse phase column (30 g. BAKER) to remove unreacted benzyl alcohol, washed several times with acetonitrile (400 mL). Evaporation under vacuum gave IIA-3-benzyl ester (86% pure by HPLC). Further purification was carried out by reverse phase (RP) chromatography (C-8 Baker, 58% acetonitrile in water).

$^1$NMR (300 MHz, CD$_3$OD) δ 7.46–7.12 (m, 10H), 6.88 (dd, J=8.9, 18 Hz, 1H), 6.38 (brs, 1H), 5.48 (d, J=15 Hz, 1H), 5.42 (s, 1H), 5.23 (dd, J=14, 5.1 Hz, 2H), 5.14 (s, 1H), 5.04 & 5.00 (2s, 2H), 4.06 (brs, 1H), 2.71 (m, 1H), 2.54–2.00 (m, 7H), 2.12 (s, 3H), 1.50–1.1 (m, 6H), 1.07 (d, J=6 Hz, 3H), 0.90 (m, 9H); FAB m/e 793 (M+2Li), 799 (M+3Li).

Step B: IIA-3-Benzyl-4,5-di-t-butyl ester

A solution of IIA-3-benzyl ester (100 mg) dissolved in methylene chloride (2 mL) was treated with O-t-butyl- N,N'-diisopropylisourea (300 mg) and heated at 40° C. for 2 days. The reaction mixture was cooled to room temperature, concentrated and filtered through a bed of silica (25% ethyl acetate in hexane) to yield pure IIA-3-benzyl-4,5-di-t-butyl-ester.

$^1$NMR (400 MHz, CDCl$_3$) δ 7.35–7.08 (m, 10H), 6.88 (dd, J=8.4,16 Hz, 1H), 5.97 (d, J=1 Hz, 1H), 5.75 (d, J=16 Hz, 1H), 5.42 (s, 1H) 5.16 (dd, J=12, 6.4 Hz, 2H), 5.06 (br s,1H), 4.94 (br s, 2H), 4.00 (br s, 1H), 2.96 (d, J=2 Hz, 1H), 2.66 (m, 1H), 2.5–2.2 (m, 5H).

Step C: IIA-7-(1-Methyl-1-methoxyethyl ether)-3-benzyl-4,5-di-t-butyl ester

A solution of the diol (3.0 g) and 2-methoxypropene (4.1 mL) in methylene chloride (43 mL) was cooled to 0° C. and pyridinium p-toluenesulfonate (58.5 mg) was added. After stirring for 2 h the solution was neutralized with satd. sodium bicarbonate and extracted with diethyl ether. The organic layer was separated and washed with brine, dried over magnesium sulfate and filtered. The filtrate evaporated in vacuo. Purification of the residue by flash column (silica gel, ethyl acetate/hexane 1:4) gave the ketal.

$^1$NMR (400 MHz, CD$_3$OD) δ 7.4–7.12 (m, 10H), 6.88 (dd, J=8.5,15.6 Hz, 1H), 6.48 (d, J=1.85 Hz, 1H), 5.84 (d, J=15.6 Hz, 1H), 5.29 (s, 1H), 5.23 and 5.10 (ea d, J=12 Hz, ea 1H), 5.07 (d, J=4.8 Hz, 1H), 4.99 and 4.99 (ea s, ea 1H), 4.23 (d, J=1.85 Hz, 1H), 3.18 (s, 3H), 2.09 (s, 3H), 1.52 and 1.39 (ea s, ea 9H), 1.34 (s), 1.26 (s), 1.02 (d, J=6.7 Hz, 3H), 0.9–0.8 (m, 9H).

Step D: IIA-7-(1-methyl-1-methoxyethyl ether)-4,5-di-t-butyl ester

To a solution of IIA-7-(1-methyl-1-methoxyethyl ether)-3-benzyl-4,5-di-butyl ester (100 mg) in methanol (4 mL) was added methyl cyclohexadiene (200 μL) and Pd/C (50 mg). The reaction mixture was stirred at 30°–35° C. for 1.5 hr and filtered over CELITE. The filtrate was evaporated under vacuum to give IIA-(1-methyl-1-methoxyethyl ether)4,5-di-t-butyl ester.

$^1$NMR (200 MHz, CD$_3$OD) δ 7.30–7.15 (m, 5H), 692 (dd, J=8.4, 15.6 Hz, 1H), 6.50 (d, J=1.7 Hz, 1H), 5.85 (d, J=15.6 Hz, 1H), 5.19 (s, J=5, 1H) 5.08 (d, J=4.78 Hz, 1H), 5.02 and 4.97 (each s, each 1H), 4.25 (d, J=1.7 Hz, 1H), 3.19 (s, 3H), 2.10 (s, 3H), 1.63 and 1.50 (ea s, 9H), 1.35 (s), 1.26 (d, J=5.8 Hz, 3H), 1.02 (d, J=6.73 hz, 3H), 0.88–0.82 (m, 9H)

Step E: IIA-7-(1-methoxy-1-methylethyl ether)-3-hydroxymethyl-4,5di-t-butyl ester To a solution of IIA-7-(1-methoxy-1-methylethyl ether)-4,5-di-t-butyl ester (50 mg) in methylene chloride (1.0 mL) under nitrogen atmosphere at room temperature was added N-methylmorpholine (6.93 μL) and stirred for 20 min then cooled to −20°. At −20° isobutyl chloroformate (8.17 μL) was then added dropwise and stirring continued for additional hour at the same temperature. THF (1.3 mL) was then added and reaction mixture allowed to warm up to 0°. After 10 min precipitate was filtered off under N$_2$ and sodium borohydride (6.51 mg) was added in one portion; methanol (0.57 mL) was then added dropwise at 0°. After stirring at 0° for 20 min, the reaction mixture was quenched with saturated aq. ammonium chloride, concentrated, and extracted with ethyl acetate to yield the crude product which was purified by prep TLC preparative thin layer chromatography (ethyl acetate/hexane 1/1) to yield IIA-(1-methoxy-1-methyl- ethyl ether)-3-hydroxymethylene-4,5-di-t-butyl ester.

$^1$HNMR (400 MHz, CD$_3$OD) δ 7.29–7.16 (m, 5H), 6.89 (dd, J=8.53, 15.6 Hz), 6.49 (d, J=1.99 Hz, 1H), 5.85 (d, J=15.6 Hz, 1H), 5.06 (d, J=4.57 Hz, 1H), 4.95 and 4.97 (ea br s, ea 1H), 4.63 (t, J=5.75, 1H), 4.20 (d, J=1.99 Hz, 1H), 3.57 (m, 2H), 3.19 (s, 3H), 2.10 (s, 3H), 1.62 (s, 9H), 1.40 (s, 9H), 1.34 (s), 1.27 (s), 1.03 (d, J=6.64, 3H), 0.88–0.84 (m, 9H).

Step F: IIA-3-hydroxymethyl

Deprotection of 300 mg IIA-3-hydroxymethyl-4,5-di-5-butyl-ester in 6.5 mL methylene chloride with 1.2 mL trifluoroacetic acid gave a 2:1 mixture of the alcohol and the corresponding C3-C4 lactone (HPLC Rt 10.4, 19.8 min). They were separated by MPLC on a RP C-8 column to yield the IIA-3-hydroxymethyl.

$^1$HNMR (400 MHz, CD$_3$OD) δ 7.27–7.14 (m, 5H), 6.84 (dd, J=8.5, 15.63 Hz, 1H), 6.29 (d, J=1.98 Hz, 1H), 5.75 (d, J=15.63 Hz, 1H), 5.05 (d, J=4.65 Hz, 1H), 4.98 and 4.94 (ea s, ea 1H), 4.65 (t, 1H), 4.00 (d, J=1.98, 1H), 3.63 (m, 2H), 2.66 (dd, J=6.3 Hz, 13.5 Hz, 1H), 2.5–2.14 (m), 2.09 (s, 3H), 2.0–1.9 (m), 1.43–1.24 (m), 1.16–1.11 (m), 1.03 (d, J=6.64 Hz, 3H), 0.88–0.84 (m, H); MS(FAB) m/e 695 [M+3Li]

EXAMPLE 2

IIA-3-hydroxymethyl (100) Method 2

Step A: IIA-4,5-di-t-butyl ester

To a solution of IIA-3-benzyl-4,5-di-t-butyl ester prepared according to Example 1, Step B (100 mg) in methanol (4 mL) was added methyl cyclohexadiene (200 μL) and Pd/C (50 mg). The reaction mixture was stirred at 30°–35° C. for 1.5 hr and filtered over CELITE. The filtrate was evaporated under vacuum to give IIA-4,5-di-t-butyl ester. 1NMR (400 MHz, CD$_3$OD) δ 7.30–7.10 (m, 5H), 6.89 (dd, J=8,16 Hz, 1H), 6.43 (d, J=1 Hz, 1H), 5.82 (d, J=16 Hz, 1H), 5.06 (d, J=5 Hz, 1H) 5.04 (s,1H), 5.01 (each s, each 1H), 4.07 (s, 1H), 2.69 (m, 1H), 2.5–2.22 (m, 6H), 2.10 (s, 3H), 1.60 (s, 9H), 1.42 (s, 9H), 1.65–1.05 (m, 6H), 1.03 (d, J=8.1 Hz, 3H), 0.88 (m, 10H)

Step B: IIA-3-hydroxymethyl-4,5-di-butyl ester

To a solution of IIA-4,5-di-t-butyl ester (46 mg) in methylene chloride (1.02 mL) under nitrogen atmosphere, was added at room temperature N-methylmorpholine (6.93 μL) and stirred for 20 min then cooled to −20° C. At −20° C. isobutyl chloroformate (8.17 μL) was then added dropwise and stirring continued for additional hour at the same temperature. THF (1.3 mL) was then added and reaction mixture allowed to warm up to 0° C. After 10 min, precipitate was filtered off under N$_2$ and sodium borohydride (6.51 mg) was added in one portion; methanol (0.57 mL) was then added dropwise at 0° C. After stirring at 0° C. for 20 min, the reaction mixture was quenched with sat'd aq. ammonium chloride, concentrated, and extracted with ethyl acetate to yield the crude product which was purified by prep TLC (ethyl acetate/hexane 1/1) to yield the IIA-3-hydroxymethylene-4,5-di-t-butyl ester.

EXAMPLE 3

IIA-3-Hydroxymethyl

The above product from Example 2 was deprotected according to the procedure of Example 1, Step F, to yield IIA-3-hydroxymethyl.

$^1$HNMR (400 MHz, CD$_3$OD) δ 7.31–7.11 (m, 5H), 6.88 (dd, J=8.5, 15.6 Hz), 6.39 (d, J=1.8 Hz, 1H), 5.81 (d, J=15.6 Hz, 1H), 5.05 (d, J=4.6 Hz, 1H), 4.99 and 4.95 (ea br s, ea 1H), 4.65 (t, 1H), 4.05 (d, J=1.8 Hz, 1H), 3.58 (m, 2H), 2.10 (s, 3H), 1.64 (s, 9H), 1.42 (s, 9H).

EXAMPLE 4

IIA-3-hydroxyymethyl-4-methyl ether (105)

Step A: IIA-3-Hydroxymethyl-4-methyl ether 4,5-di-t-butyl ester

Methyl iodide (11.89 μL) was added to a stirred solution of IIA-3-hydroxymethyl-4,5-di-t-butyl ester (100.5 mg)(prepared in Example 2 Step B) in DMF (0.82 mL) containing tetrabutyl ammonium iodide (4.78 mg). After 10 min the mixture was cooled to 0° C. and 50% NaH (7.35 mg) was added. The mixture was allowed to slowly warm up to room temperature and was held at 25° for 1 hour. After evaporation and preparative TLC purification. IIA-3-hydroxymethyl-4-methyl ether-4,5-di-t-butyl ester was isolated.

$^1$HNMR (400 MMz, CD$_3$OD) δ 7.3–7.12 (m, 5H), 6.90 (dd, J=8.5, 15.68, 1H), 6.46 (d, J=2.17 Hz, 1H), 5.84 (d, J=15.68, 1H), 5.04 (d, J=4.56 Hz, 1H), 4.98 (s, 1H), 4.94 (s, 1H), 4.67 (t, 1H), 3.99 (d, J=2.17, 1H), 3.72–3.64 (m, 1H), 3.61 (s, 3H), 3.59–3.51 (m, 1H), 2.68–2.61 (m), 2.52–2.41 (m, 2H), 2.10 (s, 1H), 2.02–1.80 (m), 1.57 (s, 9H), 1.44–1.25 (m), 1.2–1.08 (m), 1.03 (d, J=6.65 Hz, 3H), 0.92–0.81 (m, 9H).

Step B: IIA-3-Hydroxymethyl-4-methyl ether and its 3,4-lactone

IIA-3-hydroxymethyl-4-methyl ether-4,5-di-t-butyl ester (23 mg) was hydrolyzed in methylene chloride (1.5 mL) and trifluoroacetic acid (0.3 mL) at r.t. for 16 h to give after evaporation IIA-hydroxymethyl-4-methyl ether and its 3,4-lactone (1:1 mixture).

$^1$HNMR (400 MHz, CD$_3$OD) δ 7.3–7.1 (m, 5H), 6.85 (dd, J=7.88, 15.44, 1H), 6.40 (br s, 1H), 5.79 (d, J=15.44, 1H), 5.03 (br s, 1H), 4.98 (s, 1H), 4.94 (s, 1H), 4.69, 4.52, 4.40 (ea m, total 2H), 3.97 (d, J=1.9 Hz, 1H), 3.65 (br s, 4H), 2.64 (dd, J=6.3, 13.5 Hz, 1H), 2.68–2.61 (m), 2.5–2.4 (m, 2H), 2.4–2.1 (m), 2.10 (s, 3H), 2.05–1.82 (m), 1.46–1.23 (m), 1.23–1.06 (m), 1.03 (d, J=6.7 Hz, 3H), 0.91–0.78 (m, 9H); MS(FAB with Li) m/e 703 [M+2Li], 709[M+3Li]

EXAMPLE 5

IIA-3-methoxymethyl-4-methyl ether (109)

Step A: IIA-3-methoxymethyl-4-methyl ether-7-(1-methoxy-1-methyl ethyl ether)-4,5-di-t-butyl ester By applying the procedure of Example 4 Step A and starting with IIA-3-hydroxymethyl-7-(1-methoxy-1-methylethyl ether)-4,5-di-t-butyl ester (80.2 mg, Example 1, Step E), DMF (0.61 mL), methyl iodide (8.83 μL), tetrabutyl-ammonium iodide (3.55 mg), 50% NaH oil dispersion (5.46 mg), the title compound was produced in addition to IIA-3-hydroxymethyl-7-(1-methoxy-1-methylethyl ether)4-methylether-4,5-di-t-butyl ester.

$^1$HNMR (200 MHz, CD$_3$CN) δ 7.47–7.31 (m, 5H), 6.99 (dd, J=8.47, 15.72, 1H), 6.60 (d, J=2.17 Hz, 1H), 5.97 (d, J=15.72, 1H), 5.10 (m, 1H), 4.84 (dd, J=3.42, 6.56 Hz, 1H), 4.25 (d, J=2.17 Hz, 1H), 3.68 (s, 3H), 3.67–3.43 (m, 2H), 3.41 (s, 3H), 3.27 (s, 3H), 2.85–2.50 (m, 3H), 2.5–2.2 (m), 2.20 (s, 3H),2.05–1.8 (m), 1.68 (s, 9H), 1.51 (S, 9H), 1.43 (s, 3H), 1.37 (s, 3H), 1.35–1.16 (m), 1.14 (d, J=6.73 Hz, 3H).

Step B: IIA-3-Methoxmethyl-4-methyl ether

IIA-3-methoxymethyl-4-methyl ether-7-(1-methoxy-1-methylethyl ether)-4,5-di-t-butyl ester (35.7 mg) was hydrolyzed with trifluoracetic acid (300 μL) in methylene chloride (2 mL) to afford IIA-3-Methoxymethyl-4-methyl ether.

$^1$HNMR (400 MHz, CD$_3$OD) δ 7.27–7.1 (m, 5H), 6.85 (dd, J=8.48, 15.68, 1H), 6.40(d, J=1.93 Hz, 1H), 5.78 (d, J=15.68, 1H), 5.04 (d, J=4.66, 1H), 4.95 and 4.98 (ea s, ea 1H), 4.79 (t, J=5.34 Hz, 1H), 3.97 (d, J=1.93 Hz, 3H), 3.67 (s, 3H), 3.54 (d, J=5.62 Hz, 2H), 3.31 (s, 3H), 2.64 (dd, J=6.70, 13.55 Hz, 1H), 2.48–2.4 (m, 2H), 2.38–2.11 (m) 2.09 (s, 3H), 2.05–1.81 (m), 1.43–1.21 (m), 1.21–1.07 (m, 2H), 1.02 (d, J=6.69 Hz, 3H), 0.9–0.79 (m, 9H); MS(fab) m/e 723[m+3Li].

EXAMPLE 6

IIA-3-hydroxymethyl-7-benzyl ether (101) and IIA-3-hydroxymethyl-4,7-dibenzyl ether (102)

Step A: IIA-3-Hydroxymethyl-7-benzyl ether-4,5-di-t-butyl ester and IIA-3-hydroxymethyl-4,7-dibenzyl ether-4,5-di-t-butyl ester To a stirred solution of IIA-3-hydroxymethyl-4,5-di-t-butyl ester (85.5 mg, 0.108 mmol) in 0.7 mL DMF containing tetrabutylammonium iodide (4.07 mg, 0.011 mmol) at ambient temperature under N$_2$ was added benzyl bromide (19.41 mL, 0.163 mmol). After 10 min the mixture was cooled to 0° C., NaH (50% oil dispersion, 6.3 mg, 0.13 mmol) was added. Stirring continued at 0° for 1 h before warming up to room temperature and was stirred at 25° for 2 h more. The mixture was quenched with aq. NaH$_2$PO$_4$ and extracted with EtOAc. Preparative TLC produced IIA-3-hydroxymethyl-7-benzyl ether-4,5-di-t-butyl ester:

$^1$HNM-R (400 MHz, CD$_3$OD) δ 7.32–7.07 (m, 10H), 6.92 (dd, J=8.4, 15.72 Hz, 1H), 6.64 (d, J=1.9 Hz, 1H), 5.82 (d, J=15.72 Hz, 1H), 5.01 (d, J=4.54 Hz, 1H), 4.93 (br s, 2H), 4.76 & 4.50 (ea d, ea J=12 Hz, ea 1H), 4.69 (t, 1H), 3.88 (d, J=1.9 Hz, 1H), 3.57 (m, 2H), 2.63 (m, 2H), 2.09 (s, 3H), 1.60 & 1.41 (ea s, ea 9H), 1.03 (d, J=6.64 Hz, 3H), 0.93–0.8 (m, 9H) and IIA-3-hydroxymethyl-4,7-dibenzyl ether-4,5-di-t-butyl ester $^1$HNMR (400 MHz, CD$_3$OD) δ 7.4–7.02 (m, 15H), 6.92 (dd, J=8.47, 15.72 Hz, 1H), 6.64 (d, J=17 Hz, 1H), 5.82 (d, J=15.72 Hz, 1H), 5.01 (d, J=4.89 Hz, 1H), 4.93(s), 4.92–4.82(m), 4.77 & 4.52 (ea d, ea J=12 Hz, ea 1H), 4.47 and 4.42 (ea d, ea J=12 Hz, ea 1H), 3.93 (d, J=1.7 Hz, 1H), 3.56–3.40 (m, 2H), 2.65–2.1(m), 2.09 (s, 3H), 1.98–1.83(m), 1.51 and 1.41 (ea s, ea 9H), 1.22–1.08 (m), 1.03 (d, J=6.7 Hz, 3H), 0.92–0.78 (m, 9H).

Step B: IIA-3-hydromethyl-7-benzyl ether and the corresponding 3,4-lactone

The hydrolysis of the di-t-butyl ester groups of IIA-3-hydroxylmethyl-7-benzyl ether-4,5-di-t-butyl ester in CH₂Cl₂ with TFA was done under previously described condition gave IIA-3-hydroxymethyl-7-benzyl ether and the corresponding 3,4-gamma-lactone.

¹HNMR (400 MHz, CD₃OD) δ 7.38–7.03 (m, 10H); 6.89 (dd, J=8.57, 15.70 Hz, 1H), 6.61 (d, J=1.75 1Hz, 1H), 5.81 (d, J=15. 70 Hz, 1H), 5.01 (m), 4.7 and 4.32 (2m, total 1H), 5.5 7–4.48(m, 2H), 3.88 and 3.83 (ea m), 3.62 (m, 1H), 2.89–2.76(m), 2.68–2.53 (m), 2.52–2.13(m), 2.09 and 2.04 (2s, total 3H), 2.97–2.80 (m), 1.47–1.08(m), 1.03 (d, J=6.68 Hz, 3H), 0.92–0.8 (m, 9H), MS, FAB m/z=811 (M+ +2Na).

Step C: IIA-3-hydroxymethyl-4,7-dibenzyl ether and the corresponding 3,4-gamma-lactone This product was obtained from IIA-3-hydroxy methyl-4,7-dibenzyl ether-4,5-di-t-butyl ester as shown in Example 6 Step B.

¹HNMR (400 MHz, CD₃OD) δ 7.39–7.01 (m, 15H), 6.89 (dd, J=8.5, 15.77 Hz, 1H), 6.63 (br s, 1H), 5.81 (d, J=15.77 Hz, 1H), 4.99 (d, J=4.56 Hz, 1H), 4.92 (br s), 4.55 (d, J=12 Hz, 1H), 4.46 (s, 2H), 3.89 (br s, 1H), 3.56 (br s, 2H), 2.60 (dd, J=6.70, 13.55 Hz, 1H), 2.52–2.08 (m), 2.09 (s, 3H), 2.0–1.82 (m), 1.5–1.08(m), 1.03 (d, J=6.69 Hz, 3H), 0.92–0.75 (m, 9H). MS FAB m/z=879 (m+Na); 901(m+2Na).

EXAMPLE 7

IIA-3-hydroxymethyl-7-methyl ether (105), IIA-3-hydroxymethyl-4,7-dimethyl ether (104) and IIA-3-methyoxymethyl-4,7-dimethyl ether (106)

Step A: IIA-3-hydroxymethyl-7-methyl ether-4,5-di-t-butyl ester

Utilizing the same procedure and reaction conditions as the preparation of benzyl-ethers (Example 6) 0.82 mg of IIA-3-hydroxymethyl-4,5-di-t-butyl ester gave a mixture of the C7-methyl ether, the 4,7-dimethyl ether and the 3-methoxymethyl-4,7-dimethyl ether with their corresponding NMR data listed below.

IIA-3-hydroxymethyl-7-methyl ether-4,5-di-t-butyl ester

¹HNMR (400 MHz, CD₃OD) δ 7.31–7.12 (m, 5H), 6.92 (dd, J=8.53, 15.68 Hz, 1H), 6.56 (d, J=1.69 Hz, 1H), 5.82 (d, J=15.68 Hz, 1H), 5.03 (d, J=4.56 Hz, 1H), 4.99 and 4.95 (ea s, ea 1H), 4.58 (t, J=5.71 Hz, 1H), 3.74 (d, J=1.69 Hz, 1H), 3.55 (m, 2H), 3.42 (s, 3H), 2.65 (dd, J=6.4, 13.27 Hz, 1H), 2.51–2.39 (m), 2.38–2.13(m), 2.09 (s, 3H), 2.0–1.9(m), 1.59 and 1.41 (ea s, ea 9H), 1.4–1.08 (m), 103 (d, J=6.67 Hz, 3H), 0.92–0.8 (m, 9H).

IIA-3-hydroxymethyl-4,7-dimethyl ether-4,5-di-t-butyl ester

¹NHMR (400 MHz, CD₃OD) δ 7.30–7.12 (m, 5H), 6.93 (dd, J=8.39, 15.71 Hz, 1H), 6.62 (d, J=1.75 Hz, 1H), 5.83 (d, J=15.71Hz, 1H), 5.03 (d, J=4.47 Hz, 1H), 5.99 and 5.96 (ea s, ea 1H), 4.65 (br s, 1H), 3.70 (d, J=1.75 Hz, 1H), 3.64 and 3.4 (ea s, ea 3H), 3.7–3.5 (m), 2.64 (dd, J=6.4, 13.26 Hz, 1H), 2.53–2.4 (m), 2.4–2.14(m), 2.10 (s, 3H), 2.0–1.89 (m, 2H), 1.59 and 1.44 (ea s, ea 9H), 1.44–1.08 (m), 1.03 (d, J=6.68 Hz, 3H), 0.92–0.82 (m, 9H).

IIA-3-methyoxymethyl-4,7-dimethyl ether-4,5-di-t-butyl ester

¹HNMR (400 MHz, CD₃OD) spect. similar to the foregoing compound with characteristic resonances at δ 3.65, 3.45 and 3.33 according to three methoxy groupings.

Step C

The hydrolysis of the di-t-butyl ester groups were carried out as shown in Example 6 above. Their NMR data are listed below.

Compound 105 and the Corresponding 3,4-gamma-lactone

¹HNMR (400 MHz, CD₃OD) δ 7.3–7.10 (m, 5H), 6.84 (dd, J=8.4, 15.75 Hz, 1H), 6.53 (m, 1H), 5.79 (d, J=15.75 Hz, 1H), 5.03 (m, 1H), 4.98 and 4.95 (ea s, ea 1H), 4.67–4.21 (m, 1H), 3.67 (d, J=3.74 Hz), 3.69–3.47 (m), 3.48 and 3.47 (2s, 3H total), 3.31 and 3.30 (2s, 3H total), 2.66 (dd, J=6.5, 13.3 Hz, 1H), 2.52–2.38 (m, 2H), 2.37–2.17 (m), 2.09 (s, 3H), 2.04–1.90 (m), 1.44–1.21(m), 1.20–1.07(m), 1.03 (d, J=6.64 Hz, 3H), 0.93–0.77 (m, 9H).

Compound 107 and the Corresponding 3,4-gamma-lactone

¹HNHR (400 MHz, CD₃OD) δ 7.3–7.11 (m, 5H), 6.87 (dd, J=8.4, 15.74 Hz, 1H), 6.61 and 6.54 (ea br s, total 1H), 5.79 (d, J=15.74 Hz, 1H), 5.04 (d, J=4.56 Hz, 1H), 5.99 and 5.96 (ea s, ea 1H), 4.78 and 4.60 (ea b, s, total 1H), 4.54 and 4.38 (ea m, ea 1H), 3.7 and 3.65 (ea s), 3.64 (3H), 3.45 (3H), 2.63 (dd, J=6.4, 13.3 Hz, 1H), 2.51–2.37 (m, 2H), 2.36–2.18 (m), 2.10 (s, 3H), 2.03–1.89(m), 1.47–1.07 (m), 1.03 (d, J=6.65 Hz, 3H), 0.93–0.78 (m, 9H), MS FAB. m/z=727 (m+Na). 749 (m+2Na).

Compound 106

¹HNMR (200 MHz, CD₃OD) δ 7.37–7.10 (m, 5H), 6.87 (dd, J=8.4, 15.68 Hz, 1H), 6.61 (d, J=2.0 Hz, 1H), 5.78 (d, J=15.68 Hz, 1H), 5.04 (d, J=4.66 Hz, 1H), 4.99 and 4.96 (ea s, ea 1H), 4.71 (m, 1H). 3.66, 3.47 and 3.33 (ea s, ea 3H), 3.52 and 3.49 (ea s), 2.65 (dd, J=6.4, 13.27 Hz, 1H) 2.54–2.13(m), 2.10 (s, 3H), 2.05–1.9(m), 1.5–1.1(m), 1.03 (d, J=6.67 Hz, 3H), 0.93–0.72 (m, 9H). MS, FAB m/z=741 (m+Na), 763 (m+2Na).

EXAMPLE 8

IIA-3-Benzyloxymethyl (108)

Step A: IIA-3-Benzyloxymethyl-4,5-di-t-butyl ester

Benzyltrichloroacetimidate (19.83 mg, 0.078 mmol) was added to a stirred solution of IIA-3-hydroxymethyl-4,5-di-t-butyl ester (51.7 mg, 0.066 mmol) in 0.7 mL methylene chloride containing 1.5 mL cyclohexane at ambient temperature under N₂. The mixture was cooled to 0° C., trifluoromethanesulfonic acid (2.4 mL) was added, stirred at 0° C. for 1.5 h, then at room temperature for 16 h. After quenching with aq. NaHCO₃ and extracting with methylene chloride, the organic phase was washed with water and salt solution, dried over magnesium sulfate, and evaporated to give a residue that was purified by preparative TLC (EtOAc/hex 3:7 v/v) to yield the IIA-3-benzyloxy-4,5-di-t-butyl ester.

¹HNMR (CD₃OD) exhibits characteristic resonances δ 7.33–7.08 (m, 10H, aryl), 4.8 (ABq, 2H, —O—CH₂—pH), 3.49 (m, 2H, —CH₂—O—Bu) 1.50 and 1.42 (2s, ea 9H, 2-t-butyl).

Step B: IIA-3-Benzyloxymethyl

The compound obtained in Example 8 Step A was deprotected in CH₂CH₂ (1 mL) with 250 μL of TFA at room temperature for 16 h, giving IIA-3-benzyloxymethyl.

¹HNMR (400 MHz, CD₃OD) δ 7.39–7.08 (m, 10H), 6.84 (dd, J=8.40, 15.68 Hz, 1H), 6.32 (d, J=1.7 Hz, 1H), 5.80 (d, J=15.68 Hz, 1H), 5.06 (d, J=4.8 Hz, 1 h), 4.99 and 4.94 (ea s, ea 1H), 4.92–4.82(m), 4.52 (s, 2H), 3.98 (br, s, 1H), 3.58 (br, s, 2H). MS FAB-pos m/z=833.5 (M⁺+3 Na); 811.5 (M⁺+2Na).

EXAMPLE 9

IIA-3-Butyl ketone (120)

Step A: IIA-3-butyl ketone-7-(1-methyl-1-methoxyethyl ether)-4'-hydroxy-4,5-di-t-butylester Cerium (III) chloride (1.6 g) was heated to 150° C. under vacuum (0.1 mm) for 1.5 h. After cooling to room temperature, the flask was purged with nitrogen and tetrahydzofuran (13.2 mL) was added. The mixture was stirred at room temperature for 2 h, cooled to −70°, and n-butyllithium (1.54 mL of 2.5M solution in hexane) was added. The resultant yellow solution was stirred for 30 min and a solution of fully protected tri-t-butyl ester of IIA (400 mg) in THF (3 mL) was added dropwise. After 1 h the reaction mixture was quenched with aq ammonium chloride and allowed to warm to room temperature. The mixture was diluted with ether and filtered through CELITE. The organic layer was then dried with magnesium sulfate, filtered, concentrated and purified on a column of silica eluted with hexane:ethyl acetate (6:1) to yield the 7-(1-methyl-1-methoxymethyl ether) protected 4'-hydroxy-3-butyl ketone of IIA.

¹HNMR (400 MHz, CDCl₃) δ 7.27–7.15 (m, 5H), 6.88 (dd, J=8.0, 15.6 Hz, 1H), 6.38 (d, J=2.0 Hz, 1H), 5.75 (d, J=15.6 Hz, 1H), 5.13 (brs, 1H), 4.97(brs, 1H), 4.93(s, 1H), 4.26(d, J=2.0 Hz, 1H), 4.1–4.08 (m, 1H), 3.95 (s, 1H), 3.20 (s, 3H), 2.80 (dd, J=5.6 Hz, 1H), 2.67–1.97 (m, 10H), 1.65 (s, 9H), 1.54–1.05 (m, 9H), 1.34 (s, 9H), 1.33 (s, 3H), 1.26 (s, 3H), 0.98 (d, J=6.8 Hz, 3H), 0.84 (s, J=7.2 Hz, 3H), 0.82–0.77 (m, 9H).

Step B: Acetylation of IIA-3-butyl ketone-7-(1-methyl-1-methoxyethyl ether)-4'-hydroxy-4,5-di-t-butyl ester A solution of 7-(1-methyl-1-methoxyethyl ether) protected 4'-hydroxy-3-butyl ketone of IIA (50.6 mg), triethylamine (32.3 μL), 4-dimethylamino pyridine (7.1 mg) and acetic anhydride (8.2 μL) in methylene chloride (0.58 mL) was stirred at 23° for 2 h. The reaction mixture was diluted with methylene chloride and washed with 1N HCl, 5% aq sodium bicarbonate, brine, dried over anhydrous sodium sulfate, filtered and evaporated to yield the 7-(1-methyl-1-methoxymethyl ether) protected 4,5-di-t-butyl ketone of IIA.

¹HNMR (400 MHz, CDCl₃) δ 7.26–7.12 (m, 5H), 6.89 (dd, J=8.4, 15.6 Hz, 1H), 6.40 (d, J=1.6 Hz, 1H), 5.77 (d, J=1.5.6 Hz, 1H), 5.12 (d, J=5.2 Hz, 1H), 4.97 (brs, 1H), 4.96 (brs, 1H), 4.94 (s, 1H), 4.23 (d, J=1.6 Hz, 1H), 3.98 (s, 1H), 3.20 (s, 3H), 2.75–1.96 (m, 10H), 2.08 (s, 3H), 1.53–1.05 (m, 9H), 1.35 (s, 9H), 1.33 (s, 3H), 1.26 (s, 3H), 0.98 (d, J=6.8 Hz, 3H), 0.86–0.79 (m, 9H).

Step C: Reduction of IIA-3-butyl ketone-7-(1-methyl-1-methoxy-ethyl ether)-4,5-di-t-butyl ester to the corresponding pentyl alcohol Sodium borohydride (9.9 mg) was added to a solution of the ketone (241 mg) in methanol (1.5 mL) at 0°. After stirring for 30 min, the reaction mixture was quenched with saturated aq. sodium bicarbonate, warmed to room temperature and extracted with methylene chloride. The organic layer was dried over sodium sulfate, filtered, evaporated under vacuum and purified by flash column over silica and eluted with 3:1 hexane-ethyl acetate to yield the single alcohol.

¹H NMR (400 MHz, CDCl₃) δ 7.26–7.11 (m, 5H), 6.88 (dd, J=8, 15.6 Hz, 1H), 6.40 (d, J=1.6 Hz, 1H), 5.77 (d, J=15.6 Hz, 1H), 5.09 (d, J=5.2 Hz, 1H), 4.96 (brs, 1H), 4.93 (brs, 1H), 4.44 (d, J=8.4 Hz), 1H), 4.17 (d, J=1.6 Hz), 3.86–3.83 (m, 1H), 3.80 (s, 1H), 3.19 (s, 3H), 2.70 (dd, J=5.2 Hz, 13.6 Hz, 1H), 2.42–1.88 (m, 7H), 2.06(s, 3H), 1.63–1.04 (m, 11H), 1.60 (s, 9H), 1.38 (s, 3H), 1.33 (s, 3H), 1.27 (s, 3H), 0.98 (d, J=6.8 Hz, 3H), 0.87 (t, J=7.2 Hz, 3H), 0.82–0.78 (m, 9H).

Step D: IIA-3-butyl ketone 7-(1-methyl-1-methoxyethyl ether) protected 4,5-di-t-butyl-3-butyl ketone of IIA (Example 9, Step B) was deprotected with trifluoroacetic acid (300 μL) in methylene chloride (1.2 mL) over a period of 16 hr to give 3-butyl ketone of IIA.

¹H NMR (300 MHz, CD₃OD) δ 7.32–7.19 (m, 5H), 6.89 (dd, J=8.4, 15.6 Hz, 1H), 6.30 (d, J=1.8 Hz, 1H), 5.83(d, J=15.6 Hz, 1H), 5.14 (d, J=4.5 Hz, 1H), 5.09 (brs, 1H), 5.03 (brs, 1H), 4.07 (d, J=1.8 Hz, 1H), 2.77–2.05 (m, 10H), 2.15 (s, 3H), 1.57–1.11 (m, 9H), 1.07 (d, J=6.6 Hz, 3H), 0.95–0.89 (m, 12H).

Step E: IIA-3-Pentylalcohol(111)

Reduced 7-(1-methyl-1-methoxyethyl ether) protected 4,5-di-t-butyl-3-butyl ketone of IIA described in Example 9 Step C was deprotected in TFA to yield the title compound.

¹H NMR (400 MHz, CD₃OD) δ 7.27–7.12 (m, 5H), 6.82 (dd, J=8.4, 15.6 Hz, 1H), 6.29 (d, J=2.0 Hz, 1H), 5.78 (d, J=15.6 Hz, 1H), 5.05 (d, J=4.8 Hz, 1H), 4.98 (brs, 1H), 4.94 (brs, 1H), 4.39 (d, J=8.4 Hz, 1H), 3.97 (d, J=2.0 Hz), 3.72–3.69 (m, 1H), 2.66 (dd, J=6.4 Hz, 13.6 Hz, 1H), 2.44–1.74 (m, 8H), 2.09 (s, 3H), 1.51–1.09 (m, 10H), 1.02 (d, J=6.8 Hz, 3H), 0.92–0.84 (m, 12H).

EXAMPLE 10

IIA-3-Ethyl alcohol (114)

Step A: IIA-3-methyl ketone-7-(1-methyl-1-methoxyethyl ether)-4,5-di-t-butyl ester IIA-3-methyl ketone-7-(1-methyl-1-methoxyethyl ether)-4,5-di-t-butyl ester was prepared by using the procedure in Example 10 Step A and B, replacing methyllithium for n-butyl lithium.

Step B: Reduction of IIA-3-methyl ketone-7-(1-methyl-1-methoxy-ethyl ether) protected 4,5-di-t-butyl ester 7-(1-methyl-1-methoxyethyl ether) protected 4,5-di-t-butyl-3-methyl ketone of IIA was reduced to the corresponding alcohol by using a procedure similar to Example 9 Step C.

Step C: IIA-3-Ethyl alcohol

Compound obtained in Example 10 Step B was deprotected with TFA in methylene chloride to give IIA-3-ethyl alcohol.

$^1$H NMR (400 MHz, CD$_3$OH) δ 7.26–7.12 (m, 5H), 6.83 (dd, J=8.4, 15.6 Hz, 1H), 6.30 (d, J=2.0 Hz, 1H), 5.78 (dd, 1H, J=1.2, 15.6 Hz), 5.04 (d, 1H, J=4.4 Hz), 4.98 (s, 1H), 4.34 (d, 1H, J=8.4 Hz), 3.98 (d, J=2.4 Hz, 1H), 3.85 (m, 1H), 2.65 (dd, J=2.4, 13.6 Hz, 1H), 2.45 (m, 2H), 2.31 (s, 1H), 2.09 (s, 3H), 1.92 (m, 3H), 1.27–1.42 (m, 3H), 1.24 (d, J=6.4 Hz, 3H), 1.02 (d, 3H, J=6.8 Hz), 0.86 (m, 9H).

EXAMPLE 11

IIA-3-Pentylacetate (113)

Step A:

The product of Example 9 Step C was acetylated to the diacetate by using a similar procedure to that described in Example 9 Step B. $^1$H NMR (300 MHz, CDCl$_3$) δ 7.28–7.12 (m, 5H), 6.88 (dd, J=8.1, 15.9 Hz, 1H), 6.40 (d, J=2.0 Hz, 1H), 5.77 (d, J=15.9 Hz, 1H), 5.09 (d, J=5.1Hz, 1H), 5.05–4.98 (m, 1H) 4.96 (br s, 1H), 4.93 (brs, 1H), 4.71 (d, J=8.1 Hz, 1H), 4.18 (d, J=2.0 Hz, 1H), 3.62 (s, 1H), 3.19 (s, 3H), 2.70 (dd, J=5.1 Hz, 13.5 Hz, 1H), 2.40–1.85 (m, 7H), 2.07 (s, 3H), 1.96 (s, 3H), 1.74–1.04 (m, 11H), 1.66 (s, 9H), 1.37 (s, 9H), 1.34 (s, 3H), 1.27 (s, 3H), 0.98 (d, J=6.6 Hz, 3H), 0.88–0.79 (m, 12H).

Step B: IIA-3-pentyl acetate

This compound was prepared by stirring its di-t-butyl ester in TFA/methylene chloride.

$^1$H NMR (300 MHz, CD$_3$OD) δ 7.28–7.14 (m, 5H), 6.83 (dd, J=8.6, 15.6 Hz, 1H), 6.28 (d, J=2.0 Hz, 1H), 5.78 (d, J=15.6 Hz, 1H), 5.05–5.10 (m, 1H), 5.06 (d, J=5.2 Hz, 1H), 4.98 (brs, 1H), 4.95 (brs, 1H), 4.69 (d, J=9.2 Hz, 1H), 4.18 (d, J=2.0 Hz, 1H), 4.00 (d, J=2.0 Hz, 1H), 2.67 (dd, J=6.4 Hz, 13.6 Hz, 1H), 2.45–1.92 (m, 7H), 2.09 (s, 3H), 1.96 (s, 3H), 1.81–1.09 (m, 11H), 1.02 (d, J=6.8 3H), 0.88–0.84 (m, 12H).

EXAMPLE 12

IIA-3-Ethyl ketone (126)

IIA-4,5-di-t-butyl ester (100 mg) was stirred with N-methylmorpholine (16.2 μL) in dichloromethane (2.5 mL) at room temperature for 25 min. The reaction mixture was then cooled to −20°. Isobutylchloroformate (20.3 μL) was added and stirred for 1 h. Ethyl magnesium chloride was then added and the mixture was stirred for additional 45 min. The reaction was warmed to room temperature and treated with solid ammonium chloride (500 mg), filtered thru silica, evaporated and IIA-3-ethyl ketone was separated from IIA-3-diethyl alcohol.

EXAMPLES 13–22

The following compounds were prepared according to the procedure of Example 14 substituting the appropriate Grignard reagent and were deprotected, separated and purified by reverse phase HPLC as previously outlined.

EXAMPLE 13

IIA-3-Phenethyl ketone (127)

The 1H NMR (CD$_3$OD, 400 MHz) includes δ 7.23–7.08 (m, 10H), 6.87 (dd, 1H, J=15.5, 8.4 Hz), 6.23 (d, 1H, J=2.0 Hz), 5.82 (d, 1H, J=16.0 Hz), 5.07 (s, 1H), 5.08 (d, 1H, J=1.3 Hz), 4.97 (d, 1H, J=12.8 Hz), 4.86 (s, 1H), 4.01 (s, 1H), 2.97–2.93 (m, 1H), 2.82–2.78 (m, 1H), 2.65 (dd, 1H, J=12.0, 6.4 Hz), 2.43–2.34 (m, 6H), 2.05–2.04 (m, 2H), 2.02 (s, 3H), 1.39–1.26 (m, 4H), 1.15–1.09 (m, 2H), 1.03 (d, 3H, J=6.8 Hz), 0.89–0.034 (m, 9H) ppm.

EXAMPLE 14

IIA-3-(Bis-phenethyl)methanol (118)

The 1H NMR (CD$_3$OD, 400 MHz) includes δ 7.72–7.68 (m, 1H), 7.64–7.61 (m, 1H), 7.27–7.01 (m, 13H), 6.85 (dd, 1H, J=15.6, 8.4 Hz), 6.31 (s, 1H), 5.81 (d, 1H, J=15.6 Hz), 5.05 (d, 1H, J=4.8 Hz), 5.02 (s, 1H), 4.99 (s, 1H), 4.88 (s, 1H), 4.05 (s, 3H), 2.65 (dd, 1H, J=13.6, 6.8 Hz), 2.59–2.25 (m, 8H), 2.05 (s, 3H), 2.04–1.84 (m, 2H), 1.47–1.27 (m, 4H), 1.18–1.06 (m, 2H), 1.03 (d, 3H, J=6.4 Hz), 0.99–0.77 (m, 13H) ppm.

EXAMPLE 15

IIA-3-Propyl ketone (124)

The 1H NMR (CD3OD, 400 MHz) includes δ 7.26–7.12 (m, 5H), 6.86 (dd, 1H, J=14.4, 8.0 Hz), 6.25 (s, 1H), 5.81 (d, 1H, J=16.0 Hz), 5.09 (d, 1H, J=4.4 Hz), 5.02 (s, 1H) 4.98 (s, 1H), 4.87 (s, 1H), 4.01 (s, 1H), 2.69–2.59 (m, 3H), 2.46–2.40 (m, 4H), 2.23–2.20 (m, 2H), 2.01 (s, 3H), 2.05–1.98 (m, 2H), 1.56–1.38 (m, 3H), 1.37–1.28 (m, 2H), 1.15–1.08 (m, 5H), 1.03 (d, 3H, J=6.0 Hz), 0.99–0.82 (m, 8H) ppm.

EXAMPLE 16

IIA-3-(Bis-propyl)methanol (117)

The high resolution mass spec (FAB neg) contains M+Na; 783.

EXAMPLE 17

IIA-3-Ethyl ketone

The 1H NMR (CD$_3$OD, 400 MHz) includes δ 7.32–7.15 (m, 5H), 6.93 (dd, 1H, J=20.8, 11.2 Hz), 6.33 (s, 1H), 5.88 (d, 1H, J=21.2 Hz), 5.13 (d, 1H, J=6.0 Hz), 5.06 (s, 1H), 5.02 (s, 1H), 4.94 (s, 1H), 4.06 (s, 1H), 2.73–2.70 (m, 2H), 2.50–2.43 (m, 3H), 2.36 (s, 3H), 2.34–2.29 (m, 3H), 2.15 (d, 3H, J=4.0 Hz), 2.12–2.00 (m, 2H), 1.47–1.33 (m, 2H), 1.20–1.11 (m, 2H), 1.08 (d, 3H, J=8.8 Hz), 1.04–0.87 (m, 11H) ppm.

EXAMPLE 18

IIA-3-(Bis-ethyl)methanol (115)

The $^1$H NMR (CD$_3$OD, 400 MHz) includes δ 7.32–7.18 (m, 5H), 6.91 (dd, 1H, J=21.2, 11.6 Hz), 6.32 (d, 1H, J=2.4 Hz), 5.86 (dd, 1H, J=20.8, 1.2 Hz), 5.11 (d, 1H, J=6.4 Hz), 5.04 (s, 1H), 5.00 (s, 1H), 4.94 (s, 1H), 4.60 (s, 1H), 4.03 (d, 1H, J=2.4 Hz), 2.75 (dd, 1H, J=18.0, 9.6 Hz), 2.53–2.42 (m, 2H), 2.36–2.27 (m, 4H), 2.15 (s, 3H), 2.12–1.91 (m, 2H), 1.67–1.56 (m, 4H), 1.43–1.33 (m, 2H), 1.20–1.13 (m, 2H), 1.08 (d, 3H, J=8.8 Hz), 1.01–0.76 (m, 15H) ppm.

EXAMPLE 19

IIA-3-Phenyl ketone (123)

The $^1$H NMR (CD$_3$OD, 400 MHz) includes δ 7.70 (d, 1H, J=7.2 Hz), 7.46–7.40 (m, 1H), 7.25–7.10 (m, 8H), 6.88 (dd, 1H, J=15.6, 7.2 Hz), 6.24 (s, 1H), 5.80 (d, 1H, J=15.6 Hz), 5.26 (d, 1H, J=2.8 Hz), 5.10 (s, 1H), 4.98 (s, 1H), 4.87 (s, 1H), 4.04 (s, 1H), 2.45 (dd, 1H, J=18.0, 7.2 Hz), 2.39–2.35 (m, 6H), 2.21 (s, 3H), 2.20–1.84 (m, 2H), 1.38–1.27 (m, 2H), 1.12 (d, 2H, J=2.4 Hz), 1.04 (d, 3H, J=6.8 Hz), 0.99–0.79 (m, 9H) ppm.

EXAMPLE 20

IIA-3-(Bis-phenyl)methanol (116)

The $^1$H NMR (CD$_3$OD, 400 MHz) includes δ 7.69 (d, 2H, J=7.2 Hz), 7.43–7.40 (m, 2H), 7.26–7.05 (m, 11H), 6.84 (dd, 1H, J=15.6, 8.4 Hz), 6.39 (d, 1H, J=2.0 Hz), 5.79 (d, 1H, J=16.0 Hz), 5.71 (s, 1H), 4.93–4.84 (m, 4H), 4.14 (s, 1H), 2.60 (dd, 1H, J=13.6, 6.8 Hz), 2.44–2.31 (m, 6H), 2.05 (s, 3H), 2.03–1.86 (m, 2H), 1.40–1.27 (m, 2H), 1.16–1.11 (m, 2H), 1.02 (d, 3H, J=6.8 Hz), 0.90–0.78 (m, 9H) ppm.

EXAMPLE 21

IIA-3-Methylketone (119)

The $^1$H NMR (CD$_3$OD, 400 MHz) includes δ 7.29–7.07 (m, 5H), 6.83 (dd, 1H, J=15.6, 8.5 Hz), 6.25 (s, 1H), 5.78 (d, 1H, J=15.6 Hz), 5.10 (s, 1H), 4.98 (s, 2H), 4.04 (s, 1H), 3.92 (d, 1H, J=5.2 Hz), 2.75 (dd, 1H, J=13.3, 6.2 Hz), 2.50–2.29 (m, 4H), 2.21 (s, 3H), 2.11–1.95 (m, 3H), 1.43–1.27 (m, 4H), 1.17–1.08 (m, 3H), 1.02 (d, 3H, J=6.6 Hz), 0.89–0.78 (m, 9H) ppm.

EXAMPLE 22

IIA-3-(Bis-butyl)methanol (112)

$^1$H NMR (400 MHz, CD$_3$OD) δ 7.14–7.26 (m, 5H), 6.82 (dd, J=8.4, 15.6 Hz, 1H), 6.25 (d, 2.0 Hz, 1H), 5.77 (dd, J=1.2 Mz, 15.6 Hz, 1H), 5.06 (d, 4.8 Hz, 1H), 5.00 and 4.95 (ea s, ea 1H), 4.95 (s, 1H), 4.53 (s, 1H), 3.98 (d, J=2.0 Hz, 1H), 2.68 (dd, 13.4, 6.2 Hz, 1H), 2.43 (m, 3H), 2.30 (m, 1H), 2.00 (s, 3H), 1.86–2.06 (m, 3H), 1.62–1.21 (m, 12H), 0.84–0.92 (m, 14H)

EXAMPLE 23

IIA-3(2-hydroxymethyl ketone (121)

Step A: IIA-3-diazomethylcarbonyl-4,5-t-butyl ester

To a stirred solution of the IIA-4,5-di-t-butyl ester (817 mg, 1.02 mmol) in methylene chloride (17.7 mL) under nitrogen was added N-methylmorpholine (123.1 μL) followed by stirring for 20 min. The mixture was then cooled to −20° and isobutyl chloroformate (145.1 μL) was added dropwise. After stirring at −20° for 1 h, THF (23 mL) was added and the mixture was stirred for an additional 15 min. The precipitate was removed by filtration at −20° and the filtrate was added to a freshly prepared diazomethane etherate solution (0.82 mL, 1.1 eq). After further 30 min stirring at −20° the excess diazomethane was removed under vacuum and the residue was purified by prep TLC (35/36 ethyl acetate/hexane) to give the IIA-3 diazomethyl ketone.

IR$\nu_{CHCl_3}$ 2200 cm$^{-1}$;

$^1$H NMR (400 MHz, CDCl$_3$) δ 7.25–7.16 (m, 5B), 6.89 (dd, J=8.4, 15.7 Hz, 1H), 5.90 (d, J=1.8 Hz, 1H), 5.76 (s), 5.85–5.7(m), 5.06 (d, J=5.05 Hz, 1H), 5.03 (s, 1H), 4.98 (s, 1H), 4.95 (s, 1H), 4.07 (br s, 1H), 4.00 (s, 1H), 2.7–2.63 (m, 1H), 2.44–2.18(m), 2.11 (s, 3H), 1.58–1.48 (ea s, ea 9H), 1.01 (d, J=6.75 Hz, 3H), 0.85 (m, 9H).

Step B: IIA-3-(2-hydroxymethyl ketone)

Hydrolysis of IIA-3-diazomethylketone was carried out by addition of 2.5 mL of trifluoroacetic acid, at 0° to a stirred solution of IIA-3-diazomethyl ketone (250 mg) in 14.3 mL methylene chloride then allowed to stir at room temperature for 30 min. Neutralization of the mixture with aqueous NaH$_2$PO$_4$ and extraction with ethyl acetate gave 200 mg of a product containing IIA-3-hydroxymethylcarbonyl and its trifluoromethyl acetyl methyl ketone (NMR evidene), which was directly hydrolyzed to the final IIA-3-hydroxymethylketone by stirring with 20% NaBCO$_3$ in methanol (2 mL) at RT for 4 h. Quenching with saturated aqueous NaH$_2$PO$_4$ solution and extracted with ethyl acetate, 161 mg of crude IIA-3-hydroxymethyl ketone was isolated as a foam. Further purification by MPLC (medium pressure liquid chromatography) (6:4 acetonitrile/water) gave the purified compound.

$^1$H NMR (400 MHz, CD$_3$OD) δ 7.28–7.22 (m, 5H), 6.84 (dd, J=8.4 15.6 Hz, 1H), 6.25 (d, J=1.85 Hz, 1H), 5.79 (d, J=15.6 Hz, 1H), 5.17 (br s, 1H), 5.06 (d, J=3.84 Hz, 1H), 5.02 (br s), 4.98(s), 4.51 (s, 2H), 4.02 (d, J=1.85 Hz, 1H), 2.70–2.65 (m, 1H), 2.5–2.15(m), 2.11 (s, 3H), 2.05–1.94(m), 1.7–1.05(m), 1.03 (d, J=6.64 Hz, 3H), 0.78–0.92(m); MS (neg FAB) m/e 703

EXAMPLE 24

IIA-3-methyl (128)

Step A: IIA-7-(1-methoxy-1-methylethyl ether)-3-di-thiocarbonatyl methylene-4,5-di-5-butyl ester

To a stirred solution of IIA-7-(1-methoxy-1-methylethyl ether)-4,5-di-t-butyl ester-3-hydroxymethyl (100 mg, Example 1, Step E) in DMF (0.53 mL) at room temperature under nitrogen atmosphere was added DBN (53.9 μL) dropwise. Carbon disulfide (530 μL) was added dropwise to result an instaneous bright red color. After stirring for 30 min, methyl iodide (1.08 mL) was then added which discharged the red color and formed a yellow solution. After an additional 30 min, the mixture was evaporated. The residue was extracted with ethyl acetate, washed with water and brine and evaporated after drying (anhyd. magnesium sulfate) to an oil. Preparative TLC on SiO$_2$ plates (3:7 ethyl acetate/hexane) gave the mono xanthate.

$^1$H NMR (400 MHz, CD$_3$OD) δ 7.28–7.16 (m, 5H), 6.91 (dd, J=8.45, 15.67 Hz, 1H), 6.45 (d, J=1.8 Hz, 1H), 5.85 (d, J=15.67 Hz, 1H), 5.08–5.06 (m, 1H), 5.05 (s. 1H), 5.00 (s, 1H), 4.97 (s, 1H), 4.74 (m, 1H), 4.53 (m, 1H), 4.22 (d, J=1.8 Hz, 1H), 3.19 (s, 3H), 2.68 (m, 1H), 2.55 (s, 3H), 2.5–2.12(m), 2.10 (s, 3H), 2.09–1.82(m), 1.64 (s, 9H), 1.40 (s, 9H), 1.33(s), 1.27(s), 1.02 (d, J=7 Hz, 3H), 0.88 (m, 9H).

Step B: IIA-3-methyl-4,5-di-t-butyl ester

The mono-xanthate obtained above was deoxygenated under free radical condition as follows. Tributylstannane (56.2 μL) in dry xylene (6 mL) was added dropwise to a stirred solution of the monoxanthate (98 mg) in xylene (6 mL) at 150° under nitrogen atmosphere. After heating for 16 h, the mixture was cooled and evaporated in vacuo. IIA-3-methyl-4,5-t-butyl diester was isolated by prep TLC (3:7 ethyl acetate/hexane), R$_f$0.36.

$^1$H NMR (300 MHz, CD$_3$OD) δ 7.34–7.20 (m, 5H), 6.94 (dd, J=8.5, 15.6 Hz, 1H), 6.43 (d, J=1.88 Hz, 1H), 5.86 (d, J=15.6 Hz, 1H), 5.10 (d, J=4.8 Hz, 1H), 5.03–5.00 (ea s, ea 1H), 4.67 (q, 1H), 4.09 (d, J=1.85 Hz, 1H), 2.78–2.65 (m, 1H), 2.55–2.20(m), 2.14 (s, 3H), 1.99–1.93 (m, 2H), 1.63 (s, 9H), 1.47 (s, 9H), 1.12 (d, J=6.24 Hz, 3H), 1.08 (d, J=6.72 Hz, 3H), 0.9 (m, 9H).

Step C: IIA-3-methyl

Deprotection of IIA-3-methyl-4,5-di-t-butyl ester (30.2 mg) was performed by the usual procedure with TFA in methylene chloride to give IIA-3-methyl.

$^1$H NMR (300 MHz, CD$_3$OD) δ 7.33–7.19 (m, 5H), 6.89 (dd, J=8.3, 15.6 Hz, 1H), 6.3 (br s, 1H), 5.85 (d, J=15.6 Hz, 1H), 5.10 (d, J=4.8 Hz, 1H), 5.03–4.99 (ea s, ea 1H), 4.67 (m, 1H), 4.03 (br s, 1H), 2.73–2.69 (2d, J=6.46, ea 1H), 2.56–2.18 (m), 2.14 (s, 3H), 1.96 (m, 2H), 1.56–1.22 (m), 1.16 (d, J=5.86 Hz, 3H), 1.08 (d, J=6.4 Hz, 3H), 0.92 (m, 9H); MS (FAB), m/e 667 [M+Li], 673 [M+2Li], 679 [M+3 Li].

EXAMPLE 25

IIA-3-fluoromethyl (129)

Step A:
IIA-3-fluoromethyl-7-(1-methyl-1-methoxyethyl ether)-4,5-di-t-butylester Diisopropylethylamine (27.6 μL, 0.16 mmol) was added to a stirred solution of the product of Example 1, Step E (105 mg, 0.12 mmol) in 2 mL CH$_2$Cl$_2$ at 0° under nitrogen. After 10 min, diethylaminosulfur trifluoride (19.36 μL, 0.16 mmol) was added dropwise. The mixture was stirred at 0° for 1 h before quenching with aq. NaHCO$_3$. The mixture was stirred at room temperature for 20 min, then the layers separated. The organic phase was washed with salt solution, dried over MgSO$_4$ and evaporated to provide the crude 3-fluoromethyl compound which on prep-TLC (EtOAc/hex 4:6) provided pure protected IIA-3-fluoromethyl.

$^1$H NMR (400 MHz, CD$_3$OD) δ 7.28–7.19 (m, 5H), 6.90 (dd, J=8.53, 15.67 Hz, 1H), 6.48 (d, J=1.9 Hz, 1H), 5.85 (d, J=15.67 Hz, 1H), 5.06 (d, J=4.57 Hz, 1H), 4.98, 4.96 (z br s, ea. 1H), 4.91–4.88 (m), 4.32–4.40; 4.42–4.48 (each m, each 1H), 4.23 (d, J=1.89 Hz, 1H), 3.19 (s, 3H), 2.67 (dd, J=6.48, 13.28 Hz, 1H), 2.5–1.15 (m), 2.1 (s, 3H), 2.05–1.93 (m, 1H), 1.9 –1.8 (m, 1H), 1.61 and 1.40 (ea s, ea 9H), 1.35 (s), 1.28 (s), 1.2–1.1 (m, 2H), 1.03 (d, J=6.69 Hz, 3H), 0.33–0.84 (m, 9H).

Step B

The compound above was deprotected with TFA (300 μL) in CH$_2$Cl$_2$ (1 mL) at room temperature for 16 h to give the IIA-3-fluoromethyl.

$^1$H NMR (400 MHz, CD$_3$OD) δ 7.27–7.15 (m, 5H), 6.86 (dd, J=8.76, 15.77 Hz, 1H), 6.29 (br s, 1H), 5.78 (dd, J=15.77 Hz, 1H), 5.05 (d, J=4.56 Hz, 1H), 5.98 (s, 1H), 5.95–4.84 (m), 4.50 and 4.38 (ea m, ea 1H), 4.02 (br s, 1H), 2.65 (dd, J=6.22, 13.27 Hz, 1H), 2.46–2.16 (m), 2.08 (s, 3H), 2.0–1.89 (m, 2H), 1.4–1.23 (m), 1.19–1.07 (m, 2H), 1.02 (d, J=6.64 Hz, 3H), 0.9–0.8 (m, 9H), MS (FAB-neg) m/z 677.

EXAMPLE 26

IIA-3-difluoromethyl (130)

Step A: IIA-3-aldehyde-7-(1-methyl-1-methoxyethyl ether)-4,5-di-t-butyl ester Dimethylsulfoxide (58.84 μL, 0.83 mmol) was added to a stirred solution of CH$_2$Cl$_2$ (0.60 mL) and the mixture was cooled to −45°. Oxalylchloride (0.23 μL, 0.45 mmol) was added. After 15 min, a solution of the IIA-3-hydroxymethyl (323 mg, 0.38 mmol) in 0.6 mL of CH$_2$Cl$_2$ was added and was stirred for additional 15 min. To this mixture was added diisopropylethyl amine (0.197 mL, 1.13 mmol) and stirring continued at −23° for 30 min. It was diluted with EtOAc and the organic phase was washed with 1N aq. sodium hydrogen sulfate, water, dried over sodium sulfate, and evaporated to give the IIA-3-aldehyde.

$^1$H NMR (400 MHz, CDCl$_3$) δ 9.47 (s, 1H), 7.28–7.08 (m, 5H), 6.87 (dd, J=8.4, 15.7 Hz, 1H), 5.91 (d, J=2.0 Hz, 1H), 5.75 (d, J=15.7 Hz, 1H), 5.08 (t, 1H), 4.98 and 4.95 (ea br s, ea 1H), 4.05 (d, J=2 Hz, 1H), 3.47 (s, 3H), 2.06 (s, 3H), 1.57 and 1.46 (ea s. ea 9H), 1.03 (d, J=6.62 Hz, 3H), 0.82 (m, 9H).

Step B:
IIA-3-Difluoromethyl-7-(1-methyl-1-methoxyethyl ether)-4,5-di-t-butyl ester Diisopropylethylamine (0.16 mL 0.93 mmole) was added dropwise to a stirred solution of the IIA-C3-aldehyde (312 mg, 0.37 mmol) in CH$_2$Cl$_2$ (5 mL) at 0° under N$_2$. After 15 min, diethylaminosulfur trifluoride (0.114 mL, 0.93 mmol) was added dropwise and after 10 min at 0°, the mixture was allowed to stir at ambient temperature overnight. The IIA-3-difluoromethyl compound was isolated by preparative TLC (EtOAc/hex 3:7, R$_f$=0.9), with characteristic resonance (NMR, CD$_3$OD) at δ 4.76 (m. >C$\underline{H}$—CHF$_2$) and 5.58–5.95 (t d, >CH—C$\underline{H}$F$_2$).

Step C: IIA-3-Difluoromethyl

The above compound (60 mg) was deblocked in the usual manner in 2 mL of CH$_2$Cl$_2$ with 0.4 mL of trifluoracetic acid at room temperature for 16 h to give, after purification by HPLC, the IIA-3-di-fluoromethyl compound.

$^1$H NMR (400 MHz, CDCl$_3$) δ 7.30–7.14 (m, 5H), 6.83 (dd, J=8.46, 15.68 Hz, 1H), 6.25 (br s, 1H), 5.82 (t of d, J$_{HF}$=50 Hz), 5.05 (d, J=4.15 Hz, 1H), 4.99 and 4.96 (ea br s, ea 1H), 4.80 (m, 1H), 4.03 (br s, 1H), 2.65 (dd, J=6.2, 13.27 Hz, 1H), 2.51–2.14 (m), 2.10 (s, 3H), 2.05–1.90 (m), 1.43–1.23 (m), 1.22–1.09 (m), 1.03 (d, J=6.68 Hz, 3H), 0.93–0.8 (m, 9H), MS: FAB-neg m/z=695.

EXAMPLE 27

IIA-3-vinyl (231)

Step A: IIA-3-vinyl-4,5-di-t-butyl ester

To a suspension of dried methyltriphenylphosphonium bromide (107.1 mg, 0.3 mM) in anh. THF (3 mL) cooled to −78° C. was added Potassium bis(trimethylsilyl)amide [KN(Si(CH$_3$)$_3$)$_2$)] (400 μL, 0.3 mM). The mixture was warmed to ambient temperature and when the solution turned orange was cooled to −78° C. The IIA-4,5-di-t-butyl-3-aldehyde (118 mg, 0.15 mM) in THF (1 mL). Cooling was stopped and after 30 min. at room temperature, ether and water were added and the ether layer was washed with saturated aqueous NH$_4$Cl and water. Prep tlc (3:1 hexane/ethyl acetate) yielded IIA-3-vinyl-4,5-di-t-butyl ester.

NMR (400 MHz, CDCl$_3$) δ 0.80 (m, 9H), 1.01 (d, J-6.5, 3H), 1.46 (s, tBu), 1.51 (s, tBu), 2.06 (s, 3H CH$_3$CO), 2.02–2.75 (m, 9H), 3.56 (s, 4—OH), 4.01 (d, J=2, H7), 4.86 (d, J=7, C—3H), 4.94 (2s, C4'=CH$_2$), 5.06 (d, J=5 Hz, C$\underline{H}$OAc), 5.28–5.40 (2d, C—3 CH=CH$_2$) 5.72–5.81 (m, C$\underline{H}$=CH$_2$), 5.93 (d, J=2 Hz, 1H), 7.15–7.27 (m, 5H).

Step B: IIA-3-vinyl 60 mg of IIA-3-vinyl-4,5-di-t-butyl ester was stirred with TFA and methylene chloride to give IIA-3-vinyl.

NMR (400 MHz, CD$_3$OD) δ 0.86 (m, 9H), 1.02 (d, J=6.5, 3H), 2.09 (s, 3H CH$_3$CO), 2.02–2.75 (m, 9H), 4.01 (d, J=2Hz, C—7H), 4.95, 4.98 (2s, C4'=CH$_2$), 5.05 (d, J=5 Hz, C$\underline{H}$OAc), 5.3 (4s), 6.29 (d, J=2 Hz, C6—H), 7.15–7.24 (m, 7H). MS (FAB-neg), m/e 671 [M−H].

EXAMPLE 28

IIA-3-butenyl (232)

Step A: IIA-3-butenyl-4,5-di-t-butyl ester

To a suspension of dried butyltriphenylphosphonium bromide (80 mg, 0.2 mM) in anh. THF (2 mL) cooled to −78° C. was added Potassium bis(trimethylsilyl)amide [KN(Si(CH$_3$)$_3$)$_2$)] (266 μL, 0.2 mM). The mixture was warmed to ambient temperature and when the solution turned orange was cooled to −78° C. The IIA-4,5 di t-butyl-3-aldehyde (80 mg, 0.1 mM) in THF (1 mL) cooling was stopped and after 30 min. at room temperature, ether and water were added and the ether layer was washed with saturated NH$_4$Cl and water. Prep tlc (3:1 hexane/ethyl acetate) yielded IA-3-butenyl-4,5-di-t-butyl ester.

NMR (400 MHz, CDCl$_3$) δ 0.80 (m, 9H), 1.02 (d, J=6.5, 3H), 0.90 (t, J=7.5, CH$_3$CH$_2$) 1.46 (s, tBu), 1.52 (s, tBu), 2.06 (s, 3H CH$_3$CO), 2.02–2.75 (m, 9H), 3.68 (s, 4—OH), 4.01 (d, J=2, H7), 4.86 (d, J=7, C—3H), 4.92 (2s, C4'=CH$_2$), 5.07 (d, J=5 Hz, CHOAc), 4.86 (d, J=7, C—3H), 5.53–5.76 (m, C—3 CH=CH), 5.92 (d, J=2 Hz, 1H), 7.15–7.27 (m, 5H).

Step B: IIA-3-butenyl 60 mg of IIA-3-butenyl-4,5 di t-butyl ester was stirred with TFA and methylene chloride to give IIA-3-butenyl.

NMR (400 MHz, CD$_3$OD) δ 0.86 (m, 9H), 1.02 (d, J=6.5, 3H), 2.09 (s, 3H, CH$_3$CO), 2.02–2.75 (m, 9H), 4.01 (d, J=2Hz, C—7H), 4.94, 4.97 (2s, C4'=CH$_2$), 5.05 (d, J=5 Hz, CHOAc), 5.38 (d, J=9 Hz, C3H), 5.60 (m, CH=CH), 6.31 (d, J=2 Hz, C6—H), 7.15–7.24 (m, 7H). MS (FAB-pos), m/e 737 [M+Na].

EXAMPLES 29–42

Following the general procedures for deacylation and preparation of carbamates and ethers, the following compounds were prepared.

EXAMPLE 29

IIA-6-Dodecylaminocarbonyl carbamate-3-bis-butyl methanol (131)

NMR (CD$_3$OD) δ 0.83–0.95 (m, 12 H), 1.29 (bs, (CH$_2$)$_n$), 2.11 (s, OAc), 3.09 (m, CH$_2$NH), 4.03 (bs, H—7), 4.56 (s, H—3), 500 (s, 1H), 5.04 (s, 1H), 5.10 (d, J=5.0 Hz, CHOAc), 6.13 (bs, 1H), 7.13–7.37 (m, ArH); MS (FAB m/z 870 (M+Na).

EXAMPLE 30

IIA-6-Myristyl Ether-3-bis-methyl methanol (132)

NMR (CD$_3$OD) δ 0.84–0.93 (m, 6H), 1.28 (bs, (CH$_2$)$_n$), 2.10 (s, OAc), 2.20 (s, COCH$_3$), 3.44–3.76 (m, CH$_2$O), 4.06 (bs, H—7), 5.00 (s, 1H), 5.04 (s, 1H), 5.10 (d, J=5.0 Hz, CHOAc), 7-12–7.35 (m, ArH); MS (FAB) m/z 755 (M+Na).

EXAMPLE 31

IIA-6-dodecyl aminocarbonyl carbamate-3-butyl ketone (134)

$^1$H NMR (400 MHz, CD$_3$OD) δ 7.21–7.31 (m, 5H), 6.16 (d, J=2.0 Hz, 1H), 5.13 (d, 1H), 5.16 (s, 1H), 4.09 (d, J=2.4 Hz, 1H), 3.12 (m, 2H), 2.6–2.8 (m, 3H), 2.47 (m, 3H), 2.36 (s, 1H), 2.25 (m, 1H), 2.15 (s, 3H), 2.08 (m, 2H), 1.51 (m, 4H), 1.33 (s, 20H), 0.92 (m, 9H).

EXAMPLE 32

IIA-6-Decylamino carbonyl carbamate-3-methyl ketone (135)

$^1$H NMR (400 MHz, CD$_3$OD) δ 7.09–7.27 (m, 5H), 6.11 (d, 1H, J=1.6), 5.07 (d, J=4.4 Hz, 1H), 5.02 (s, 1H), 4.98 (s, 1H), 4.04 (d, J=1.6 Hz, 1H), 3.08 (m, 2H), 2.68 (dd, J=6.0, 14 Hz, 1H), 2.46–2.35 (m, 2H), 2.31 (s, 1H), 2.20 (s, 3H), 2.10 (s, 3H), 2.04 (m, 1H), 1.46 (m, 2H), 1.28 (s, 16H), 1.07 (d, J=6.8, 1H), 0.87 (d, J=6.8 Hz, 3H), 0.87 (t, J=6.4 Hz, 3H).

EXAMPLE 33

IIA-6-Myristyl Ether-3-methyl ketone (136)

NMR (CD$_3$OD) δ 0.83–0.95 (m, 6H), 1.30 (bs, (CH$_2$)$_n$), 2.11 (s, OAc), 3.45–3.75 (m, CH$_2$O), 4.00 (d, J=1.5 Hz H—7), 4.28 (s, H—3), 4.97 (s, 1H), 5.01 (s, 1H), 5.08 (d, J=5.0 Hz, CHOAc), 7.09–7.35 (m, ArH); MS (FAB) m/z 771 (M+Na).

EXAMPLE 34

IIA-6-(6-hydroxyhexylaminocarbonyl carbamate)-3-methyl ketone (137)

$^1$H NMR (400 MHz, CD$_3$OD) δ 7.10–7.29 (m, 5H), 6.11 (d, J=1.7 Hz, 1H), 5.07 (d, J=4.9 Hz, 1H), 4.90–5.01 (m, 3H), 4.36 (t, J=6.6 Hz, 2H), 4.04 (d, J=2.0 Hz, 1H), 3.07–3.12 (m, 1H), 2.68 (dd, J=13.4, 6.4 Hz, 1H), 2.35–2.46 (m, 3H), 2.20 (s, 3H), 2.10 (s, 3H), 2.00–2.08 (m, 2H), 1.68–1.78 (m, 2H), 1.45–1.52 (m, 2H), 1.30–1.42 (m, 4H), 0.87 (d, J=6.7 Hz, 3H).

EXAMPLE 35

IIA-6-(5-oxo-heptylaminocarbonyl carbamate)-3-methyl ketone (140)

$^1$H NMR (400 MHz, CD$_3$OD) δ 7.10–7.29 (m, 5H), 6.11 (d, J=1.7 Hz, 1H), 5.07 (d, J=4.6 Hz, 1H), 4.95–5.05 (m, 3H), 4.04 (d, J=1.9 Hz, 1H), 3.05–3.12 (m, 2H), 2.68 (dd, J=13.5, 6.5 Hz, 1H), 2.35–2.48 (m, 3H), 2.20 (s, 3H), 2.10 (s, 3H), 2.00–2.06 (m, 2H), 0.87 (d, J=6.7 Hz, 3H).

EXAMPLE 36

IIA-6-(6-imidazolylhexylaminocarbonyl carbamate)-3-methyl ketone (141)

$^1$H NMR (400 MHz, CD$_3$OD) δ 8.94 (s, 1H), 7.64 (s, 1H), 7.55 (s, 1H), 7.10–7.29 (m, 5H), 6.17 (d, J=1.8 Hz, 1H), 5.06 (d, J=4.6 Hz, 1H), 4.85–5.03 (m, 3H), 4.24 (t, J=6.7 Hz, 2H), 4.05 (d, J=1.9 Hz, 1H), 2.99–3.19 (m, 3H), 2.21 (s, 3H), 2.10 (s, 3H), 1.99–2.07 (m, 2H), 1.82–1.94 (m, 2H), 0.87 (d, J=6.7 Hz, 3H).

EXAMPLE 37

IIA-6-(6-morpholinylhexylaminocarbonyl carbamate)-3-methyl ketone (142)

$^1$H NMR (400 MHz, CD$_3$OD) δ 7.10–7.29 (m, 5H), 6.15 (d, J=1.80 Hz, 1H), 5.06 (d, J=4.8 Hz, 1H), 4.90–5.03 (m, 3H), 4.05 (d, J=2.0 Hz, 1H), 3.97–4.05 (m, 2H), 3.80–3.92 (m, 2H), 3.42–3.53 (m, 2H), 3.01–3.19 (m, 6H), 2.68 (dd, J=13.6, 6.6 Hz, 1H), 2.30–2.48 (m, 3H), 2.21 (s, 3H), 2.11 (s, 3H), 1.99–2.06 (m, 2H), 0.87 (d, J=6.7 Hz, 3H).

EXAMPLE 38

IIA-6-(3-imidazolylpropylaminocarbonyl carbamate)-3-methyl ketone (143)

$^1$H NMR (CD$_3$OD, 400 MHz) δ 8.90 (s, 1H), 7.66 (s, 1H), 7.55 (s, 1H, 7.16–7.29 (m, 5H), 6.22 (d, J=1.7 Hz, 1H), 5.07 (s, 1H), J=4.5 Hz), 4.87–5.02 (m, 3H), 4.20–4.33 (m, 2H), 4.09 (d, J=2.0 Hz, 1H), 3.05–3.21 (m, 3H), 2.68 (dd J=13.6, 6.6 Hz, 1H), 2.35–2.48 (m, 2H), 2.21 (m, 3H), 2.10 (s, 3H), 2.00–2.08 (m, 4H), 0.87 (d, J=6.7 Hz, 3H).

EXAMPLE 39

IIA-6-(3-morpholinylpropylaminocarbonyl carbamate)-3-methyl ketone (144)

$^1$H NMR (CD$_3$OD, 400 MHz) δ 7.11–7.29 (m, 5H), 6.24 (d, 1H, J=2.0 Hz), 5.06 (d, J=4.6 Hz, 1H), 4.90–5.03 (m, 3H), 4.10 (d, J=2.0 Hz, 1H), 2.68 (dd, J=13.5, 6.5 Hz, 1H), 2.32–2.50 (m, 3H), 2.21 (s, 3H), 2.10 (s, 3H), 0.87 (d, J=6.7 Hz, 3H).

EXAMPLE 40

IIA-6-Myristoyl ester-3-Methyl ketone (146)

NMR (CD$_3$OD) δ 0.85–0.93 (m, 6H), 1.30 (bs, (CH$_2$)$_n$), 2.11 (s, OAc), 2.20 (s, COCH$_3$), 4.03 (bs, H—7), 5.00 (s, 2H), 5.04 (s, 1H), 5.10 ($\overline{d}$, J=5.10 Hz, $\overline{C}$HOAc), 7.11–7.37 (m, Ar$\underline{H}$); MS (FAB) m/z 769 ($\overline{M}$+Na).

EXAMPLE 41

IIA-6-(11-phenoxyundecylaminocarbonyl carbamate)-3-methyl ketone (139)

NMR (200 MHz, CD$_3$OD) δ 0.86 (d, J=6.5 Hz, CHCH$_3$), 1.3 (bs, 18H), 2.1 (s, 3H, CH$_3$COO), 2.1–2.2 (s, 3H, CH$_3$COO), 3.94 (t, CH$_2$NH), 4.04 (bs, C—7H), 6.1 (bs, C6—H), MS (FAB—POS), 848.8 (M+Na), 870.9 (M+2Na).

EXAMPLE 42

IIA-6-(6-aminohexylaminocarbonyl carbamate)-3-methyl ketone (145)

NMR (400 MHz, CD$_3$OD) δ 7.11–7.29 (m, 5H), 6.38 (brs, 1H), 6.15 (d, J=1.9 Hz, 1H), 5.71 (brs, 1H), 5.07 (d, 1H, J=4.6 Hz), 4.90–5.02 (m, 4.05 (d, J=2.0 Hz, 1H), 3.71–3.81 (m, 1H), 2.99–3.19 (m, 3H), 2.88–2.96 (m, 2H), 2.62–2.71 (m, 1H), 2.30–2.50 (m, 3H), 2.21 (s, 3H), 2.10 (s, 3H), 0.87 (d, J=6.4 Hz, 3H).

EXAMPLE 43

IIA-3-hydroxymethyl-6-isopropylaminocarbonyl carbamate (133)

Step A:

IIA-3-(1-methyl-1-methoxyethyloxymethyl)-7-(1-methyl-1-methoxyethyl ether)-3,4-di-t-butyl ester Pyridium p-toluenesulfonate (10.5 mg) was added to a solution at 0° containing IIA-3-hydroxymethyl-3,4-di-t-butyl ester (360 mg 0.456 mmol) and 2-methoxypropene (0.88 mL) in 3.5 mL methylene chloride. After stirring at 0° for 3.5 h, the reaction mixture was neutralized with sat'd aq NaHCO$_3$. An extractive workup was followed by preparative TLC of the residue on silica (EtOAc: hexane 4:6) to give the title compound. R$_f$=0.7

$^1$H NMR (400 MHz, CD$_3$OD) δ 7.29–7.16 (m, 5H), 6.90 (dd, J=8.62, 15.67 Hz, 1H), 6.47 (d, J=1.63 Hz, 1H), 5.85 (d, J=15.67 Hz, 1H), 5.06 (d, J=4.88 Hz, 1H), 4.97 and 4.95 (ea s. ea 1H), 4.73 (m, 1H), 4.19 (d, J=1.63 Hz, 1H), 3.54–3.4 (m, 3H), 3.20 (s, 6H), 2.68 (m, 1H), 2.52–2.14 (m), 2.10 (s, 3H), 2.08–1.75 (m), 1.63 and 1.40 (ea s, ea 9H), 1.38–1.24 (m), 1.2–1.1 (m), 1.03 (d, J=6.64 Hz, 3H), 0.92–0.78 (m, 9H).

The above compound was deacylated in MeOH (4.65 mL) with anhy. NaOAc (201.1 mg) and hydroxyamine hydrochloride (85.12 mg) according to the usual reaction condition to give, in addition t o the partially hydrolyzed product at C3 to hydroxy methyl compound, the C—6 deacylated product.

$^1$H NMR (400 MHz, CD$_3$OD) δ 7.28–7.16 (m, 5H), 5.07 (d, J=4.98 Hz, 1H), 4.98 and 4.96 (ea s, 1H), 4.95 (s, 2H), 4.56 (m, 1H), 4.13 (d, J=1.93 Hz, 1H), 3.5–3.37 (m, 2H), 3.25 and 3.18 (ea s, ea 3}t), 2.68 (dd, J=5.81, 13.28 Hz, 1H), 2.44–2.14 (m), 2.09 (s, 3H), 2.06–1.87 (m), 1.58 and 1.48 (ea s, ea 9H), 1.48 and 1.45 (ea s), 1.28 (s, 6H), 0.84 (d, J=6.74 Hz, 3H).

Step B:

IIA-3-(1-methyl-1-methoxyethyloxymethyl)-7-(1-methyl-1-methoxy-ethyl ether)-6-isopropylaminocarbonyl-6-deacyl-3,4-di-t-butyl ester 1,1-Carbonyldiimidazole (42.44 mg, 0.262 mmol) was added to a stirred solution of the above-obtained compound (92.9 mg, 0.119 mmol) in dry toluene (0.83 mL) at ambient temperature and the mixture was stirred for 5 h before addition of isopropylamine (113 μL, 1.44 mmol). The mixture was stirred at room temperature for 72 h, then evaporated and purified by prep TLC (EtOAc-hex 3:7) to afford the title compound.

$^1$H NMR (200 MHz, CD$_3$OD) δ 7.29–7.14 (m, 6H), 6.96 (d, J=7.81 Hz, 1H), 6.27 (d, J=1.68 Hz, 1H), 5.05 (d, J=5.15 Hz, 1H), 4.99 (br s, 2H), 4.72 (t, J=4.80 Hz, 1H), 4.20 (d, J=1.78 Hz, 1H), 3.8–3.56 (m, 1H), 3.56–3.28 (m, 2H), 3.21 and 3.19 (ea s, ea 3H), 2.78–2.22 (m), 2.08 (s, 3H), 1.62 and 1.44 (ea s, ea 9H), 1.35 and 1.23 (ea s, total 6H), 1.29 (s, 6H), 1.23 (s, 6H), 1.10 (d, J=5.86 Hz, 3H), 0.82 (d, J=6.73 Hz, 3H).

Step C

The above compound was deblocked in 2 mL CH$_2$C$_2$ with 300 mL TFA to give the product.

$^1$H NMR (400 MHz, CD$_3$OD) δ 7.28–7.10 (m, 6H), 6.28–6.04 (m, 1H), 5.06 (m, 1H), 4.98 and 4.96 (ea s, ea 1H), 4.64 (t, J=5.2 Hz), 4.9–4.32 (m), 4.03 (m, 1H), 3.78–3.54 (m, 2H), 2.72–2.6 (m, 1H), 2.46–2.12 (m), 2.09 (s, 3H), 2.03–1.92 (m, 2H), 1.16–1.1 (m, 3H), 0.84 (d, J=6.73 Hz, 3H). MS FAB-neg. m/z=608.5

EXAMPLE 44

To a refluxing solution of IIA-3-methyl ketone (69.6 mg, 0.10 mmol) in CH$_3$CN (3.0 mL) was added DBU (32 μL, 0.20 mmol) and methylchloroacetate (10.6 μL, 0.1 mmol). The reaction was allowed to reflux overnight whereupon it was concentrated in vacuo. The residue was purified by prep HPLC to yield the following:

IIA-3-methyl ketone 4,5bis-acetyloxymethyl ester (180)

$^1$H NMR (400 MHz, CD$_3$OD) includes δ 7.27–7.12 (m, 5H), 6.83 (dd, J=15.7, 6.9 Hz, 1H), 6.14 (d, J=1.8 Hz, 1H), 5.85 (AB q, J=18.8, 5.7 Hz, 2H), 5.81 (d, J=15.0 Hz, 1H), 5.72 (app. s, 2M), 5.06 (d, J=4.2 Hz, 1H), 5.01 (br s, 1H), 5.01 (b s, 1H), 4.97 (br s, 1H), 4.93 (s, 1H), 2.65 (dd, J=13.4, 7.1Hz, 1H), 2.51–2.37 (m, 4H), 2.19 (s, 3H), 2.12 (s, 3H), 2.10 (s, 3H), 2.06 (s, 3H), 1.02 (d, J=6.6 Hz, 3H). Mass Spec FAB (negative ion) 985 (M−1+154).

IIA-3-methyl ketone-5-acetyloxymethyl ester (179)

$^1$H NMR (400 MHz, CD$_3$OD) includes δ 7.27–7.12 (m, 5H), 6.83 (dd, J=15.0, 8.5 Mz, 1H), 6.25 (br s, 1H), 5.82 (d, J=15.3 Hz, 1H), 5.74 (AB q, J=18.3, 5.3 Hz, 2H), 5.06 (d, J=4.4 Hz, 1H), 5.01 (br s, 2H), 4.96 (s, 1H), 3.99 (br s, 1H), 2.65 (dd, J=13.5, 6.4 Hz, 1H), 2.46–2.37 (m, 4H), 2.20 (s, 3H), 2.10 (s, 3H), 2.05 (s, 3H), 1.04 (d, J=6.7 Hz, 3H). Mass Spec FAB (negative ion) 759 (M−1)

IIA-3-methyl ketone-4-acetyloxymethyl ester (178)

$^1$H NMR (400 MHz, CD$_3$OD) includes δ 7.26–7.12 (m, 5H), 6.84 (dd, J=15.6, 8.6 Hz, 1H), 6.11 (d, J=1.8 Hz, 1H), 5.87–5.77 (m, 3H), 5.06 (d, J=4.5 Hz, 1H), 5.01 (br s, 1H), 4.97 (br s 1H), 4.92 (s, 1H), 4.03 (d, 1.9 Hz, 1H), 2.66 (dd, J=12.3, 6.7 Hz, 1H), 2.48–2.37 (m, 3H), 2.2 (s, 3H), 2.10 (s, 3H), 2.08 (s, 3H), 1.02 (d, J=6.7 Hz, 3H). Mass Spec FAB (negative ion) 759 (M−1)

EXAMPLE 45

IIA-3-methyl ketone-4-methyl pivalate ester (177)

To 69.6 mg of IIA-methyl ketone in 3 ml refluxing acetonitrile, 32 μL of DBU and 10.6 μL of chloromethyl pivalate was added and refluxed until completion of reaction. The IIA-3-methyl ketone-4-methyl pivalate ester (5.5 mg) was separated from the 3,4-hismethyl pivalate diester (30.3 mg) by reverse phase HPLC (reverse phase column, eluted with acetonitrile-water).

$^1$H NMR (400 MHz, CD$_3$OD) δ 7.33–7.10 (m, 5H), 6.85 (dd, J=8.3, 15.6 Hz, 1H), 6.10 (s, 1H), 5.85–5.7 (m, 3H), 5.06 (d, J=4.8 Hz, 1H), 4.92–4.85 (ea s, ea 1H), 4.06 (s, 1H), 2.73–2.69 (2d, ea 1H), 2.56–2.18(m), 2.20 and 2.10 (ea s, ea 3H), 1.96–2.05 (m, 2H), 1.5–1.2(m), 1.20 (s, 9H), 1.08 (d, J=6.4 Hz, 3H), 0.92 (m, 9H). Mass Spec FAB (negative ion) 801 (M−1)

EXAMPLE 46

IIA-3-methyl ketone-4-isoamyl ester (176)

To a refluxing solution of IIA-3-methyl ketone (200 mg, 0.29 mmol) in CH$_3$CN (3.0 mL) was added DBU (43 μL, 0.29 mmol) and isoamyliodide (38 μL, 0.29 mmol). The reaction was allowed to reflux overnight whereupon it was concentrated in vacuo. The residue was purified by prep HPLC to yield the title compound.

$^1$H NMR (400 MHz, CD$_3$OD) includes δ 7.27–7.12 (m, 5H), 6.84 (dd, J=15.6, 8.5 Hz, 1H), 6.20 (d, J=1.9 Hz, 1H), 5.79 (d, J=15.6 Hz, 1H), 5.07 (d, J=4.5 Hz, 1H), 5.02 (br s, 1H), 4.97 (br s, 1H), 4.92 (s, 1H), 4.31–4.23 (m, 2H), 4.03 (d, 1.9 Hz, 1H), 2.21 (s, 3H), 2.10 (s, 3H), 1.03 (d, J=6.7 Hz, 3H). Mass Spec FAB (negative ion) 757 (M−1).

EXAMPLE 47

IIA-3-methyl ketone-4-t-butylmethyl acetate ester (183)

To a refluxing solution of IIA-3-methyl ketone (200 mg, 0.29 mmol) in CH$_3$CN (3.0 mL) was added DBU (43 μL, 0.29 mmol) and t-butyl chloroacetate (43 μL, 0.29 mmol). The reaction was allowed to reflux overnight whereupon NaI (5 mg) was added and the temperature was raised. Upon the formation of other products the reaction was concentrated in vacuo. The residue was purified by prep HPLC to yield the title compound.

$^1$H NMR (400 MHz, CD$_3$OD) includes δ 7.27–7.12 (m, 5H), 6.83 (dd, J=15.6, 8.6 Hz, 1H), 6.24 (br s, 1H), 5.78 (d, J=15.5 Hz, 1H), 5.07 (d, J=4.5 Hz, 1H), 5.02 (br s, 1H), 5.01 (br s, 1H), 4.98 (s, 1H), 4.63 (AB q, J=21.9, 15.6 Hz, 2H), 4.05 (d, 1.7 Hz, 1H), 2.22 (s, 3H), 2.10 (s, 3H), 1.49 (s, 9H). Mass Spec (negative ion) 801 (M−1).

EXAMPLE 48

IIA-3-methyl ketone-4,5-dimethyl ester (181)

To a refluxing solution of IIA-3-methyl ketone (80.0 mg, 0.12 mmol) in CH$_3$CN (3.0 mL) was added DBU (37 μL, 0.23 mmol) and methyl iodide (7.7 μL, 0.12 mmol). The reaction was allowed to reflux for 2 hours whereupon it was concentrated in vacuo. The residue was purified by prep HPLC to yield the title compound.

$^1$H NMR (400 MHz, CD$_3$OD) includes δ 7.27–7.12 (m, 5H), 6.78 (dd, J=16.5, 8.9 Hz, 1H), 6.23 (d, J=2.0 Hz, 1H), 5.79 (d, J=15.6 Hz, 1H), 5.07 (d, J=5.5 Hz, 1H), 5.02 (br s, 1H), 4.97 (br s, 1H), 4.95 (s, 1H), 4.04 (d, J=2.1 Hz, 1H), 3.84 (s, 3H), 3.60 (s, 3H), 2.66 (dd, J=13.4, 6.7 Hz, 1H), 2.49–2.40 (m, 4H), 2.19 (s, 3H), 2.10 (s, 3H), 1.03 (d, J=6.6 Hz, 3H). Mass Spec FAB (negative ion) 743 (M−1+ 4Li).

EXAMPLE 49

IIA-3-methyl-4-methylpivalate diester (148) and IIA-3-methyl-4,5-pivaloxymethyl ester (149)

To IIA-3-methyl (105 mg) in 3 mL refluxing acetonitrile, 24 μL of DBU and 23 μL of chloromethyl pivalate was added and refluxed until completion of reaction. The IIA-3-methyl-4-methyl pivalate was separated from the 4,5-his-methyl pivalate by reverse phase HPLC (reverse phase column, eluted with acetonitrile-water).

$^1$H NMR (400 MHz, CD$_3$OD) δ 7.33–7.19 (m, 5H), 6.85 (dd, J=8.3, 15.6 Hz, 1H), 6.28 (s, 1H), 5.85–5.7 (m, 3H), 5.06 (d, J=4.8 Hz, 1H), 4.92–4.85 (ea s, ea 1H), 4.67 (m, 1H), 4.0 (s, 1H), 2.73–2.69 (2d, ea 1H), 2.56–2.18 (m), 2.10 (s, 3H), 1.96 (m, 2H), 1.5–1.2 (m), 1.20 (s, 9H), 1.16 (d, J=5.86 Hz, 3H), 1.08 (d, J=6.4 Hz, 3H), 0.92 (m, 9H); MS (FAB), m/e 773 (M+Li).

IIA-3-methyl-4,5-pivaloxymethyl ester (149)

$^1$H NMR (400 MHz, CD$_3$OD) includes δ 7.26–7.12 (m, 5H), 6.83 (dd, J=15.6, 8.7 Hz, 1H), 5.87–5.73 (m, 5H), 4.96 (br s, 1H), 4.93 (br s, 1H), 4.56 (q, J=6.2 Hz, 1H), 2.08 (s, 3H), 1.21 (s, 9H), 1.20 (s, 9H). Mass Spec FAB (negitive ion) 1042 (M−1+154).

EXAMPLE 50

IIA-3-methyl-4-methoxyethyl ester (147)

Step A: IIA-3-methyl-5-benzyl-4-methoxyethyl diester

N-methylmorpholine (44.8 μL, 0.407 mmol) was added to a stirred solution of IIA-3-methyl (244.2 mg, 0.37 mmol) in 6.3 mL CH$_2$C$_2$ at room temperature under N$_2$. After stirring for 20 min, the mixture was cooled to −20°. Isobutyl chloroformate (52.81 μL, 0.407 mmol) was added dropwise, and the mixture was stirred at −20° for 1 h. Tetrahydrofuran (7.92 mL) was added at −20° and the precipitate was filtered after 30 min. At −20°, benzyl alcohol (114.7 μL, 1.11 mmol) was added and the mixture was stirred at 0° for 30 min and 25° for 5 h. After quenching with aq. NH$_4$Cl and the usual extractive workup with EtOAc provided an oil; preparative TLC of which (CH$_2$Cl$_2$:acetone:HOAc=45:3:2) yielded the title compound which was dissolved in 2 mL benzene and heated with O-methoxyethyl-N,N'-diiso-propylisourea (100 mL) at 70° for 3 days.

The mixture was diluted with ether, washed with 1N aq HCl, and brine, dried (MgSO$_4$) and evaporated to an oil. Preparative TLC (EtOAc/hex. 3/7) gave the IIA-3-methyl 4-methoxy-ethyl-5-benzyl diester.

$^1$H NMR (400 MHz, CD$_3$OD) δ 7.46–7.13 (m, 10H), 6.82 (dd, J=8.80, 15.72 Hz, 1H), 6.24 (d, J=2.05 Hz, 1H), 5.81 (d, J=15.72 Hz, 1H), 5.27 (ABq, J=12.13, 18.33 Hz, 2H), 5.03 (d, J=4.52 Hz, 1H), 4.96 and 4.93 (eas. ea 1H), 4.58 (m, 1H), 4.15 (m, 2H), 3.97 (d, J=2.05 Hz, 1H), 3.46 (m, 2H), 3.30 (s, 3H), 2.64 (dd, J=6.55, 13.50 Hz, 1H), 2.53–2.38 (m), 2.38–2.12 (m), 2.09 (s, 3H), 1.95–1.82 (m, 2H), 1.48–1.14 (m), 1.12 (d, J=6.59 Hz, 3H), 1.05 (d, J=6.64 Hz, 3H), 1.00 (d, J=6.18 Hz, 3H), 0.94–0.79 (m, 9H).

Step B: IIA-3-methyl-4-methoxyethyl ester

The debenzylation reaction was carried out by stirring the diester obtained above (7.8 mg) in 0.6 mL of MeOH with 1-methyl-1,4-cyclohexadiene and 4 mg of 10% Pd/C at ambient temperature for 4.5 h to give the IIA-3-methyl-4-methoxyethyl ester.

$^1$H NMR (400 MHz, CD$_3$OD) δ 7.27–7.11 (m, 5H), 6.84 (dd, J=8.81, 15.65 Hz, 1H), 6.48 (br s, 1H), 5.79 (d, J=15.65 Hz, 1H), 5.52 (br s, 1H), 5.04 (d, J=4.57 Hz, 1H), 4.96 and 4.93 (ea s. ea 1H), 4.68 (m, 1H), 4.23 (br s, 2H), 3.92 (br s, 1H), 3.59 (br s, 2H), 3.30 (s, 3H), 2.67 (dd, J=6.5, 13.51Hz, 1H), 2.5–2.12 (m), 2.09 (s, 3H), 2.04–1.79 (m), 1.7–1.2 (m), 1.16 (s), 1.02 (d, J=6.68 Hz, 3H), 0.94–0.78 (m, 9H). MS. FAB-neg. m/z=717.8.

IIA-3-methyl-4-and-5-carbomethoxy (150, 151)

DBU (16.42 μL, 0.11 mmol) was added to a stirred solution of IIA-3-methyl (69 mg, 0.105 mmol) in 3.5 mL benzene at room temperature under N$_2$. After 10 min, methyliodide (13.1 μL, 0.21 mmol) was added and the mixture was left at ambient temperature for 4 days. The mixture evaporated and the residue was purified by prep TLC on silica (CH$_2$Cl$_2$-acetone -HOAc=46:3:1) to give the desired product.

$^1$H NMR (400 1MHz, CD$_3$OD) indicated a mixture of C4 and C5 methyl carboxylic ester with resonances at δ 3.67 and 3.81. HPLC purification on a reverse column (CH$_3$CN—H$_2$O) provided 2 peaks. NMR still showed contamination and was recombined.

$^1$H NMR (400 MHz, CD$_3$OD) δ 7.27–7.10 (m, 5H), 6.78 (dd, J=8.81, 15.63 Hz, 1H), 6.25 (d, J=2.17 Hz, 1H), 5.77 (d, J=15.63 Hz, 1H), 5.04 (d, J=4.98 Hz, 1H), 4.97 and 4.95 (ea s, ea 1H), 4.95–4.80 (m), 4.60 (q, 1H), 3.99 (d, J=2.17 Hz, 1H), 3.81 and 3.67 (ea s, ea 3H), 3.66–3.52 (m), 3.37–3.32 (m), 2.72–2.58 (m, 2H), 2.52–2.40 (m), 2.38–2.12 (m), 2.09 (s, 3H), 2.06–1.66 (m), 1.06 (d, J=6.18 Hz, 3H), 1.03 (d, J=6.64 Hz, 3H), 0.92–0.78 (m, 9H).

EXAMPLE 51

IIA-3-methyl-4-(4-methyl-1,3-dioxolen-2-one-5-ylmethyl) ester,
5-(4-methyl-1,3-dioxolen-2-one-5-ylmethyl) ester and
4,5-di-(4-methyl-1,3-dioxolen-2-one-5-ylmethyl) esters (171, 172. 173)

To a stirred solution of IIA-3-methyl (100.9 mg, 0.153 mmol) in 2 mL THF at 0° under N$_2$ was added 1,8-diazabicyclo[5,4,0]undec-7-ene (DBU, 27.4 mL, 0.183 mmol) dropwise. After stirring at 0° for 10 min, then 10 min more at room temperature, 4-bromomethyl-5-methyl-1,3-dioxolen-2-one (Kanebo, 58.95 mg, 0.305 mmol) was added dropwise, stirred for 10 min, then heated at 60° for 2 days. Products were isolated by evaporation, prep. HPLC on a reverse phase column to give IIA-3-methyl-4-(4-methyl-1,3-dioxolen-2-one-5-ylmethyl) ester.

$^1$H NMR (400 MMz, CD$_3$OD) δ 7.27–7.14 (m, 5H), 6.84 (dd, J=8.48, 15.66 Hz, 1H), 6.22 (d, J=2.20 Hz, 1H), 5.76 (d, J=15.66 Hz, 1H), 5.16 (d, J=13.87 Hz, 1H), 5.04 (d, J=4.57 Hz, 1H), 4.98 (d, J=4.29 Hz, 1H), 4.95 (br s, 1H), 4.58 (m, 1H), 3.99 (d, J=2.20 Hz, 1H), 2.65 (dd, J=6.83, 13.28 Hz, 1H), 2.48–2.15 (m), 2.14 and 2.09 (ea s, ea 3H), 2.0–1.84 (m, 2H), 1.43–1.24 (m), 1.09 (d, J=6.18 Hz, 3H), 1.02 (d, J=6.68 Hz, 3H), 0.92–0.8 (m, 9H). MS, FAB-neg m/z=771.

Also IIA-3-methyl-5-(4-methyl-1,3-dioxolen-2-one-5-ylmethyl) ester, NMR spectrum in CD$_3$OD similiar to the 4-(4-methyl-1,3-dioxolen-2-one-5-ylmethyl) ester above with characteristic resonances at δ 2.14 and 2.09 (ea s, ea 3H) and 1.08 (d, J=5.49 Hz, 3H), 1.04 (d, J=6.64 Hz, 3H). MS FAB-neg=771.

And IIA-3-methyl-4,5-bis-(4-methyl-1,3-dioxolen-2-one-5-ylmethyl) esters, characteristic resonances in NMR=δ 2.20, 2.14 and 2.09 (ea s, ea 3H); 1.08 (d, J=6.18 Hz, 3H), 1.05 (d, J=6.64 Hz, 3H).

EXAMPLES 52–59

The following compounds were prepared by following the above procedure and replacing kanebo bromide with other appropriate halides.

EXAMPLE 52

IIA-3-methyl-4-glycodimethylamide ester (152)

$^1$H NMR (400 MHz, CD$_3$OD) δ 7.27–7.14 (m, 5H), 6.84 (dd, J=8.57, 15.68 Hz, 1H), 6.28 (d, J=2.19 Hz, 1H), 5.78 (d, J=15.68 Hz, 1H), 5.05 (d, J=4.56 Hz, 1H), 4.98 and 4.95 (ea s, ea 1H), 4.66 (m, 1H), 4.66 (m, 1H), 4.01 (d, J=2.10 Hz, 1H), 3.02 and 2.94 (ea s, ea 3H), 2.66 (dd, J=6.82, 13.28 Hz, 1H), 2.48–2.17 (m), 2.09 (s, 3H), 1.99–1.80 (m), 1.44–1.24 (m), 1.25 (d, J=6.18 Hz, 3H), 1.03 (d, J=6.64 Hz, 3H), 0.92–0.8 (m, 9H). MS (FAB-neg) m/z=744.

EXAMPLE 53

IIA-3-methyl-5-glycodimethyl amide ester (153)

$^1$H NMR (400 MHz, CD$_3$OD) δ 7.27–7.14 (m, 5H), 6.82 (dd, J=8.63, 15.68 Hz, 1H), 6.26 (d, J=2.05 Hz, 1H), 5.86 (d, J=15.68 Hz, 1H), 5 .05 (d, J=4.89 Hz, 1H), 4.97 and 4.94 (ea s, ea 1H), 4.8 3 (d, J=3.28 Hz, 2H), 4.65 (m, 1H), 3.98 (d, J=2.05 Hz , 1H), 3.00 and 2.93 (ea s, ea 3H), 2.65 (dd, J=6.55, 13.28 Hz, 1H), 2.5–2.13 (m), 2.09 (s, 5H), 1.98–1.84 (m), 1.47–1.16 (m), 1.12 (d, J=6.18 Hz, 3H), 1.03 (d, J=6.68 Hz, 3H), 0.93–0.81 (m, 9H). MS (FAB-neg) m/z=744.

EXAMPLE 54

IIA-3-methyl-4-acetoxymethyl ester (154)

1H NMR (400 MHz, CD$_3$OD) δ 7.27–7.12 (m, 5H), 6.83 (dd, J=8.57, 15.67 Hz, 1H), 6.13 (d, J=2.14 Hz, 1H), 5.86 and 5.78 (ca d, J=5.68 Hz, ea 1H), 5.77 (d, J=0.88 Hz, 1H), 5.04 (d, J=4.66 Hz, 1H), 4.97 and 4.94 (ea s, ea 1H), 4.58 (m, 1H), 3.99 (d, J=2.14 Hz, 1H), 2.66 (dd, J=6.4, & 13.27 Hz, 1H), 2.48–2.13 (m), 2.09 and 2.06 (ea s. ea 3H), 1.97–1.89 (m, 2H), 1.43–1.26 (m), 1.19–1.11 (m), 1.09 (d, J=6.18 Hz, 3H), 1.03 (d, J=6.68 Hz, 3H), 0.91–0.8 (m, 9H). MS FAB-neg m/z=731.

EXAMPLE 55

IIA-3-methyl-4,5-diacetoxymethyl ester (155)

$^1$H NMR (400 MHz, CD$_3$OD): general features of the spectrum similar to that for 4-acetoxymethyl ester above with additional characteristic resonances at δ 2.10, 2.09 and 2.06 (ea s, ea 3H), 1.09 (d, J=6.22 Hz, 3H), 1.04 (d, J=6.64 Hz, 3H).

EXAMPLE 56

IIA-3-methyl-4-ECOE(ethoxycarbonyloxyethyl)ester (157)

$^1$H NMR (400 MHz, CD$_3$OD) δ 7.27–7.12 (m, 5H), 6.9–6.73 (m, 2H), 6.29 and 6.17 (ea d, ea J=1.89 Hz, total 1H), 5.81 and 5.77 (ea d, ea J=2.1 Hz, total 1H), 5.05 (br s, 1H), 4.97 and 4.94 (2 br s, ea 1H), 4.58 (m, 1H), 4.24–4.13 (m, 2H), 4.03 and 3.98 (2d, ea. J=1.89 Hz, total 1H), 2.66 (m. 1H), 2.5–2.14 (m), 2.09 (s, 3H), 1.99–1.85 (m), 1.55 (m), 1.51 (d, J=5.44 Hz), 1.43–1.32 (m), 1.30 (m), 1.11 (d, J=5.99 Hz, 3H), 1.03 (d, J=6.64 Hz, 3H), 0.92–0.78 (m, 9H). MS FAB-neg, m/z=775.

EXAMPLE 57

IIA-3-methyl-4-pivaloyloxy-ethyl-3-methyl ester $^1$H NMR (400 MHz, CD$_3$OD) δ 7.27–7.12 (m, 5H), 6.94–6.80 (m, 2H), 6.31 and 6.14 (ea d, ea J=2.0 Hz, total 1H), 5.81 and 5.77 (ea d, ea J=2.68 Hz, total 1H), 5.04 (br s, 1H), 4.98 and 4.95 (ea br s, ea 1H), 4.62–4.50 (m, 1H), 4.02 and 3.99 (ea d, ea J=2.0 Hz, total 1H), 2.7–2.62 (m, 1H), 2.5–2.12 (m), 2.09 (s, 3H), 1.98–1.85 (m), 1.56 and 1.52 (ea d, ea J=5.45 Hz, total 3H), 1.44–1.27 (m), 1.22 and 1.17 (ea s, peak height in ratio of 2:3, total 9), 1.10 (d, J=6.18 Hz, 3H), 1.03 (d, J=6.55 Hz, 3H), 0.92–0.79 (m, 9H). MS FAB-neg. m/z=787.

EXAMPLE 58

IIA-3-methyl-4,5-di-pivaloyloxy-ethyl-3-methyl ester (170)

$^1$H NMR (400 MHz, CD$_3$OD) spectrum resembles that of the 4-monoester above but with an additional 2 resonances in 1.23–1.15 region accounting for an additional tert-butyl group by integration. MS FAB-neg. m/z=916.

EXAMPLE 59

IIA-3-methyl-4-phthalidyl ester (159)

$^1$H NMR (400 MHz, CD$_3$OD) δ 7.93–7.89 (m, 1H), 7.89–7.65 (m, 3H), 7.55 and 7.52 (2s, total 1H), 7.30–7.11 (m, 5H), 6.90–6.80 (m, 1H), 6.22 and 5.95 (ea d, ea J=2.08 Hz, total 1H), 5.80 (d, J=15.72 Hz, 1H), 5.04 (m, 1H), 4.96 and 4.92 (ea d, ea 1H), 4.73–4.60 and 4.60–4.50 (ea m, 1:1 in ratio, total 1H), 4.02 and 3.93 (ea d, in 1:1 ratio, ea. J=2.08 Hz, total 1H), 2.72–2.6 (m, 1H), 2.57–2.16(m), 2.09 and 2.08 (ea s, total 3H), 2.04–1.83 (m), 1.49–1.25 (m), 1.15 (m), 1.06 (m), 0.98–0.78 (m, 9H). MS. FAB-neg. m/z=791.

EXAMPLE 60

IIA-3-fluoromethyl-4-pivaloyloxymethyl (POM) ester (156)

DBU (15.69 μL, 1.05 equiv) was added dropwise to a stirred solution IIA-3-fluoromethyl (67.8 mg, 0.1 mmol) in THF (1.5 μL) at 0° under nitrogen. After 10 min, the mixture was allowed to warm to room temperature and stirred at ambient temperature for 10 min. Pivaloyloxy methyl chloride (28.79 μl, 2 equiv) was added and the mixture was heated at 60° for 2 days. The IIA-3-fluoromethyl-4-POM ester was isolated by preparative HPLC.

$^1$H NMR (400 MHz, CD$_3$OD) δ 7.25 (m, 2H), 7.16 (m, 3H), 6.84 (dd, J=8.43, 15.62 Hz, 1H), 6.18 (d, J=1.98 Hz, 1H), 5.87–5.77 (m, 3H), 5.04 (d, J=4.89 Hz, 1H), 4.97 and 4.95 (ca s, ea 1H), 4.86–4.81 (m, 1H), 4.53–4.35 (m, 2H), 4.03 (d, J=1.98 Hz, 1H), 2.66 (dd, J=6.55, 13.51 Hz, 1H), 2.48–2.4 (m), 2.38–2.10 (m), 2.09 (s, 3H), 1.99–1.90 (m, 2H), 1.43–1.27 (m), 1.18 (s, 9H), 1.2–1.1 (m), 1.02 (d, J=6.64 Hz, 3H), 0.89–0.85 (m, 9H). MS (FAB-neg) m/z=791 HPLC.

EXAMPLE 61

IIA-3-fluoromethyl-4,5-bis-pivaloyloxymethyl ester (160)

$^1$H NMR (400 MHz, CD$_3$OD) δ 7.27–7.20 (m, 2H), 7.20–7.12 (m, 3H), 6.84 (dd, J=8.72, 15.63 Hz, 1H), 6.18 (d, J=1.84 Hz, 1H), 5.9–5.72 (m, 5H), 5.02 (d, J=4.48 Hz, 1H), 4.97 and 4.94 (ea s, ea 1H), 4.97–4.78 (m, 2H), 4.54–4.3 (m, 2H), 4.00 (d, J=1.84 Hz, 1H), 2.64 (dd, J=6.53, 13.52 Hz, 1H), 2.51–2.39 (m), 2.39–2.12 (m), 2.09 (s, 3H), 1.98–1.81 (m, 2H), 1.47–1.23 (m), 1.21 (s, 18H), 1.22–1.10 (m), 1.04 (d, J=6.54 Hz, 3H), 0.92–0.78 (m, 9H)

EXAMPLE 62

IIA-3-methyoxymethyl ether

Step A: IIA-3-methoxymethyl ether-7(1-methyl-1-methoxy ethyl ether)-4,5-di-t-butylester Sodium hydride (13.2 mg, 55% oil dispersion, 0.23 mmol) was added to a stirred solution of IIA-3-hydroxymethyl-4,5-di-t-butyl-7-(1-methyl-1-methoxyethyl ether), 143.6 mg, 0.18 mmol) in 1.78 mL dry DMF at room temperature. After 15 min, MeI (110.3 μL, 13 equiv) was added and the mixture was stirred at room temperature for 1 h. The mixture evaporated and the residue was partitioned between EtOAc and aq. NaH$_2$PO$_4$ and the organic phase was washed with water, salt solution, dried over anhy. MgSO$_4$ and evaporated to a residue. Purification by prep TLC (EtOAc/hex 4:6) gave the protected IIA-3-methoxymethyl ether, R$_f$=0.6. NMR spectrum in CD$_3$OD exhibits characteristic resonances of methoxymethyl group at δ 3.61 in addition to multiplets between δ 3.73–3.53.

Step B: IIA-3-methyoxymethyl ether

The product of Step A was hydrolyzed with TFA in CH$_2$C$_2$ and further purified by HPLC on a reverse phase column (CH$_3$CN—H$_2$O system) to afford the title compound.

$^1$H NHR (200 MHz, CD$_3$OD) 5 7.30–7.10 (m, 5H), 6.86 (dd, J=8.41, 15.61Hz, 1H), 6.38 (d, J=2.24 Hz, 1H), 5.79 (d, J=15.61Hz, 1H), 5.04 (d, J=4.39 Hz, 1H), 4.98; 4.95 (ea br s, ea 1H), 4.58–4.36 (m, 2H), 3.98 (d, J=2.24 Hz, 1H), 3.65 (s, 3H), 3.66–3.59 (m), 2.64 (dd, J=6.73, 13.28 Hz, 1H), 2.52–1.80 (m), 2.10 (s, 3H), 1.45–1.04 (m), 1.03 (d, J=6.62 Hz, 3H), 0.93–0.8 (m, 9H). MS (FAB-neg) m/z=689.

EXAMPLES 63, 64

Compounds 184 and 185 were made by catalytic reduction (Pd/C, methanol) of Compound 120.

EXAMPLE 63

Compound 185

NMR (400 MHz, CD$_3$OD) δ 7.13–7.27 (m, 5H), 6.15 (dd, 1H, J-2.0 Hz, 6.4 Hz), 4.86 (dd, 5.2, 6.4 Hz, 1H), 4.00 (dd, J=2.0, 13.2 Hz, 1H), 2.92–2.71 (m, 3H), 2.31 (m, 3H), 2.17 (m, 1H), 2.11 (d, 3H, J=4.8 Hz), 1.2–2.00 (m, 14H), 1.10 (m, 1H), 0.93 (dd, J=6.8, 12.8 Hz, 4H), 0.83–0.90 (m, 12H).

EXAMPLE 64

Compound 184

NMR (400 MHz, CD$_3$OD) δ 7.23 (t, J=7.4 Hz, 2H), 7.14 (d, J=7.2 Hz, 3H), 6.19 (dd, J=1.8 Hz, 4.2 Hz, 1H), 4.99 (dd, J=3.6 Hz, 1H), 4.01 (dd, J=1.6 Hz, 9.2 Hz, 1H), 2.65 (m, 4H), 2.40 (dd, 1H), 2.30 (m, 3H), 1.88 (m, 4H), 1.64 (m, 4H), 1.16–1.58 (m, 9H), 1.08 (m, 2H), 0.95 (m, 3H), 0.86 (m, 14H).

EXAMPLE 65

Preparation of an Ammonium Salt

A 0.1 mmol sample of the free acid of a compound of Formula (I) is dissolved in 10 mL ethyl acetate. The resulting solution is saturated with gaseous ammonia and the ammonium salt precipitates from solution.

EXAMPLE 66

Preparation of a Potassium Salt

A solution of 0.1 mmol of the free acid of a compound of formula (I) in 10 mL methanol is treated with an aqueous or methanolic solution containing 0.2 mmol of potassium hydroxide. Evaporation of the solvent affords the tri-potassium salt. Addition of between 0.1 and 0.2 mmol of potassium hydroxide yields mixtures of the mono-potassium and di-potassium whose composition depends upon the exact amount of potassium hydroxide added.

In a similar fashion, the sodium and lithium salts can be formed.

EXAMPLE 67

Preparation of a Calcium Salt

A solution of 0.1 mmol of the free acid of a compound of Formula (I) in 20 mL 6:4 methanol:water is treated with an aqueous solution of 0.05 mmol of calcium hydroxide. The solvents are evaporated to give the corresponding calcium salt.

EXAMPLE 68

Preparation of an Ethylenediamine Salt

A solution of 0.1 mmol of the free acid of a compound of Formula (I) in 10 mL of methanol is treated with 0.1 mmol of ethylenediamine. Evaporation of the solvent affords the ethylenediamine salt.

The procedure can also be applied to the preparation of the N,N″-dibenzylethylenediamine salt.

EXAMPLE 69

Preparation of a Tris(hydroxymethyl)aminomethane Salt

To a solution of 0.1 mmol of the free acid of a compound of Formula (I) in 10 mL of methanol is added from 0.1 to 0.2 mmol of tris(hydroxymethyl)aminomethane dissolved in 10 mL methanol. Evaporation of the solvent gives a corresponding salt form, the exact composition of which is determined by the molar ratio of amine added. Similarly prepared are the salts of L-ornithine, L-lysine, and N-methylgluatamine.

EXAMPLE 70

Preparation of an L-arginine Salt

A solution of 0.1 mmol of the free acid of a compound of Formula (I) in 20 mL of 6:4 methanol:water is treated with an aqueous solution of 0.1 to 0.2 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglutamine.

EXAMPLE 71

Oral Composition

As a specific embodiment of an oral composition of a compound of this invention, 20 mg of the compound from Example 3 is formulated with sufficient finely divided lactose to provide a total amount of 580 to 590 mg to fill a size 0 hard gelatin capsule.

What is claimed is:

1. The compound of structural formula (VI)

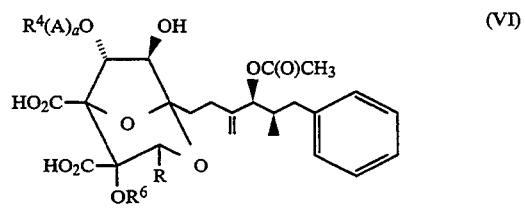

wherein R$^4$—(A)$_a$, R$^6$ and R are each:

| Comp. No. | R$^4$—(A)a— | R$^6$ | R |
|---|---|---|---|
| 134 | —C(O)—NH—(CH$_2$)$_{11}$CH$_3$ | H | —C(O)CH$_2$CH$_2$CH$_2$CH$_3$ |
| 135 | —C(O)—NH(CH$_2$)$_9$CH$_3$ | H | —C(O)CH$_3$ |
| 136 | —(CH$_2$)$_{13}$CH$_3$ | H | —C(O)CH$_3$ |
| 137 | —C(O)—NH(CH$_2$)$_6$OH | H | —C(O)CH$_3$ |
| 138 | —C(O)NH(CH$_2$)$_{11}$CH$_3$ | H | —C(O)CH$_3$ |
| 139 | —C(O)NH(CH$_2$)$_{10}$OC$_6$H$_5$ | H | —C(O)CH$_3$ |
| 140 | —C(O)NH(CH$_2$)$_4$CHO | H | —C(O)CH$_3$ |
| 145 | —C(O)—NH—(CH$_2$)$_6$NH$_2$ | H | —C(O)CH$_3$ |
| 146 | —C(O)(CH$_2$)$_{12}$CH$_3$ | H | —C(O)CH$_3$ |
| 141 | —C(O)NH(CH$_2$)$_6$—N⌒N | H | —C(O)CH$_3$ |
| 142 | —C(O)NH(CH$_2$)$_6$—N⌒O | H | —C(O)CH$_3$ |
| 143 | —C(O)NH(CH$_2$)$_3$—N⌒N | H | —C(O)CH$_3$ |

-continued

| Comp. No. | $R^4$—(A)a— | $R^6$ | R |
|---|---|---|---|
| 144 | —C(O)NH(CH₂)₃—N⟨morpholino⟩ | H | —C(O)CH₃. |

2. A compound selected from the group consisting of:
(a) 3-hydroxyethyl-(1 S,3S,4S ,5R,6R,7RR)-1-[4-hydroxy-3,5-dimethyl-8-phenyl]oct-7-enyl-4,6,7-trihydroxy-6-O-(tetradeca-6,12-dienoyl-2,8-dioxabicyclo[3.2.1]octane-4,5-dicarboxylic acid,
(b) 3-[(1',1'-diphenethyl)-hydroxymethyl]-(1S ,3S ,4S ,5R,6R,7RR)-1-[4-hydroxy-3,5-dimethyl-8-phenyl]oct-7-enyl-4,6,7-trihydroxy-6-O-(tetradeca-6,12-dienoyl-2,8-dioxabicyclo[3.2.1]octane-4,5-dicarboxylic acid,
(c) 3-[(1',1'-dipropyl)-hydroxymethyl]-(1S,3S,4S,-5R,6R,7RR)-1-[4-hydroxy-3,5-dimethyl-8-phenyl]oct-7-enyl-4,6,7-trihydroxy-6-O-(tetradeca-6,12-dienoyl-2,8-dioxabicyclo[3.2.1]octane-4,5-dicarboxylic acid,
(d) 3-[(1',1'-diphenyl)-hydroxymethyl]-(1S,3S,4S,5R,6R ,7RR)-1-[4-hydroxy-3,5-dimethyl-8-phenyl]oct-7-enyl-4,6,7-trihydroxy-6-O-(tetradeca-6,12-dienoyl-2,8-dioxabicyclo[3.2.1]octane-4,5-dicarboxylic acid,
(e) 3-[(1',1'-dibutyl)-hydroxymethyl]-(1S,3S,4S,-5R,6R,7RR)-1-[4-hydroxy-3,5-dimethyl-8-phenyl]oct-7-enyl-4,6,7-trihydroxy-6-O-(tetradeca-6,12-dienoyl-2,8-dioxabicyclo[3.2.1]octane-4,5-dicarboxylic acid, and
(f) 3-(2-hydroxymethyl ketone)-(1S,3S,4S-,5R,6R,7RR)-1-[4-hydroxy-3,5-dimethyl-8-phenyl]oct-7-enyl-4,6,7-trihydroxy-6-O-(tetradeca-6,12-dienoyl-2,8-dioxabicyclo[3.2.1]octane-4,5-dicarboxylic acid.

3. A compound of structural formula (III)

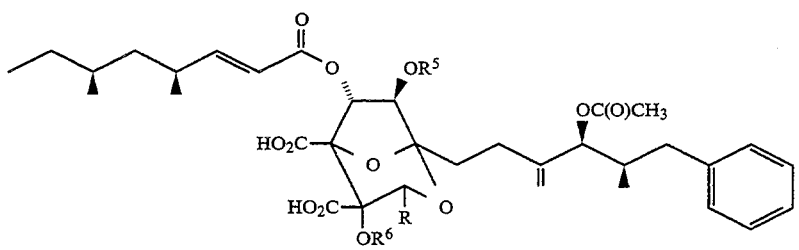

(II)

wherein $R^5$, $R^6$ and R are:

| Compound No. | $R^5$ | $R^6$ | R |
|---|---|---|---|
| 113 | H | H | —CH(OAc)(CH₂)₃CH₃ |
| 119 | H | H | —C(O)CH₃ |
| 120 | H | H | —C(O)(CH₂)₃CH₃ |
| 122 | H | H | —C(O)(2-CH₃—C₆H₄) |
| 123 | H | H | —C(O)—C₆H₅ |
| 124 | H | H | —C(O)(CH₂)₂CH₃ |
| 125 | H | H | —C(O)(CH₂)₂CH₃ |
| 126 | H | H | —C(O)CH₂CH₃ |
| 127 | H | H | —C(O)(CH₂)₂C₆H₅. |
| 128 | H | H | —CH₃ |
| 129 | H | H | —CH₂F |
| 130 | H | H | —CHF₂ |
| 231 | H | H | -vinyl |
| 232 | H | H | -butenyl. |

4. A compound of structural formula (VII):

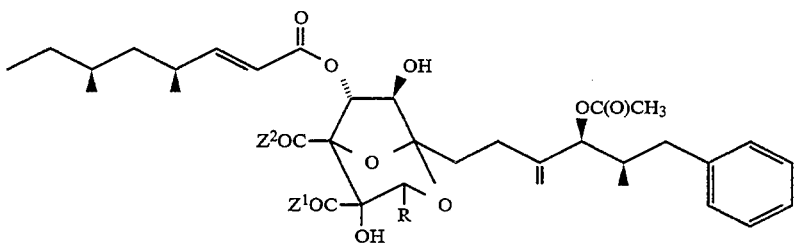

(VII)

wherein R, $Z^1$ and $Z^2$ are:

| Comp. No. | R | $Z^1$ | $Z^2$ |
|---|---|---|---|
| 147 | —CH₃ | —OCH₂CH₂OCH₃ | —OH |
| 148 | —CH₃ | —OCH₂OC(O)C(CH₃)₃ | —OH |
| 149 | —CH₃ | —OCH₂OC(O)C(CH₃)₃ | —OCH₂OC(O)C(CH₃)₃ |
| 150 | —CH₃ | —OCH₃ | —OH |
| 151 | —CH₃ | —OH | —OCH₃ |
| 152 | —CH₃ | —OCH₂C(O)N(CH₃)₂ | —OH |
| 153 | —CH₃ | —OH | —OCH₂C(O)N(CH₃)₂ |
| 154 | —CH₃ | —OCH₂OC(O)CH₃ | —OH |
| 155 | —CH₃ | —OCH₂OC(O)CH₃ | —OCH₂OC(O)CH₃ |
| 156 | —CH₂F | —OCH₂OC(O)C(CH₃)₃ | —OH |
| 157 | —CH₃ | —OCH(CH₃)OC(O)OCH₂CH₃ | —OH |
| 158 | —CH₃ | —OCH(CH₃)OC(O)C(CH₃)₃ | —OH |
| 160 | —CH₂F | —OCH₂OC(O)C(CH₃)₃ | —OCH₂OC(O)C(CH₃)₃ |
| 170 | —CH₃ | —OCH(CH₃)OC(O)C(CH₃)₃ | —OCH(CH₃)OC(O)C(CH₃)₃ |

-continued

| Comp. No. | R | Z¹ | Z² |
|---|---|---|---|
| 174 | —C(O)CH₃ | —OCH₃ | —OH |
| 175 | —C(O)CH₃ | —OH | —OCH₃ |
| 176 | —C(O)CH₃ | —OCH₂OC(O)C(CH₃)₃ | —OH |
| 177 | —C(O)CH₃ | —OH | —OCH₂OC(O)C(CH₃)₃ |
| 178 | —C(O)CH₃ | —OCH₂OC(O)CH₃ | —OH |
| 179 | —C(O)CH₃ | —OH | —OCH₂OC(O)CH₃ |
| 180 | —C(O)CH₃ | —OCH₂OC(O)CH₃ | —OCH₂OC(O)CH₃ |
| 181 | —C(O)CH₃ | —OCH₃ | —OCH₃ |
| 182 | —C(O)CH₃ | —OCH₂C(O)OC(CH₃)₃ | —OH |
| 183 | —C(O)CH₃ | —O(CH₂)₂CH(CH₃)₂ | —OH |
| 159 | —CH₃ | (phthalide-O—) | —OH |
| 171 | —CH₃ | —OCH₂-C(=C(CH₃))-O-C(=O)-O (cyclic carbonate) | —OH |
| 172 | —CH₃ | —OH | —OCH₂-C(=C(CH₃))-O-C(=O)-O (cyclic carbonate) |
| 173 | —CH₃ | —OCH₂-C(=C(CH₃))-O-C(=O)-O (cyclic carbonate) | —OCH₂-C(=C(CH₃))-O-C(=O)-O (cyclic carbonate) |

5. A compound of structural formula (VIII):

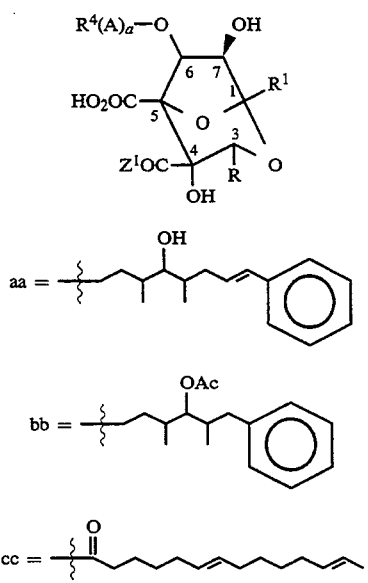

(VIII)

wherein R, R¹, R⁴(A)ₐ and Z¹ are:

| R | R¹ | R⁴(A)ₐ— | Z¹ |
|---|---|---|---|
| —CH₃ | bb | dd | —O—CH₂—C(=C(CH₃))—O—C(=O)—O (cyclic carbonate) |
| —C(O)CH₃ | aa | cc | —OH |
| —C(O)CH₃ | aa | cc | O—CH₂OC-t-Bu |
| —C(O)CH₃ | aa | cc | —O—CH₂—C(=C(CH₃))—O—C(=O)—O (cyclic carbonate) |
| —C(O)CH₃ | bb | dd | —OH |
| —C(O)CH₃ | bb | dd | —OCH₂OC-t-Bu. | aa = (2-methyl-3-hydroxy-4-methyl-6-phenyl-hex-5-enyl)

bb = (2-methyl-3-acetoxy-4-benzyl-pentyl)

cc = (acyl group: —C(O)—CH₂CH₂—CH=CH—CH₂CH₂—CH=CH—)

dd = (acyl group: —C(O)—CH₂CH₂CH₂—CH=CH—CH(CH₃)—CH₂CH₂—phenyl)

-continued

| R | R¹ | R⁴(A)$_a$— | Z¹ |
|---|---|---|---|
| —C(O)CH₃ | bb | dd | 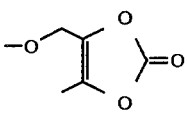 |
| —CH₃ | aa | cc | —OH |
| —CH₃ | aa | cc | —O—CH₂OC-t-Bu |
| —CH₃ | aa | cc | 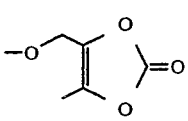 |
| —CH₃ | bb | dd | —OH |
| —CH₃ | bb | dd | —OCH₂OC-t-Bu. |
| —CH₃ | bb | dd | 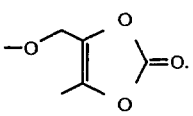 |

6. A compound of structural formula (IX):

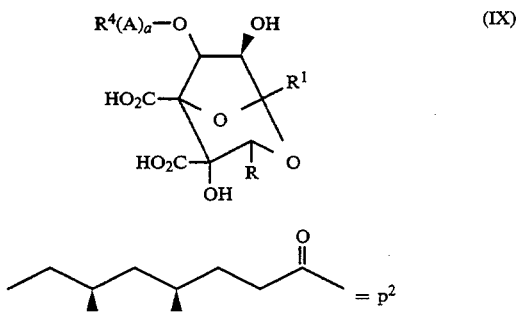

wherein R, R¹, and R⁴—(A)$_a$— are:

| Comp No | R¹ | R | R⁴(A)$_a$ |
|---|---|---|---|
| 184 | —(CH₂)₂CH(CH₃)CH₂CH(CH₃)CH₂C₆H₅ | —C(O)(CH₂)₃CH₃ | p² |
| 185 | —(CH₂)₂CH(CH₃)CH(OAc)CH(CH₃)CH₂C₆H₅ | —C(O)(CH₂)₃CH₃ | p². |

7. A pharmaceutical composition comprising a nontoxic therapeutically effective amount of a compound of claim 2 and a pharmaceutically acceptable carrier.

8. A pharmaceutical composition comprising a nontoxic therapeutically effective amount of a compound of claim 2 in combination with a pharmaceutically acceptable non-toxic cationic polymer capable of binding bile acids in a non-resorbable form in the gastrointestinal tract and a pharmaceutically acceptable carrier.

9. A pharmaceutical composition comprising a nontoxic therapeutically effective amount of a compound of claim 2 in combination with a nontoxic therapeutically effective amount of a cholesterol lowering agent selected from the group consisting of:
   (a) HMG-CoA reductase inhibitor,
   (b) HMG-CoA synthase inhibitor,
   (c) squalene epoxidase inhibitor,
   (d) probucol,
   (e) niacin,
   (f) gemfibrozil,
   (g) clofibrate, and
   (h) LDL-receptor gene inducer.

10. A method of treating hypercholesterolemia comprising the administration to a subject in need of such treatment a nontoxic therapeutically effective amount of a compound of claim 2.

11. A method of treating hypercholesterolemia comprising the administration to a subject in need of such treatment 20 to 100 mg of a compound of claim 2.

12. A method of inhibiting squalene synthase comprising the administration to a subject in need of such treatment a nontoxic therapeutically effective amount of a compound of claim 2.

13. A method for inhibiting fungal growth in a living organism in need of such treatment comprising the oral, systemic, topical or parenteral administration to the living organism of an antifungally effective amount of a compound of claim 2.

14. The method of claim 13 wherein the living organism is a plant, and the compound is administered by topical application to the plant or to the soil in which the plant grows.

15. The method of claim 13 wherein the living organism is a vertebrate.

* * * * *